US008093380B2

(12) United States Patent
Wang et al.

(10) Patent No.: US 8,093,380 B2
(45) Date of Patent: Jan. 10, 2012

(54) **COMPOUNDS WITH THE BICYCLO[4.2.1]NONANE SYSTEM FOR THE TREATMENT OF *FLAVIVIRIDAE* INFECTIONS**

(75) Inventors: Peiyuan Wang, Lilburn, GA (US); Lieven J. Stuyver, Snellville, GA (US); Kyoichi A. Watanabe, Stone Mountain, GA (US); Abdalla Hassan, Chamblee, GA (US); Byoung-Kwon Chun, Duluth, GA (US); Laurent Hollecker, Atlanta, GA (US)

(73) Assignee: Pharmasset, Inc., Tucker, GA (US)

( * ) Notice: Subject to any disclaimer, the term of this patent is extended or adjusted under 35 U.S.C. 154(b) by 2131 days.

(21) Appl. No.: 10/632,997

(22) Filed: Aug. 1, 2003

(65) Prior Publication Data

US 2004/0082574 A1    Apr. 29, 2004

Related U.S. Application Data

(60) Provisional application No. 60/453,716, filed on Aug. 1, 2002.

(51) Int. Cl.
*C07D 403/00* (2006.01)
*C07D 405/00* (2006.01)

(52) U.S. Cl. ...................................... 540/480
(58) Field of Classification Search .................. 514/221; 540/480
See application file for complete search history.

(56) References Cited

U.S. PATENT DOCUMENTS

| 5,026,687 | A | 6/1991 | Yarchoan et al. |
| 5,491,135 | A | 2/1996 | Blough |
| 5,496,546 | A | 3/1996 | Wang et al. |
| 5,506,215 | A | 4/1996 | Johansson et al. |
| 5,633,388 | A | 5/1997 | Diana et al. |
| 5,725,859 | A | 3/1998 | Omer |
| 5,830,905 | A | 11/1998 | Diana et al. |
| 5,837,257 | A | 11/1998 | Tsai et al. |
| 5,846,964 | A | 12/1998 | Ozeki |
| 5,849,800 | A | 12/1998 | Smith |
| 5,858,389 | A | 1/1999 | Elsherbini |
| 5,891,874 | A | 4/1999 | Colacino et al. |
| 5,922,757 | A | 7/1999 | Chojkier |
| 6,030,960 | A | 2/2000 | Morris-Natschke et al. |
| 6,034,134 | A | 3/2000 | Gold et al. |
| 6,056,961 | A | 5/2000 | Lavie et al. |

(Continued)

FOREIGN PATENT DOCUMENTS

FR    2662165 A1    11/1991

(Continued)

OTHER PUBLICATIONS

Morin et al. "Type I Benzophenon-Mediated Nucleophilic Reaction of 5'-Amino-2',5'-dideoxyguanosine. A Model System for the Investigation of Photosensitized Formation of DNA—Protein Cross-Links." Chemical Research in Toxicology. 1995. vol. 8. pp. 792-799.*

(Continued)

*Primary Examiner* — Frederick Krass
*Assistant Examiner* — Benjamin Packard
(74) *Attorney, Agent, or Firm* — Finnegan, Henderson, Farabow, Garrett & Dunner LLP

(57) ABSTRACT

The disclosed invention is a bicyclo[4.2.1]nonane and its pharmaceutically acceptable salt or prodrug, and its composition and method of use to treat Flaviviridae (Hepacivirus, Flavivirus, and Pestivirus) infections in a host, including animals, and especially humans.

1 Claim, 1 Drawing Sheet

U.S. PATENT DOCUMENTS

| | | |
|---|---|---|
| 6,573,248 B2 | 6/2003 | Ramasamy et al. |
| 2002/0055483 A1 | 5/2002 | Watanabe et al. |
| 2002/0147160 A1 | 10/2002 | Bhat et al. |
| 2003/0008841 A1 | 1/2003 | Devos et al. |
| 2003/0028013 A1 | 2/2003 | Wang et al. |
| 2003/0050229 A1 | 3/2003 | Sommadossi et al. |
| 2003/0060400 A1 | 3/2003 | LaColla et al. |
| 2003/0083307 A1 | 5/2003 | Devos et al. |
| 2003/0087873 A1 | 5/2003 | Stuyver et al. |

FOREIGN PATENT DOCUMENTS

| | | |
|---|---|---|
| FR | 2 766 189 A1 | 1/1999 |
| JP | 5-140179 A | 6/1993 |
| JP | 5-140179 A * | 6/1993 |
| WO | WO 98/16184 A2 | 4/1998 |
| WO | WO 99/43691 A1 | 9/1999 |
| WO | WO 01/32153 A2 | 5/2001 |
| WO | WO 01/92282 A2 | 6/2001 |
| WO | WO 01/60315 A2 | 8/2001 |
| WO | WO 01/68663 A1 | 9/2001 |
| WO | WO 01/79246 A2 | 10/2001 |
| WO | WO 01/90121 A2 | 11/2001 |
| WO | WO 02/03997 A1 | 1/2002 |
| WO | WO 02/18404 A2 | 3/2002 |
| WO | WO 02/32920 A2 | 4/2002 |
| WO | WO 02/48165 A2 | 6/2002 |
| WO | WO 02/057287 A2 | 7/2002 |
| WO | WO 02/057425 | 7/2002 |
| WO | WO 02/057425 A2 | 7/2002 |
| WO | WO 02/070533 A3 | 9/2002 |
| WO | WO 02/094289 A1 | 11/2002 |
| WO | WO 02/100415 A2 | 12/2002 |
| WO | WO 03/026589 A2 | 4/2003 |
| WO | WO 03/026675 A1 | 4/2003 |
| WO | WO 03/051899 A1 | 6/2003 |
| WO | WO 03/061385 A1 | 7/2003 |
| WO | WO 03/061576 A2 | 7/2003 |
| WO | WO 03/062255 A2 | 7/2003 |
| WO | WO 03/062256 A1 | 7/2003 |
| WO | WO 03/062257 A1 | 7/2003 |
| WO | WO 03/063771 A2 | 8/2003 |
| WO | WO 03/068162 A2 | 8/2003 |
| WO | WO 03/072757 A2 | 9/2003 |
| WO | WO 03/093290 A2 | 11/2003 |

OTHER PUBLICATIONS

Ewing et al. "Novel reversed cyclonucleoside analogues with a D-ribofuranose glycone". Carbohydrate Research. 1999. vol. 321. pp. 190-196.*

Gilbert et al. "Biochemistry and Clinical Applications of Ribavirin." Antimicrobial Agents and Chemotherapy. 1986. vol. 30. No. 2. pp. 201-205.*

Minakawa et al. "Nucleosides and nucleotides. 138. Synthesis of 3-halo-3-deazainosines: conformational lock with the halogen at the 3-position of the 3-deazainosine in anti-conformation". Heterocycles. 1996. vol. 42. No. 1. pp. 149-154.*

Patani et al (Chem. Rev. 1996, 96, 3147-3176).*

Anderson, G. L., et al., "Pyridopyrimidines. 7. Ribonucleosides structurally related to the antitumor antibiotic sangivamycin," *J. Org. Chem.*, 42(6):997-1000 (1977).

Carroll, Steven S. et al. "Inhibition of Hepatitis C Virus RNA Replication by 2'-Modified Nucleoside Analogs" *The Journal of Biological Chemistry*, 278(14):11979-11984 (2003).

Dymock, B.W., et al., "Novel approaches to the treatment of hepatitis C virus infection," *Antiviral Chemistry & Chemotherapy*, 11(2):79-96 (2000).

Harry-O'Kuru, Rogers E. et al. "2'-C-Alkylribonucleosides: Design, Synthesis, and Conformation" *Nucleosides & Nucleotides*, 16(7-9):1457-1460 (1997).

Pfleiderer, W., et al., "Allgemeine Synthese von Pteridin-N-8-glycosiden," *Chem. Ber.*, 106, 317-331 (1973).

Rizkalla, B.H., et al., "Pyrido[2,3-d]pyrimidines. III. Synthesis of some 8-(β-D-ribofuranosyl)pyrido[2,3-d]pyrimidines structurally related to the antibiotic sangivamycin," *J. Org. Chem.*, 37(25):3980-3985 (1972).

Sasaki et al., "Reactions of the Derivatives of 5-Bromopyrimidine Nucleosides with Sodium Azide", Journal of Organic Chemistry, vol. 41, No. 7, pp. 1100-1104, (1976).

Miles et al., "Circular Dichroism of Nucleoside Derivatives. X. Influence of Solvents and Substituents upon the Cotton Effects of Guanosine Derivatives", Journal of the American Chemical Society, vol. 93, No. 7, pp. 1600-1608, (Apr. 7, 1971).

Notification of Transmittal of the International Search report.

English Language Derwent Abstract for FR 2 766 189 A1.

Hampton A. et al., "Nucleotides. VII. Preparation and Optical Rotatory Dispersion of Some 9β-D-Ribofuranosyl-3,5'-purine Cyclonucleosides," Journal of Organic Chemistry, vol. 32, No. 5, pp. 1688-1691, (May 1967).

Koizumi M. et al., "Molecular Recognition of cAMP by an RNA Aptamer," Biochemistry, vol. 39, No. 30, pp. 8983-8992, (Aug. 1, 2000).

Reitz A.B. et al., "Small-Molecule Immunostimulants. Synthesis and Activity of 7,8-Disubstituted Guanosines and Structurally Related Compounds," Journal of Medicinal Chemistry, vol. 37, No. 21, pp. 3561-3578, (Oct. 14, 1994).

Rosemeyer H. et al., "Syn-Anti Conformational Analysis of Regular and Modified Nucleosides by 1D $^1$H NOE Difference Spectroscopy: A Simple Graphical Method Based on Conformationally Rigid Molecules," Journal of Organic Chemistry, vol. 55, No. 22, pp. 5784-5790, (1990).

Yanachkov I.B. et al., "Amino-Imino Tautomerization of $N^2$-(4-n-Butylphenyl)-2'-deoxy-3,5'-cycloguanosine," Journal of Organic Chemistry, vol. 59, No. 22, pp. 6739-6743, (1994).

Ewing, DF et al. "Novel reversed cyclonucleoside analogues with a D-ribofuranose glycone," *Carbohydrate Research*, 321: 190-196 (1999).

\* cited by examiner

COMPOUNDS WITH THE BICYCLO[4.2.1]NONANE SYSTEM FOR THE TREATMENT OF *FLAVIVIRIDAE* INFECTIONS

This application claims priority to U.S. Provisional Application No. 60/453,716, filed on Aug. 1, 2002, the disclosure of which is incorporated herein.

FIELD OF THE INVENTION

The present invention is directed to compounds and methods for the treatment of Flaviviridae infections that include the administration of an effective amount of a bicyclo[4.2.1] nonane.

BACKGROUND OF THE INVENTION

Flaviviridae are a group of positive, single-stranded RNA viruses with a genome size from 9 to 15 kb. They are enveloped viruses of approximately 40 to 50 nm. An overview of the Flaviviridae taxonomy is available from the International Committee for Taxonomy of Viruses. The group Flaviviridae consists of three genera.

1. Flaviviruses. This genus includes the Dengue virus group (Dengue virus, Dengue virus type 1, Dengue virus type 2, Dengue virus type 3, Dengue virus type 4), the Japanese encephalitis virus group (Alfuy Virus, Japanese encephalitis virus, Kookaburra virus, Koutango virus, Kunjin virus, Murray Valley encephalitis virus, St. Louis encephalitis virus, Stratford virus, Usutu virus, West Nile virus), the Modoc virus group, the Rio Bravo virus group (Apoi virus, Rio Bravo virus, Saboya virus), the Ntaya virus group, the Tick-Borne encephalitis group (tick-born encephalitis virus), the Tyuleniy virus group, Uganda S virus group, and the Yellow Fever virus group. Apart from these major groups, there are some additional Flaviviruses that are unclassified.
2. Hepaciviruses. This genus contains only one species, the hepatitis C virus (HCV), which is composed of many clades, types and subtypes.
3. Pestiviruses. This genus includes bovine viral diarrhea virus-2 (BVDV-2), Pestivirus type 1 (including BVDV), pestivirus type 2 (including hog cholera virus), and pestivirus type 3 (including border disease virus).

One of the most important Flaviviridae infections in humans is caused by the hepatitis C virus (HCV). This is the second major cause of viral hepatitis, with an estimated 170 million carriers world-wide (World Health Organization; Hepatitis C: global prevalence, *Weekly Epidemiological Record*, 1997, 72, 341), 3.9 million of whom reside in the United States (Centers for Disease Control; unpublished data, http://www.cdc.gov/ncidod/diseases/hepatitis/heptab3.htm).

The genomic organization of the Flaviviridae share many common features. The HCV genome is often used as a model. HCV is a small, enveloped virus with a positive, single-stranded RNA genome of ~9.6 kb within the nucleocapsid. The genome contains a single open reading frame (ORF) encoding a polyprotein of just over 3,000 amino acids, which is cleaved to generate the mature structural and nonstructural viral proteins. The ORF is flanked by 5' and 3' non-translated regions (NTRs) of a few hundred nucleotides in length, which are important for RNA translation and replication. The translated polyprotein contains the structural core (C) and envelope proteins (E1, E2, p7) at the N-terminus, followed by the nonstructural proteins (NS2, NS3, NS4A, NS4B, NS5A, NS5B). The mature structural proteins are generated via cleavage by the host signal peptidase (see Hijikata, M. et al., *Proc. Nat. Acad. Sci.*, USA, 1991, 88, 5547; Hussy, P. et al., *Virology*, 1996, 224, 93; Lin, C. et al., *J. Virol.*, 1994, 68, 5063; Mizushima, H. et al., *J. Virol.*, 1994, 68, 2731; Mizushima, H. et al., *J. Virol.*, 1994, 68, 6215; Santolini, E. et al., *J. Virol.*, 1994, 68, 3631; Selby, M. J. et al., *Virology*, 1994, 204, 114; and Grakoui, A. et al., *Proc. Nat. Acad. Sci.*, USA, 1993, 90, 10538). The junction between NS2 and NS3 is autocatalytically cleaved by the NS2/NS3 protease (see Hijikata, M. et al., *J. Virol.*, 1993, 67, 4665 and Bartenschlager, R. et al., *J. Virol.*, 1994, 68, 5045), while the remaining four junctions are cleaved by the N-terminal serine protease domain of NS3 complexed with NS4A (see Fulla, C. et al., *J. Virol.*, 1994, 68, 3753; Lin, C. et al., *J. Virol.*, 1994, 68, 8147; Tanji, Y. et al., *J. Virol.*, 1995, 69, 1575; and Tai, C. L. et al., *J. Virol.*, 1996, 70, 8477). The NS3 protein also contains the nucleoside triphosphate (NTP)-dependent helicase activity which unwinds duplex RNA during replication. The NS5B protein possesses RNA-dependent RNA polymerase (RDRP) activity (see Behrens, S. E. et al., *EMBO J.*, 1996, 15, 12; Lohmann, V. et al., *J. Virol.*, 1997, 71, 8416-8428; and Lohmann, V. et al., *Virology*, 1998, 249, 108), which is essential for viral replication, (Ferrari, E. et al., *J. Virol.*, 1999, 73, 1649). Unlike HBV or HIV, no DNA is involved in the replication of HCV.

Treatment of HCV Infection with Ribavirin

Ribavirin (1-β-D-ribofuranosyl-1H-1,2,4-triazole-3-carboxamide) is a synthetic, non-interferon-inducing, broad-spectrum antiviral nucleoside analog sold under the trade name VIRAZOLE® (Merck Index, 11th edition, Editor: Budavari, S., Merck & Co., Inc., Rahway, N.J., p. 1304, 1989). U.S. Pat. Nos. 3,798,209 and RE 29,835 disclose and claim ribavirin. Ribavirin is structurally similar to guanosine, and has in vitro activity against several DNA and RNA viruses including Flaviviridae (Gary L. Davis, *Gastroenterology* 118:S104-S114, 2000).

Ribavirin reduces serum amino transferase levels to normal in 40% of patients, but it does not lower serum levels of HCV-RNA (Gary L. Davis, *Gastroenterology* 118:S104-S114, 2000). Thus, ribavirin alone is not effective in reducing viral RNA levels. Additionally, ribavirin has significant toxicity and is known to induce anemia.

Ribavirin is not approved for monotherapy against HCV. It has been approved in combination with interferon alpha-2a or interferon alpha-2b for the treatment of HCV.

Treatment of HCV Infection with Interferon

Interferons (IFNs) have been commercially available for the treatment of chronic hepatitis for nearly a decade. IFNs are glycoproteins produced by immune cells in response to viral infection. IFNs inhibit replication of a number of viruses, including HCV, and when used as the sole treatment for hepatitis C infection, IFN can in certain cases suppress serum HCV-RNA to undetectable levels. Additionally, IFN can normalize serum amino transferase levels. Unfortunately, the effect of IFN is temporary, and a sustained response occurs in only 8%-9% of patients chronically infected with HCV (Gary L. Davis, *Gastroenterology* 118:S104-S114, 2000). Most patients, however, have difficulty tolerating interferon treatment, which causes severe flu-like symptoms, weight loss, and lack of energy and stamina.

A number of patents disclose Flaviviridae, including HCV, treatments, using interferon-based therapies. For example, U.S. Pat. No. 5,980,884 to Blatt et al. discloses methods for retreatment of patients afflicted with HCV using consensus interferon. U.S. Pat. No. 5,942,223 to Bazer et al. discloses an anti-HCV therapy using ovine or bovine interferon-tau. U.S. Pat. No. 5,928,636 to Alber et al. discloses the combination therapy of interleukin-12 and interferon alpha for the treatment of infectious diseases including HCV. U.S. Pat. No. 5,849,696 to Chretien et al. discloses the use of thymosins, alone or in combination with interferon, for treating HCV. U.S. Pat. No. 5,830,455 to Valtuena et al. discloses a combination HCV therapy employing interferon and a free radical scavenger. U.S. Pat. No. 5,738,845 to Imakawa discloses the use of human interferon tau proteins for treating HCV. Other interferon-based treatments for HCV are disclosed in U.S. Pat. No. 5,676,942 to Testa et al., U.S. Pat. No. 5,372,808 to Blatt et al., and U.S. Pat. No. 5,849,696. A number of patents also disclose pegylated forms of interferon, such as, U.S. Pat. Nos. 5,747,646, 5,792,834, and 5,834,594 to Hoffmann-La Roche Inc; PCT Publication Nos. WO 99/32139 and WO 99/32140 to Enzon; WO 95/13090 and U.S. Pat. Nos. 5,738, 846 and 5,711,944 to Schering; and U.S. Pat. No. 5,908,621 to Glue et al.

Interferon alpha-2a and interferon alpha-2b are currently approved as monotherapy for the treatment of HCV. ROFERON®-A (Roche) is the recombinant form of interferon alpha-2a. PEGASYS® (Roche) is the pegylated (i.e. polyethylene glycol modified) form of interferon alpha-2a. INTRON®A (Schering Corporation) is the recombinant form of interferon alpha-2b, and PEG-INTRON® (Schering Corporation) is the pegylated form of interferon alpha-2b.

Other forms of interferon alpha, as well as interferon beta, gamma, tau, and omega are currently in clinical development for the treatment of HCV. For example, INFERGEN® (interferon alphacon-1) by InterMune, OMNIFERON® (natural interferon) by Viragen, ALBUFERON® by Human Genome Sciences, REBIF® (interferon beta-1a) by Ares-Serono, omega interferon by BioMedicine, oral interferon alpha by Amarillo Biosciences, and interferon gamma, interferon tau, and interferon gamma-1b by InterMune are in development.

Combination of Interferon and Ribavirin

The current standard of care for chronic hepatitis C is combination therapy with an alpha interferon and ribavirin. The combination of interferon and ribavirin for the treatment of HCV infection has been reported to be effective in the treatment of interferon naïve patients (Battaglia, A. M. et al., *Ann. Pharmacother.* 34:487-494, 2000), as well as for treatment of patients when histological disease is present (Berenguer, M. et al., *Antivir. Ther.* 3(Suppl. 3):125-136, 1998). Studies have shown that more patients with hepatitis C respond to pegylated interferon-alpha/ribavirin combination therapy than to combination therapy with unpegylated interferon alpha. However, as with monotherapy, significant side effects develop during combination therapy, including hemolysis, flu-like symptoms, anemia, and fatigue. (Gary L. Davis, Gastroenterology 118:S104-S114, 2000).

Combination therapy with PEG-INTRON® (peginterferon alpha-2b) and REBETOL® (ribavirin, USP) Capsules is available from Schering Corporation. REBETOL® (Schering Corporation) has also been approved in combination with INTRON® A (interferon alpha-2b, recombinant, Schering Corporation). Roche's PEGASYS® (pegylated interferon alpha-2a) and COPEGUS® (ribavirin) are also approved for the treatment of HCV.

PCT Publication Nos. WO 99/59621, WO 00/37110, WO 01/81359, WO 02/32414, and WO 03/024461 by Schering Corporation disclose the use of pegylated interferon alpha and ribavirin combination therapy for the treatment of HCV. PCT Publication Nos. WO 99/15194, WO 99/64016, and WO 00/24355 by Hoffmann-La Roche Inc also disclose the use of pegylated interferon alpha and ribavirin combination therapy for the treatment of HCV.

Additional References Disclosing Methods to Treat HCV Infections

A number of HCV treatments are reviewed by Dymock et al. in *Antiviral Chemistry & Chemotherapy,* 11:2; 79-96 (2000).

Several substrate-based NS3 protease inhibitors have been identified in the literature, in which the scissile amide bond of a cleaved substrate is replaced by an electrophile, which interacts with the catalytic serine. Attwood et al. (1998), Antiviral peptide derivatives, WO 98/22496; Attwood et al. (1999), *Antiviral Chemistry and Chemotherapy* 10:259-273; Attwood et al. (1999), Preparation and use of amino acid derivatives as antiviral agents, German Patent Publication DE 19914474; Tung et al. (1998), Inhibitors of serine proteases, particularly hepatitis C virus NS3 protease, WO 98/17679. The reported inhibitors terminate in an electrophile such as a boronic acid or phosphonate. Llinas-Brunet et al. (1999), *Hepatitis C inhibitor peptide analogues*, WO 99/07734. Two classes of electrophile-based inhibitors have been described, alphaketoamides and hydrazinoureas.

The literature has also described a number of non-substrate-based inhibitors. For example, evaluation of the inhibitory effects of 2,4,6-trihydroxy-3-nitro-benzamide derivatives against HCV protease and other serine proteases has been reported. Sudo, K. et al., (1997) *Biochemical and Biophysical Research Communications,* 238:643-647; Sudo, K. et al., (1998) *Antiviral Chemistry and Chemotherapy* 9:186. Using a reverse-phase HPLC assay, the two most potent compounds identified were RD3-4082 and RD3-4078, the former substituted on the amide with a 14-carbon chain and the latter possessing a para-phenoxyphenyl group.

Thiazolidine derivatives have been identified as micromolar inhibitors, using a reverse-phase HPLC assay with an NS3/4A fusion protein and NS5A/5B substrate. Sudo, K. et al., (1996) *Antiviral Research* 32:9-18. Compound RD-1-6250, possessing a fused cinnamoyl moiety substituted with a long alkyl chain, was the most potent against the isolated enzyme. Two other active examples were RD4 6205 and RD4 6193.

Other literature reports screening of a relatively small library using an ELISA assay and the identification of three compounds as potent inhibitors, a thiazolidine and two benzanilides. Kakiuchi N. et al., *J. EBS Letters* 421:217-220; Takeshita N. et al., *Analytical Biochemistry* 247:242-246, 1997. Several U.S. patents disclose protease inhibitors for the treatment of HCV. For example, U.S. Pat. No. 6,004,933 to Spruce et al. discloses a class of cysteine protease inhibitors for inhibiting HCV endopeptidase 2. U.S. Pat. No. 5,990,276 to Zhang et al. discloses synthetic inhibitors of hepatitis C virus NS3 protease. The inhibitor is a subsequence of a substrate of the NS3 protease or a substrate of the NS4A cofactor. The use of restriction enzymes to treat HCV is disclosed in U.S. Pat. No. 5,538,865 to Reyes et al.

Isolated from the fermentation culture broth of *Streptomyces* sp., Sch 68631, a phenanthrenequinone, possessed micromolar activity against HCV protease in a SDS-PAGE and autoradiography assay. Chu M. et al., *Tetrahedron Letters* 37:7229-7232, 1996. In another example by the same authors, Sch 351633, isolated from the fungus *Penicillium griseofulvum*, demonstrated micromolar activity in a scintillation proximity assay. Chu M. et al., *Bioorganic and Medicinal Chemistry Letters* 9:1949-1952, 1999. Nanomolar potency against the HCV NS3 protease enzyme has been achieved by the design of selective inhibitors based on the macromolecule eglin c. Eglin c, isolated from the leech, is a potent inhibitor of several serine proteases such as *S. griseus* proteases A and B, α-chymotrypsin, chymase, and subtilisin. Qasim M. A. et al., *Biochemistry* 36:1598-1607, 1997.

HCV helicase inhibitors have also been reported. U.S. Pat. No. 5,633,358 to Diana G. D. et al.; PCT Publication No. WO 97/36554 to Diana G. D. et al. There are a few reports of HCV polymerase inhibitors: some nucleotide analogues, gliotoxin, and the natural product cerulenin. Ferrari R. et al., *Journal of Virology* 73:1649-1654, 1999; Lohmann V. et al., *Virology* 249:108-118, 1998.

Antisense phosphorothioate oligodeoxynucleotides complementary to sequence stretches in the 5'-non-coding region of the HCV are reported as efficient inhibitors of HCV gene expression in in vitro translation and HepG2 HCV-luciferase cell culture systems. Alt M. et al., *Hepatology* 22:707-717, 1995. Recent work has demonstrated that nucleotides 326-348 comprising the 3'-end of the NCR and nucleotides 371-388 located in the core coding region of the HCV RNA are effective targets for antisense-mediated inhibition of viral translation. Alt M. et al., *Archives of Virology* 142:589-599, 1997. U.S. Pat. No. 6,001,990 to Wands et al. discloses oligonucleotides for inhibiting the replication of HCV. PCT Publication No. WO 99/29350 discloses compositions and methods of treatment for hepatitis C infection comprising the administration of antisense oligonucleotides that are complementary and hybridizable to HCV RNA. U.S. Pat. No. 5,922,857 to Han et al. disclose nucleic acids corresponding to the sequence of the pestivirus homology box IV area for controlling the translation of HCV. Antisense oligonucleotides as therapeutic agents have been recently reviewed (Galderisi U. et al., *Journal of Cellular Physiology* 181:251-257, 1999).

Other compounds have been reported as inhibitors of IRES-dependent translation in HCV. Japanese Patent Publication JP-08268890 of Ikeda, N. et al.; Japanese Patent Publication JP-10101591 of Kai, Y. et al. Nuclease-resistant ribozymes have been targeted at the IRES and recently reported as inhibitors in an HCV-poliovirus chimera plaque assay. Maccjak D. J. et al., *Hepatology* 30 abstract 995, 1999. The use of ribozymes to treat HCV is also disclosed in U.S. Pat. No. 6,043,077 to Barber et al. and U.S. Pat. Nos. 5,869,253 and 5,610,054 to Draper et al.

Other patents disclose the use of immune system potentiating compounds for the treatment of HCV. For example, U.S. Pat. No. 6,001,799 to Chretien et al. discloses a method of treating HCV in non-responders to interferon treatment by administering an immune system-potentiating dose of thymosin or a thymosin fragment. U.S. Pat. Nos. 5,972,347 to Eder et al. and 5,969,109 to Bona et al. disclose antibody-based treatments for HCV infection.

U.S. Pat. No. 6,034,134 to Gold et al. discloses certain NMDA receptor agonists having immunomodulatory, antimalarial, anti-Borna virus, and anti-HCV activities. The disclosed NMDA receptor agonists belong to a family of 1-amino-alkylcyclohexanes. U.S. Pat. No. 6,030,960 to Morris-Natschke et al. discloses the use of certain alkyl lipids to inhibit the production of hepatitis-induced antigens, including those produced by HCV. U.S. Pat. No. 5,922,757 to Chojkier et al. discloses the use of vitamin E and other antioxidants to treat hepatic disorders including HCV. U.S. Pat. No. 5,858,389 to Elsherbi et al. discloses the use of squalene for treating HCV infection. U.S. Pat. No. 5,849,800 to Smith et al. discloses the use of amantadine for treatment of HCV infection. U.S. Pat. No. 5,846,964 to Ozeki et al. discloses the use of bile acids for treating HCV infection. U.S. Pat. No. 5,491,135 to Blough et al. discloses the use of N-(phosphonoacetyl)-L-aspartic acid to treat flavivirus infections, such as HCV infection.

Other compounds proposed for treating HCV infection include plant extracts (U.S. Pat. No. 5,837,257 to Tsai et al., U.S. Pat. No. 5,725,859 to Omer et al., and U.S. Pat. No. 6,056,961), piperidenes (U.S. Pat. No. 5,830,905 to Diana et al.), benzenedicarboxamides (U.S. Pat. No. 5,633,388 to Diana et al.), polyadenylic acid derivatives (U.S. Pat. No. 5,496,546 to Wang et al.), 2',3'-dideoxyinosine (U.S. Pat. No. 5,026,687 to Yarchoan et al.), and benzimidazoles (U.S. Pat. No. 5,891,874 to Colacino et al.).

Other agents for the treatment of HCV infection include PEGASYS® (pegylated interferon alfa-2a) by Roche, INFERGEN® (interferon alfacon-1) by InterMune, OMNIFERON® (natural interferon) by Viragen, ALBUFERON® (albinterferon alpha 2b) by Human Genome Sciences, REBIF® (interferon beta-1a) by Ares-Serono, omega interferon by BioMedicine, oral interferon alpha by Amarillo Biosciences, interferon gamma-1b by InterMune, interleukin-10 by Schering-Plough, IP-501 by Interneuron, merimebodib VX-497 by Vertex, SYMMETREL® (amantadine) by Endo Labs Solvay, HEPTAZYME® by RPI, IDN-6556 by Idun Pharma., XTL-002 by XTL, HCV/MF59 by Chiron, CIVACIR® (hepatitis C immune globulin) by NABI, levovirin by ICN, viramidine by ICN, ZADAXIN® (thymosin alfa-1) by Sci Clone, CEPLENE® (histamine dihydrochloride) by Maxim, telaprevir VX 950/LY 570310 by Vertex/Eli Lilly, ISIS 14803 by Isis Pharmaceutical/Elan, IDN-6556 by Idun Pharmaceuticals, Inc., and JTK 003 by AKROS Pharma.

BioChem Pharma Inc. disclosed the use of various 1,3-dioxolane nucleosides for the treatment of a Flaviviridae infection in International Publication No. WO 01/32153.

BioChem Pharma Inc. also disclosed various other 2'-halo, 2'-hydroxy, and 2'-alkoxy nucleosides for the treatment of a Flaviviridae infection in International Publication No. WO 01/60315.

Idenix Pharmaceuticals, Ltd. discloses branched nucleosides and their use in the treatment of HCV and flaviviruses and pestiviruses in International Publication Nos. WO 01/90121 and WO 01/92282, respectively and U.S. Publication Nos. 2003/0050229 A1 and 2003/0060400 A1. A method for the treatment of HCV and flavivirus and pestivirus infections in humans and other host animals is disclosed that includes administering an effective amount of a biologically active 1', 2', and 3'-branched β-D or β-L nucleosides or a pharmaceutically acceptable salt or prodrug thereof, administered either alone or in combination, optionally in a pharmaceutically acceptable carrier.

International Publication Nos. WO 02/18404 and WO 02/100415 to F. Hoffmann-La Roche AG disclose various nucleoside analogs for the treatment of HCV RNA replication.

Pharmasset Limited, in WO 02/32920, discloses various nucleosides for the treatment of a variety of viruses, including Flaviviridae, and in particular HCV.

Merck & Co., Inc. and Isis Pharmaceuticals disclose in International Publication Nos. WO 02/057287 and WO 02/057425 and U.S. Publication No. 2002/0147160 A1 various nucleosides, and in particular several pyrrolopyrimidine nucleosides, for the treatment of viruses whose replication is dependent upon RNA-dependent RNA polymerase, including Flaviviridae, and in particular HCV.

In view of the severity of diseases associated with pestiviruses and flaviviruses, and their pervasiveness in animals, including humans, it is an object of the present invention to provide a compound, method, and composition for the treatment of a host, including animals and especially humans, infected with flavivirus or pestivirus.

It is a further object to provide a compound, method, and composition for the treatment of a host, including animals and especially humans, infected with hepaciviruses.

SUMMARY OF INVENTION

It has been discovered that certain nucleoside derivatives incapable of being phosphorylated at the C-5' position, due to the lack of a free hydroxyl group, are potent inhibitors of HCV. Further, it was discovered that bicyclo[4.2.1]nonane rings, derived from nucleosides, exhibit potent and selective activity against Flaviviridae infection, and in particular against HCV.

In one embodiment, the present invention provides compounds of the general formula (I):

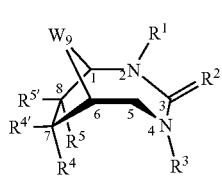

(I)

or a pharmaceutically acceptable salt or prodrug thereof, wherein:

(a) each $R^4$ and $R^{4'}$ is independently hydrogen, halogen (F, Br, Cl, or I), pseudohalogen, CN, $NO_2$, lower alkyl of $C_1$-$C_6$, halogenated lower alkyl, hydroxyl, alkoxy, $CH_2OH$, $CH_2OR^6$, $NH_2$, $NR^6R^7$, or a residue of an amino acid; wherein at least one of $R^4$ and $R^{4'}$ is hydrogen;

(b) each $R^5$ and $R^{5'}$ is independently hydrogen, halogen (F, Br, Cl, or I), pseudohalogen, CN, $NO_2$, lower alkyl of $C_1$-$C_6$, halogenated lower alkyl, hydroxyl, alkoxy, $CH_2OH$, $CH_2OR^6$, $NH_2$, $NR^6R^7$, or a residue of an amino acid; wherein at least one of $R^5$ and $R^{5'}$ is hydrogen;

(c) each $R^6$ and $R^7$ is independently hydrogen, alkyl, halogenated alkyl, alkylene, alkenyl, carbocycle, aryl, heterocycle, heteroaryl, aralkyl, or acyl;

(d) $R^1$ is hydrogen, lower alkyl, alkylene, alkenyl, carbocycle, aryl, heterocycle, heteroaryl, aralkyl, aminoalkyl, aminoaryl, or aminoacyl of $C_1$-$C_6$;

(e) $R^2$ is oxygen, sulfur, NR', or $CR'_2$, wherein each R' is independently hydrogen, lower alkyl, alkylene, alkenyl, aryl, or aralkyl of $C_1$-$C_6$;

(f) $R^3$ is hydrogen, lower alkyl, alkylene, alkenyl, carbocycle, aryl, heterocycle, heteroaryl, aralkyl, aminoalkyl, aminoaryl, or aminoacyl of $C_1$-$C_6$;

(g) alternatively if $R^2$ is NR', then $R^1$ or $R^3$ can come together with NR' to form a substituted or unsubstituted 5-7 membered ring that can include one or more heteroatoms; or (h) if $R^2$ is $CR'_2$, then $R^1$ or $R^3$ can come together with $CR'_2$ to form a substituted or unsubstituted 5-7 membered ring that can include one or more heteroatoms; or (i) if $R^2$ is $CR'_2$, then $R^1$ and $R^3$ can come together with $CR'_2$ to form a substituted or unsubstituted bicyclic ring that can include one or more heteroatoms; and (j) W is O or $CH_2$.

In a preferred embodiment, the $R^5$ or $R^{5'}$ of the bicyclo [4.2.1]nonane is a residue of an amino acid, i.e. a 2'-prodrug of an active bicyclo[4.2.1]nonane wherein $R^5$ or $R^{5'}$ is OH. In one embodiment, the amino acid is valine. In a particular sub-embodiment, the amino acid is L-valine.

In another embodiment, the present invention provides compounds of the general formula 1 (A-D), 2 (A-D), 3 (A-B), 4 (A-B), 5 (A-B), 6 (A-B), 7 (A-C) or 8 (A).

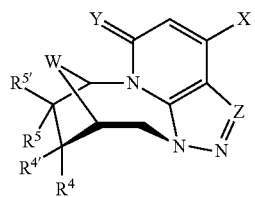

1 (A)

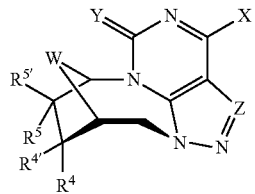

1 (B)

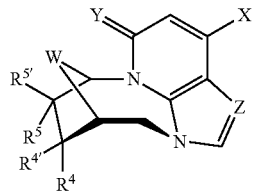

1 (C)

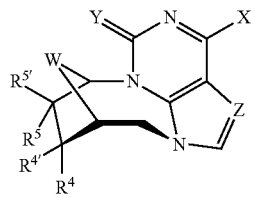

1 (D)

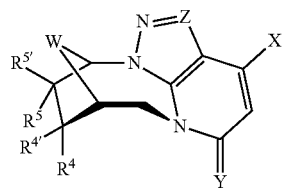

2 (A)

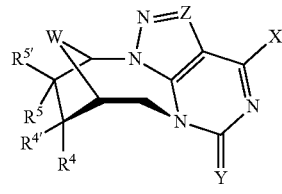

2 (B)

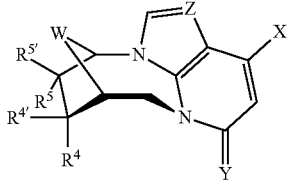

2 (C)

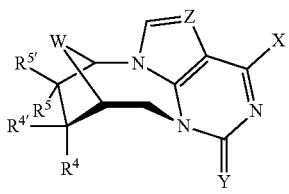

2 (D)

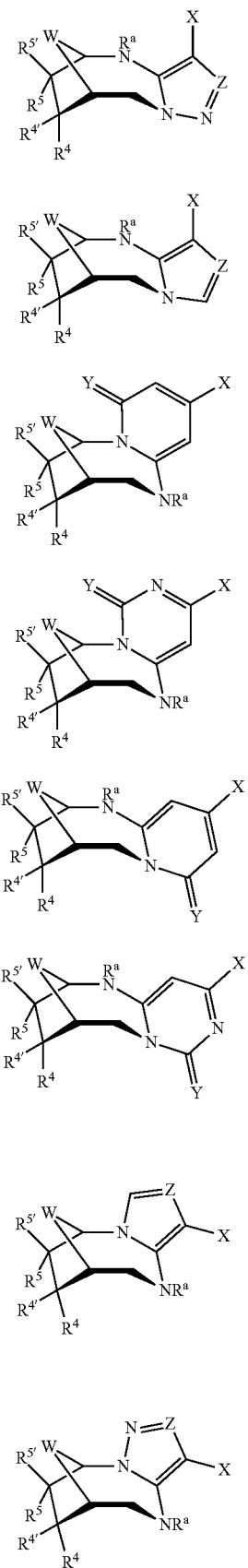
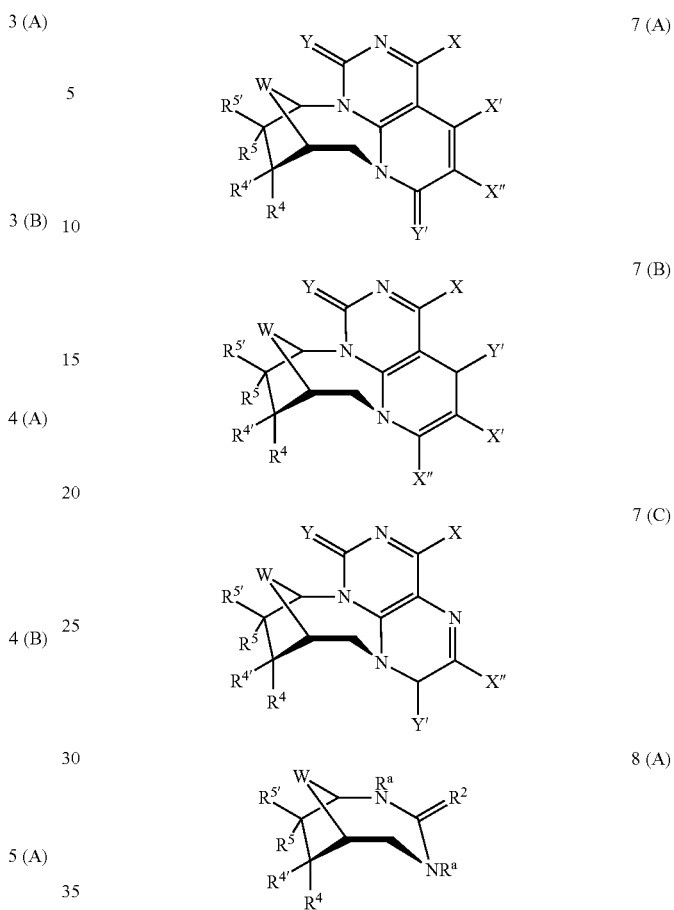

or a pharmaceutically acceptable salt or prodrug thereof, wherein W, $R^4$, $R^{4'}$, $R^5$, and $R^{5'}$ are as defined above; and Z is CH, CX, or N;

each X, X', and X" is independently hydrogen, halogen (F, Cl, Br, or I), $NH_2$, $NHR^c$, $NR^cR^{c'}$, NHOR$^c$, $NR^cNR^{c'}R^{c''}$, OH, OR$^c$, SH, or SR$^c$;

each Y and Y' is independently O, S, NH, NR$^c$, NOR$^c$, or Se;

each $R^a$ is independently hydrogen, lower alkyl, alkylene, alkenyl, carbocycle, aryl, heterocycle, heteroaryl, aralkyl, aminoalkyl, aminoaryl, or aminoacyl of $C_1$-$C_6$; and each R$^c$, R$^{c'}$, and R$^{c''}$ independently is hydrogen, lower alkyl, lower alkenyl, aryl, or arylalkyl such as unsubstituted or substituted phenyl or benzyl, cycloalkyl, or cyclopropyl.

One particular example of a nucleoside derivative is the following bicyclo[4.2.1]nonane of the following formula.

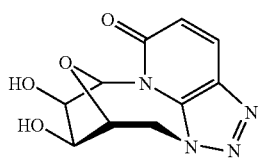

In another embodiment, the present invention provides compounds of the general formula

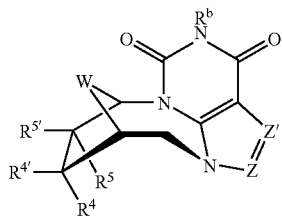

or a pharmaceutically acceptable salt or prodrug thereof, wherein W, $R^4$, $R^{4'}$, $R^5$, and $R^{5'}$ are as defined above;
$R^b$ is $R^c$, $OR^c$, $NH_2$, $NHR^c$, or $NR^cR^{c'}$, wherein $R^c$ and $R^{c'}$ are as defined above; and
each Z and Z' is independently CH, CX, or N.

In a particular embodiment, the bicyclo[4.2.1]nonane is of the formula:

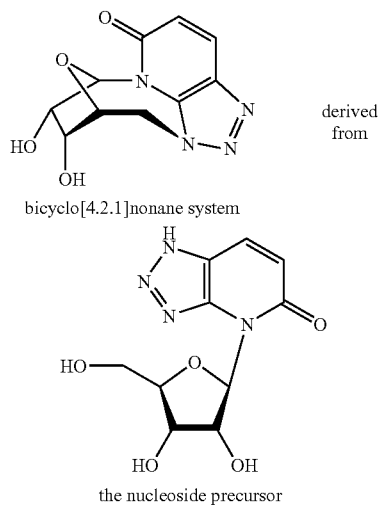

or a pharmaceutically acceptable salt or prodrug thereof.

Therefore, in one embodiment, the present invention provides a bicyclo[4.2.1]nonane ring of the formula (I), or a pharmaceutically acceptable salt and/or prodrug for the treatment and/or prophylaxis of a host, such as a human, with a Flaviviridae infection, and in particular a HCV infection.

In another embodiment of the invention, a pharmaceutical composition that includes a compound of formula (I), or a pharmaceutically acceptable salt or prodrug thereof, together with a pharmaceutically acceptable carrier or diluent is provided.

In yet another embodiment of the invention, a pharmaceutical composition with a compound of formula (I), or a pharmaceutically acceptable salt or prodrug thereof, optionally with a pharmaceutically acceptable carrier or diluent, in combination with one or more other antiviral agents are provided.

The invention also includes a method for the treatment and/or prophylaxis of a Flaviviridae infection, including a HCV infection, comprising the administration of an antivirally effective amount of a bicyclo[4.2.1]nonane ring of formula (I), or a pharmaceutically acceptable salt or prodrug thereof, optionally with a pharmaceutically acceptable carrier or diluent.

The invention further includes a method for the treatment and/or prophylaxis of a Flaviviridae infection, including a HCV infection, comprising the administration of an antivirally effective amount of a bicyclo[4.2.1]nonane ring of formula (I), or a pharmaceutically acceptable salt or prodrug thereof, optionally with a pharmaceutically acceptable carrier or diluent, in combination and/or alternation with one or more other antivirally effective agents.

In yet another embodiment, a method of manufacture of a medicament for treatment of a Flaviviridae infection using a compound of formula (I), or a pharmaceutically acceptable salt or prodrug thereof, is provided, optionally with a pharmaceutically acceptable carrier or diluent.

In an additional embodiment, a method of treating a mammal having a virus-associated disorder which comprises administering to the mammal a pharmaceutically effective amount of a compound of formula (I), or a pharmaceutically acceptable salt or prodrug thereof, is provided.

The invention also includes the use of a compound of formula (I), as described herein, or a pharmaceutically acceptable salt or prodrug thereof, optionally with a pharmaceutically acceptable carrier or diluent, in a medical therapy, i.e. as an antiviral or antitumor/anticancer agent, for example for the treatment or prophylaxis of a Flaviviridae infection, including HCV infection.

The invention also includes the use of a compound of formula (I), as described herein, or a pharmaceutically acceptable salt or prodrug thereof, optionally with a pharmaceutically acceptable carrier or diluent, in alternation or combination with one or more other therapeutic agents in a medical therapy, i.e. as an antiviral or antitumor/anticancer agent, for example for the treatment or prophylaxis of a Flaviviridae infection, including HCV infection.

The invention further includes the use of a compound of formula (I), as described herein, or a pharmaceutically acceptable salt or prodrug thereof in the manufacture of a medicament for treatment of a Flaviviridae infection.

The invention also includes processes for the preparation of compound of formula (I), as described herein, and their pharmaceutically acceptable salts and prodrugs thereof.

DETAILED DESCRIPTION OF THE INVENTION

Figure 1:
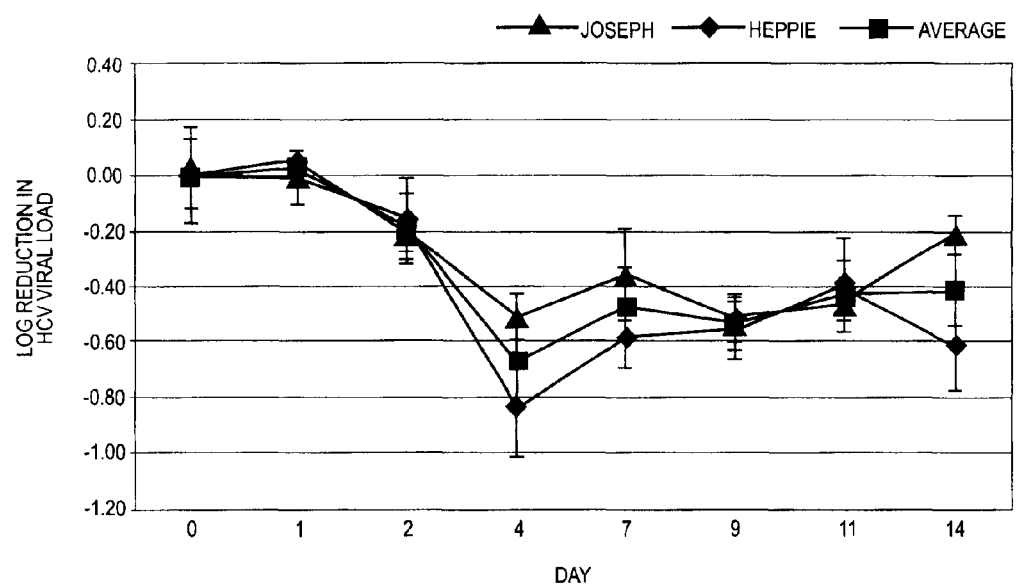
FIG. 1 is a line graph depicting the HCV viral load during oral treatment of chronically HCV-infected chimpanzees with compound 15 (Y=H, Z=CH) at 5 mg/kg/day once daily.

It was surprisingly discovered that certain bicyclo[4.2.1] nonane rings exhibit potent and selective activity against a Flaviviridae infection, and in particular against HCV.

The present invention also includes at least the following features:
(a) compounds, and their pharmaceutically acceptable salts or prodrugs thereof, useful for the treatment or prophylaxis of a Flaviviridae infection, and in particular a HCV infection;
(b) pharmaceutical compositions that include an antivirally effective amount of a compound of formula (I) or any other compound, as described herein, or a pharmaceutically acceptable salt or prodrug thereof together with a pharmaceutically acceptable carrier or diluent, according to the present invention;
(c) pharmaceutical compositions with a compound of formula (I) or any other compound, as described herein, or a pharmaceutically acceptable salt or prodrug thereof, in combination with one or more other antivirally effective agents;

(d) methods for the treatment or prophylaxis of a Flaviviridae infection, including hepatitis C infection, in a host comprising administering an effective amount of a compound of formula (I) or any other compound, as described herein, or a pharmaceutically acceptable salt or prodrug thereof, optionally in a pharmaceutically acceptable carrier or diluent;

(e) methods for the treatment or prophylaxis of a Flaviviridae infection, including hepatitis C infection, in a host comprising administering an effective amount of a compound of formula (I) or any other compound, as described herein, or a pharmaceutically acceptable salt or prodrug thereof, optionally in a pharmaceutically acceptable carrier or diluent in combination or alternation with one or more other antivirally effective agents;

(f) use of a compound of formula (I) or any other compound, as described herein, or a pharmaceutically acceptable salt or prodrug thereof, optionally in a pharmaceutically acceptable carrier, for the treatment or prophylaxis of a Flaviviridae infection, and in particular a HCV infection;

(g) use of a compound of formula (I) or any other compound, as described herein, or a pharmaceutically acceptable salt or prodrug thereof, optionally in a pharmaceutically acceptable carrier, in alternation or combination with one or more other antivirally effective agents for the treatment or prophylaxis of a Flaviviridae infection, and in particular a HCV infection;

(h) use of a compound of formula (I) or any other compound, as described herein, or a pharmaceutically acceptable salt or prodrug thereof in the manufacture of a medicament for treatment of a Flaviviridae infection;

(i) use of a compound of formula (I) or any other compound, as described herein, or a pharmaceutically acceptable salt or prodrug thereof, optionally in a pharmaceutically acceptable carrier or diluent in a medical therapy, i.e. as an antiviral or antitumor/anticancer agent, for example for the treatment or prophylaxis of a Flaviviridae infection, including HCV infection; and (j) processes for the preparation of compound of formula (I) or any other compound, as described herein, and their pharmaceutically acceptable salts and prodrugs thereof.

Active Compound

In one embodiment of this invention, the present invention provides a compound of the general formula (I):

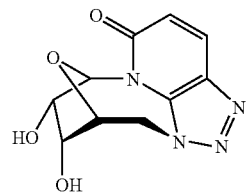

(I)

or a pharmaceutically acceptable salt or prodrug thereof, wherein:

(a) each $R^4$ and $R^{4'}$ is independently hydrogen, halogen (F, Br, Cl, or I), pseudohalogen, CN, $NO_2$, lower alkyl of $C_1$-$C_6$, halogenated lower alkyl, hydroxyl, alkoxy, $CH_2OH$, $CH_2OR^6$, $NH_2$, $NR^6R^7$, or a residue of an amino acid; wherein at least one of $R^4$ and $R^{4'}$ is hydrogen;

(b) each $R^5$ and $R^{5'}$ is independently hydrogen, halogen (F, Br, Cl, or I), pseudohalogen, CN, $NO_2$, lower alkyl of $C_1$-$C_6$, halogenated lower alkyl, hydroxyl, alkoxy, $CH_2OH$, $CH_2OR^6$, $NH_2$, $NR^6R^7$, or a residue of an amino acid; wherein at least one of $R^5$ and $R^{5'}$ is hydrogen;

(c) each $R^6$ and $R^7$ is independently hydrogen, alkyl, halogenated alkyl, alkylene, alkenyl, carbocycle, aryl, heterocycle, heteroaryl, aralkyl, or acyl;

(d) $R^1$ is hydrogen, lower alkyl, alkylene, alkenyl, carbocycle, aryl, heterocycle, heteroaryl, aralkyl, aminoalkyl, aminoaryl, or aminoacyl of $C_1$-$C_6$;

(e) $R^2$ is oxygen, sulfur, NR', or $CR'_2$, wherein each R' is independently hydrogen, lower alkyl, alkylene, alkenyl, aryl, or aralkyl of $C_1$-$C_6$;

(f) $R^3$ is hydrogen, lower alkyl, alkylene, alkenyl, carbocycle, aryl, heterocycle, heteroaryl, aralkyl, aminoalkyl, aminoaryl, or aminoacyl of $C_1$-$C_6$;

(g) alternatively if $R^2$ is NR', then $R^1$ or $R^3$ can come together with NR' to form a substituted or unsubstituted 5-7 membered ring that can include one or more heteroatoms; or (h) if $R^2$ is $CR'_2$, then $R^1$ or $R^3$ can come together with $CR'_2$ to form a substituted or unsubstituted 5-7 membered ring that can include one or more heteroatoms; or (i) if $R^2$ is $CR'_2$, then $R^1$ and $R^3$ can come together with $CR'_2$ to form a substituted or unsubstituted bicyclic ring that can include one or more heteroatoms; and (j) W is O or $CH_2$ In a particular embodiment, the bicyclo[4.2.1]nonane is of the formula:

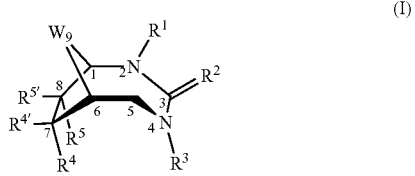

or a pharmaceutically acceptable salt or prodrug thereof.

In a preferred embodiment, the $R^5$ or $R^{5'}$ of the bicyclo[4.2.1]nonane is a residue of an amino acid, i.e. a 2'-prodrug of an active bicyclo[4.2.1]nonane wherein $R^5$ or $R^{5'}$ is OH. In one embodiment, the amino acid is valine. In a particular sub-embodiment, the amino acid is L-valine.

In a first principal sub-embodiment of the present invention, a compound of formula (I) is provided in which $R^2$ is $CR'_2$, $R^1$ and $R^2$ come together to form a six-membered ring and $R^3$ and $R^2$ come together to form a five-membered ring (to form a five-six fused bicyclic ring system).

In a second principal sub-embodiment of the present invention, a compound of formula (I) is provided in which $R^2$ is $CR'_2$, $R^1$ and $R^2$ come together to form a five-membered ring and $R^3$ and $R^2$ come together to form a six-membered ring (to form a five-six fused bicyclic ring system).

In a third principal sub-embodiment of the present invention, a compound of formula (I) is provided in which $R^2$ is $CR'_2$, and $R^3$ and $R^2$ come together to form a five-membered ring. In one embodiment, $R^1$ and $R^2$ do not come together to form a ring.

In a fourth principal sub-embodiment of the present invention, a compound of formula (I) is provided in which $R^2$ is $CR'_2$, and $R^1$ and $R^2$ come together to form a six-membered ring. In one embodiment, $R^3$ and $R^2$ do not come together to form a ring.

In a fifth principal sub-embodiment of the present invention, a compound of formula (I) is provided in which $R^2$ is $CR'_2$, and $R^3$ and $R^2$ come together to form a six-membered ring. In one embodiment, $R^1$ and $R^2$ do not come together to form a ring.

In a sixth principal sub-embodiment of the present invention, a compound of formula (I) is provided in which $R^2$ is $CR'_2$, and $R^1$ and $R^2$ come together to form a five-membered ring. In one embodiment, $R^3$ and $R^2$ do not come together to form a ring.

In a seventh principal sub-embodiment of the present invention, a compound of formula (I) is provided in which $R^2$ is $CR'_2$, $R^1$ and $R^2$ come together to form a six-membered ring and $R^3$ and $R^2$ come together to form a six-membered ring (to form a six-six fused bicyclic ring system).

In an eighth principal sub-embodiment of the present invention, a compound of formula (I) is provided in which neither $R^1$ and $R^2$ nor $R^3$ and $R^2$ come together to form a ring.

In another particular embodiment, the bicyclo[4.2.1]nonane is of the formula:

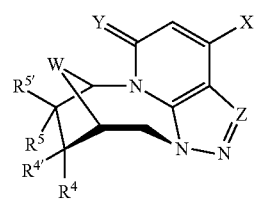
1 (A)

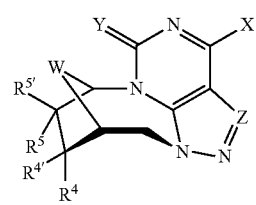
1 (B)

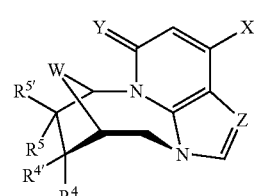
1 (C)

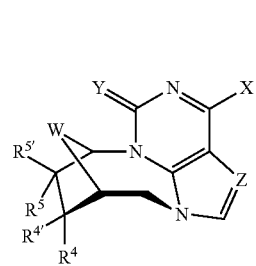
1 (D)

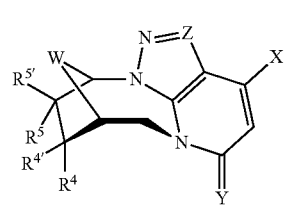
2 (A)

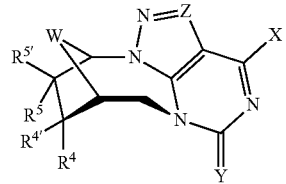
2 (B)

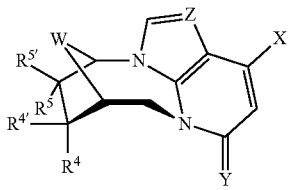
2 (C)

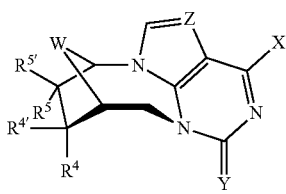
2 (D)

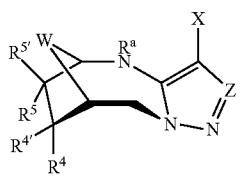
3 (A)

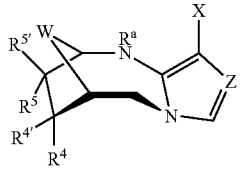
3 (B)

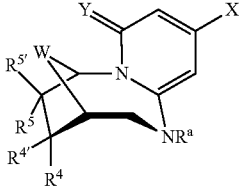
4 (A)

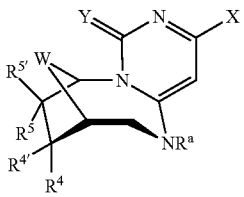
4 (B)

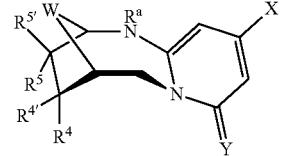
5 (A)

-continued
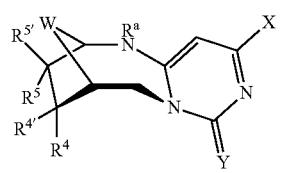
5 (B)
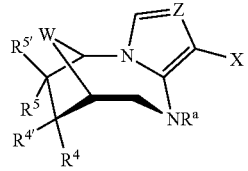
6 (A)
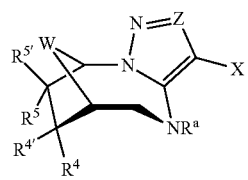
6 (B)
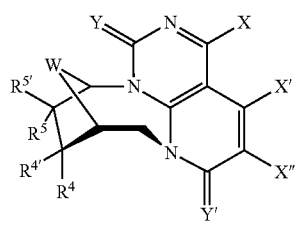
7 (A)
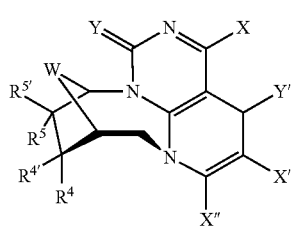
7 (B)
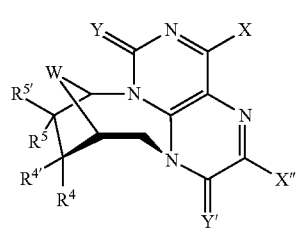
7 (C)
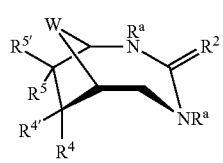
8 (A)
or a pharmaceutically acceptable salt or prodrug thereof, wherein $R^2$, $R^a$, X, X', X", Y, Y', W, Z, $R^4$, $R^{4'}$, $R^5$, and $R^{5'}$ are as defined above.
In another particular embodiment, the bicyclo[4.2.1]nonane is of the formula:
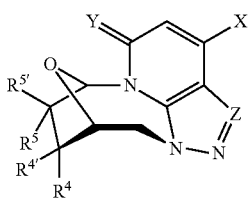
1 (E)
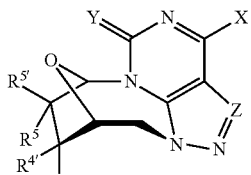
1 (F)
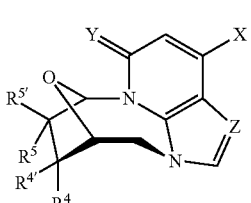
1 (G)
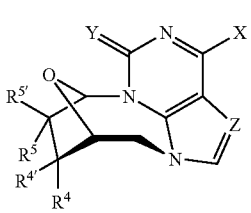
1 (H)
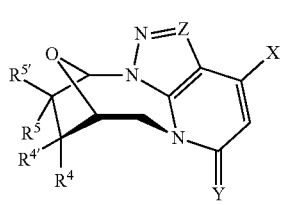
2 (E)
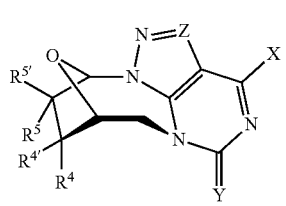
2 (F)
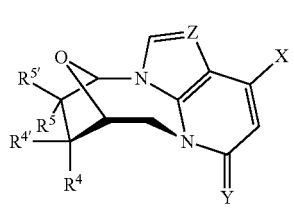
2 (G)

-continued
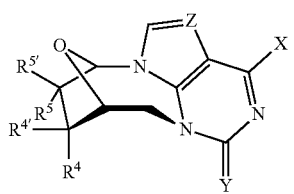
2 (H)
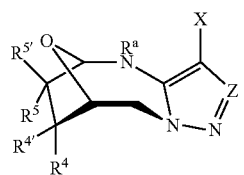
3 (C)
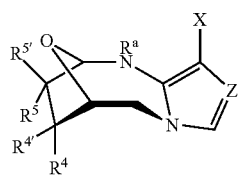
3 (D)
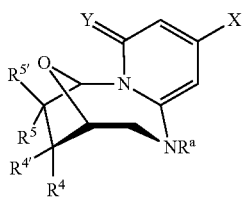
4 (C)
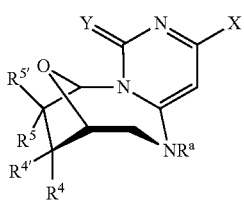
4 (D)
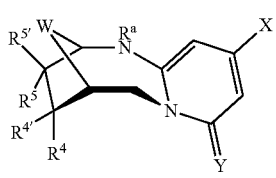
5 (C)
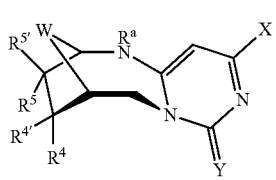
5 (D)
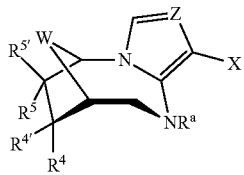
6 (C)
-continued
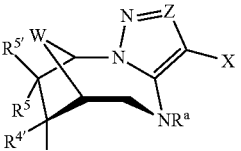
6 (D)
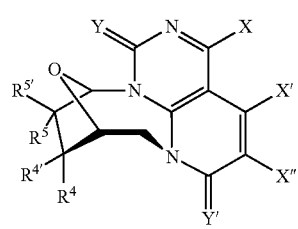
7 (D)
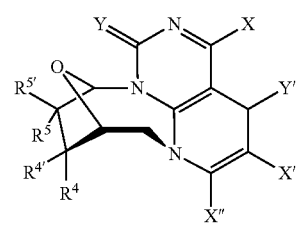
7 (E)
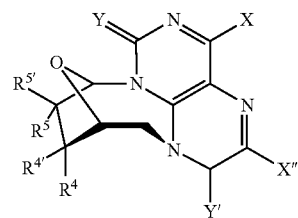
7 (F)
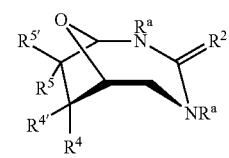
8 (B)
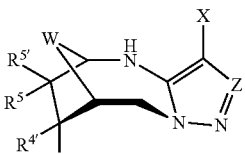
3 (E)
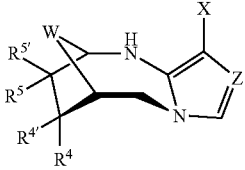
3 (F)
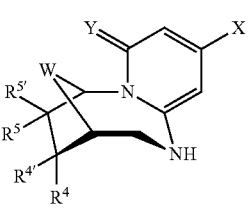
4 (E)

21
-continued
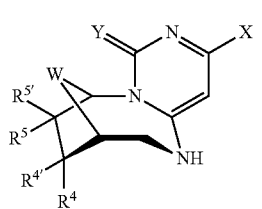
4 (F)
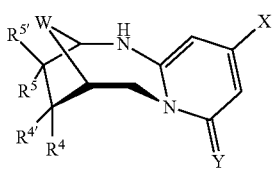
5 (E)
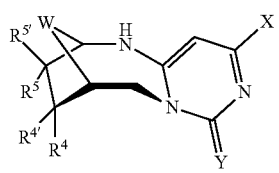
5 (F)
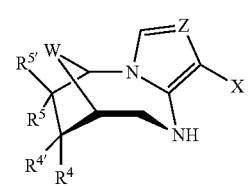
6 (E)
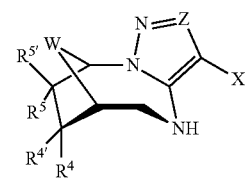
6 (F)
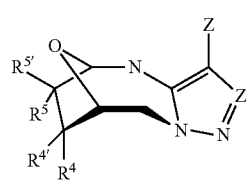
3 (G)
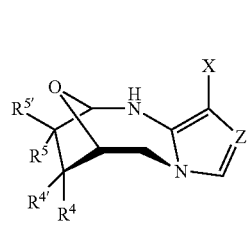
3 (H)
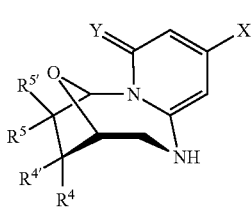
4 (G)
22
-continued
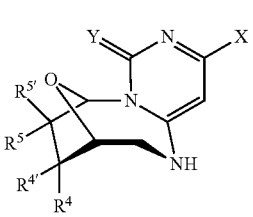
4 (H)
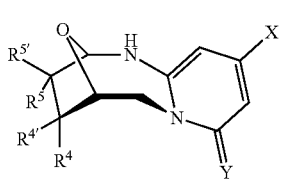
5 (G)
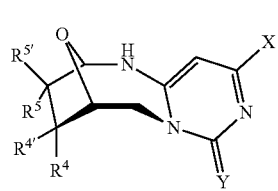
5 (H)
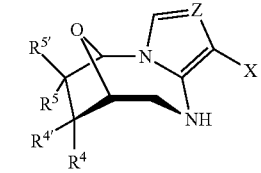
6 (G)
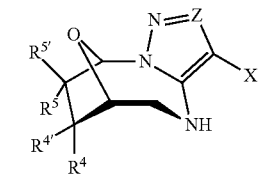
6 (H)
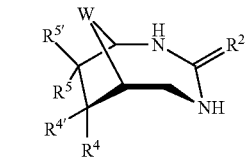
8 (C)
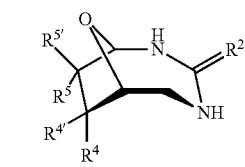
8 (D)
or a pharmaceutically acceptable salt or prodrug thereof, wherein $R^2$, $R^a$, $X$, $X'$, $X''$, $Y$, $Y'$, $W$, $Z$, $R^4$, $R^{4'}$, $R^5$, and $R^{5'}$ are as defined above.

In yet another particular embodiment, the bicyclo[4.2.1]nonane is of the formula:
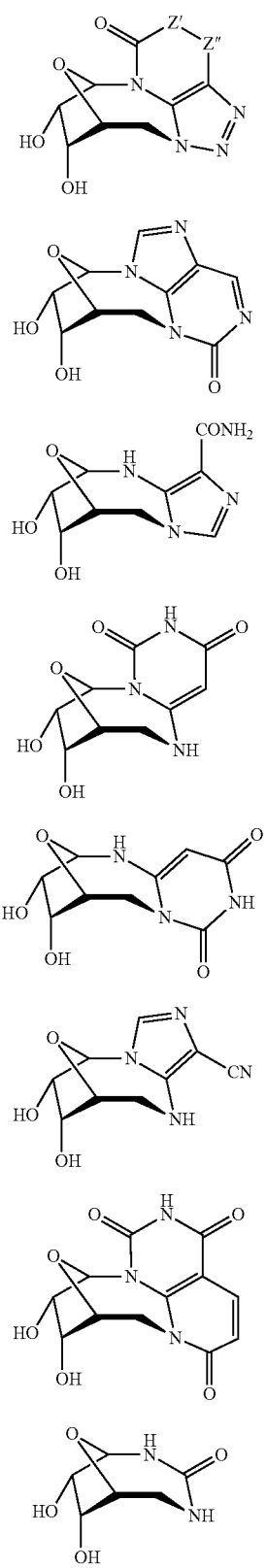
or a pharmaceutically acceptable salt or prodrug thereof, wherein each Z' and Z" is independently CH, CX, or N.
In particular embodiments of the present invention, the following compounds are provided:
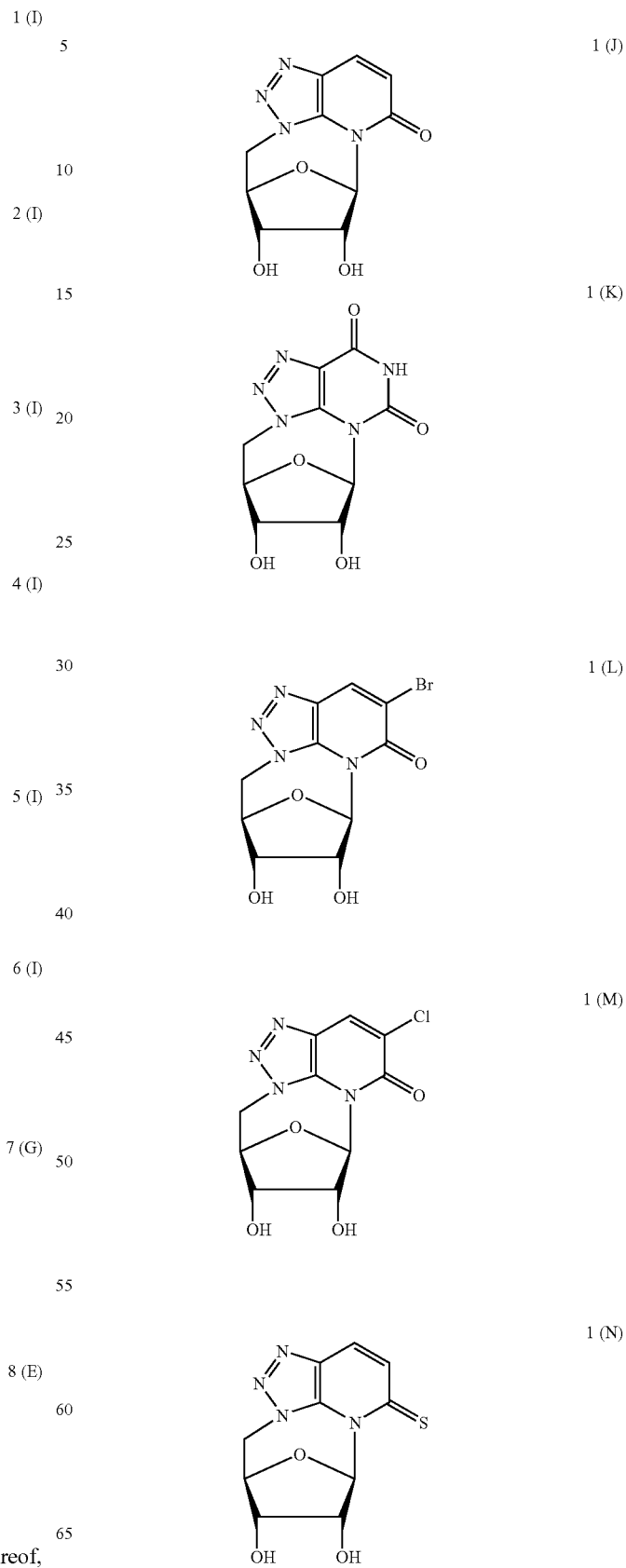

25
-continued
1 (O)
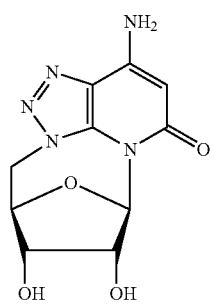
1 (P)
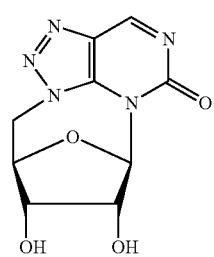
1 (Q)
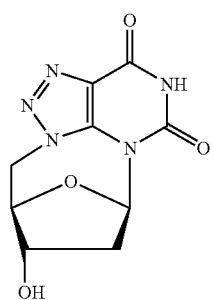
1 (R)
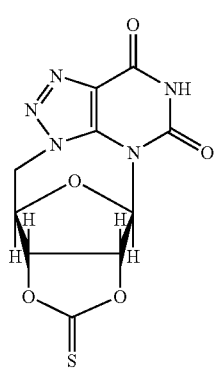
1 (S)
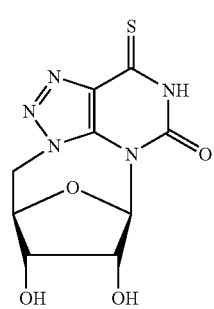
26
-continued
1 (T)
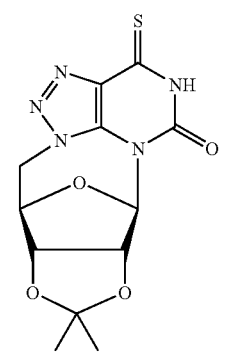
1 (U)
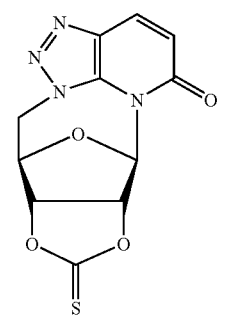
1 (V)
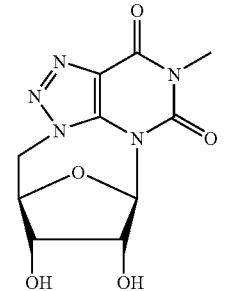
1 (W)
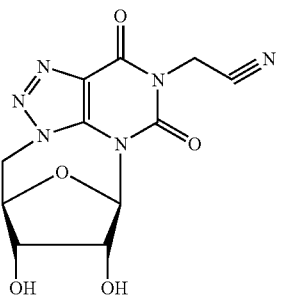
1 (X)
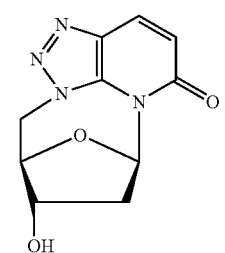

1 (Y)

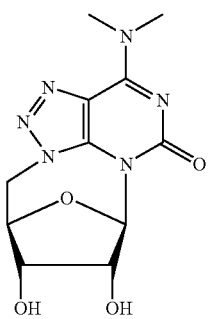

1 (Z)

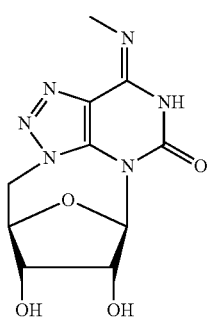

1 (AA)

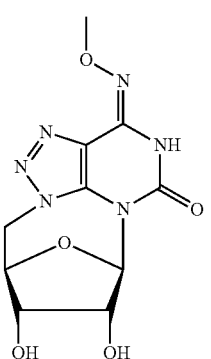

1 (AB)

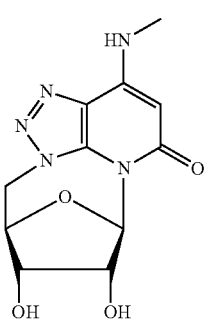

1 (AC)

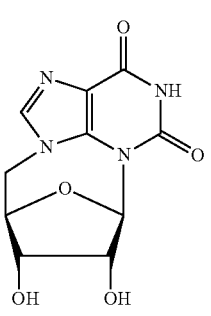

1 (AD)

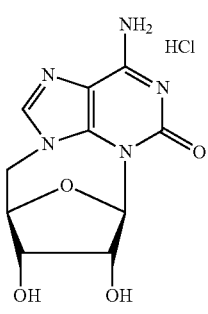

1 (AE)

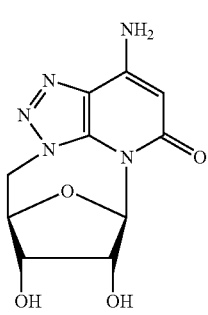

1 (AF)

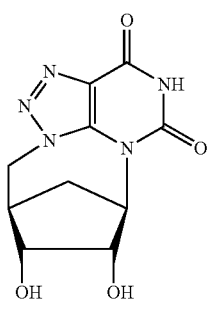

or a pharmaceutically acceptable salt or prodrug thereof.

Stereochemistry

As shown below, a compound of structure (I) can be viewed as a derivative of ribofuranose in which the C1 and C5 positions are bridged by an N—C—N fragment.

The first compound we obtained (FIG. 1, vide supra) can be viewed as 9,5'-cyclo-3-(β-D-ribofuranosyl)-1-deaza-8-azapurine-2-one which contains at least two critical chiral carbon atoms: the specified base (referred to as the C1 substituent when using the sugar ring numbering) and —CH$_2$— (referred to as the C4 substituent). When C1 and C4 substituents are cis, the nucleoside is referred to as β, and when they are trans it is α. When orienting the sugar moiety in a horizontal plane such that the —O— in the ring is in the back and the C4-CH$_2$— substituent is "up" and on the left side, the confirmation is D and its mirror image is L. Thus, when C1 and C4 substituents are cis on a D-sugar, the nucleoside is referred to as β-D and its mirror image is β-L. In this present invention, the nucleoside has to have the β-configuration.

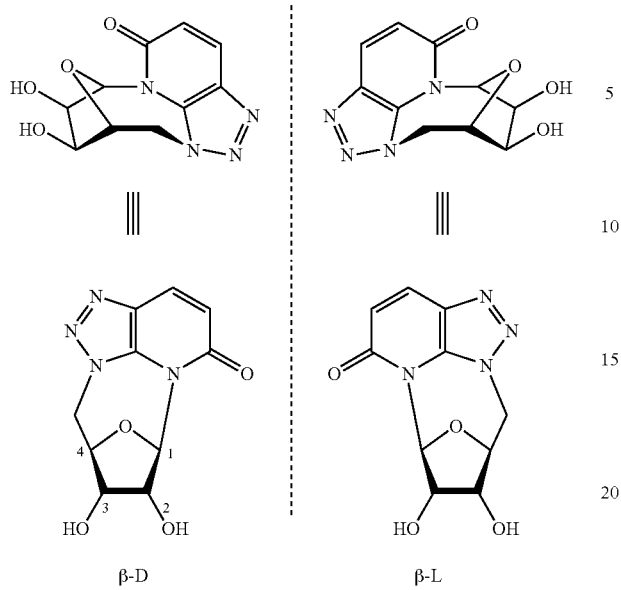

β-D                    β-L

The nucleosides formed from these coupling reactions may have asymmetric centers and occur as racemates, racemic mixtures, individual diastereomers, or enantiomers, with all isomeric forms being included in the present invention. Nucleosides having a chiral center may exist in and be isolated in optically active and racemic forms. Some compounds may exhibit polymorphism. The nucleosides formed from the coupling reaction can encompass racemic, optically-active, polymorphic, or stereoisomeric forms, or mixtures thereof, which possess the useful properties described herein. The optically active forms can be prepared by, for example, resolution of the racemic form by recrystallization techniques, by synthesis from optically-active starting materials, by chiral synthesis, by chromatographic separation using a chiral stationary phase, or by enzymatic resolution.

Optically active forms of the compounds can be prepared using any method known in the art, including by resolution of the racemic form by recrystallization techniques, by synthesis from optically-active starting materials, by chiral synthesis, or by chromatographic separation using a chiral stationary phase.

Examples of methods to obtain optically active materials include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase (including via chiral HPLC). The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

Chiral chromatography, including simulated moving bed chromatography, is used in one embodiment. A wide variety of chiral stationary phases are commercially available.

DEFINITIONS

The term "alkyl," as used herein, unless otherwise specified, refers to a saturated straight, branched, or cyclic, primary, secondary, or tertiary hydrocarbon, including but not limited to those of $C_1$ to $C_{16}$, and specifically includes methyl, $CF_3$, $CCl_3$, $CFCl_2$, $CF_2Cl$, ethyl, $CH_2CF_3$, $CF_2CF_3$, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. When the terms $C_{1-N}$ (alkyl, alkenyl, alkynyl, etc.) or the like are used in the text, it is intended to refer specifically to each compound that falls within the referenced class. As an illustrative example, $C_{1-N}$ alkyl includes individually every alkyl moiety with one to N carbon atoms, including those set out in this definition of alkyl. The alkyl group can be optionally substituted with one or more moieties selected from the group consisting of alkyl, halo (F, Cl, Br, or I), haloalkyl, hydroxyl, carboxyl, acyl, acyloxy, amino, amido, carboxyl derivatives, alkylamino, dialkylamino, arylamino, alkoxy, aryloxy, nitro, cyano, azido, thiol, imine, sulfonic acid, sulfate, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrazine, carbamate, phosphonic acid, phosphate, phosphonate, or any other viable functional group that does not inhibit the pharmacological activity of this compound, either unprotected or protected as necessary, as known to those skilled in the art, for example, as taught in Greene et al., *Protective Groups in Organic Synthesis*, John Wiley & Sons, Second Edition, 1991, hereby incorporated by reference.

The term "lower alkyl," as used herein, and unless otherwise specified, refers to a $C_1$ to $C_4$ saturated straight, branched, or if appropriate, cyclic (for example, cyclopropyl) alkyl group, including both substituted and unsubstituted forms.

The term "alkylene" or "alkenyl" refers to a saturated hydrocarbyldiyl radical of straight or branched configuration, including but not limited to those that have from one to ten carbon atoms. Included within the scope of this term are methylene, 1,2-ethane-diyl, 1,1-ethane-diyl, 1,3-propane-diyl, 1,2-propane-diyl, 1,3-butane-diyl, 1,4-butane-diyl, and the like. The alkylene group or other divalent moiety disclosed herein can be optionally substituted with one or more moieties selected from the group consisting of alkyl, halo, haloalkyl, hydroxyl, carboxyl, acyl, acyloxy, amino, amido, carboxyl derivatives, alkylamino, azido, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrazine, carbamate, phosphonic acid, phosphonate, or any other viable functional group that does not inhibit the pharmacological activity of this compound, either unprotected or protected as necessary, as known to those skilled in the art, for example, as taught in Greene et al., *Protective Groups in Organic Synthesis*, John Wiley & Sons, Second Edition, 1991, hereby incorporated by reference.

The term "aryl", alone or in combination, means a carbocyclic aromatic system containing one, two, or three rings wherein such rings may be attached together in a pendent manner or may be fused.

The "aryl" group can be optionally substituted with one or more of the moieties selected from the group consisting of alkyl, alkenyl, alkynyl, heteroaryl, heterocyclic, carbocycle, alkoxy, oxo, aryloxy, arylalkoxy, cycloalkyl, tetrazolyl, heteroaryloxy; heteroarylalkoxy, carbohydrate, amino acid, amino acid esters, amino acid amides, alditol, halogen, haloalkylthio, haloalkoxy, haloalkyl, hydroxyl, carboxyl, acyl, acyloxy, amino, aminoalkyl, aminoacyl, amido, alkylamino, dialkylamino, arylamino, nitro, cyano, thiol, imide, sulfonic acid, sulfate, sulfonate, sulfonyl, alkylsulfonyl, aminosulfonyl, alkylsulfonylamino, haloalkylsulfonyl, sulfanyl, sulfinyl, sulfamoyl, carboxylic ester, carboxylic acid, amide, phosphonyl, phosphinyl, phosphoryl, thioester, thioether, oxime, hydrazine, carbamate, phosphonic acid, phosphate, phosphonate, phosphinate, sulfonamido, carboxamido, hydroxamic acid, sulfonylimide, or any other desired functional group that does not inhibit the pharmacological activity of this compound, either unprotected or protected as necessary, as known to those skilled in the art, for example, as taught in Greene et al., "Protective Groups in Organic Synthesis," John Wiley and Sons, Second Edition, 1991. In addition, adjacent groups on an "aryl" ring may combine to form a 5- to 7-membered saturated or partially unsaturated carbocyclic, aryl, heteroaryl, or heterocyclic ring, which in turn may be substituted as above.

The heteroaryl ring may optionally be substituted by one or more substituent listed as optional substituents for aryl. In addition, adjacent groups on the heteroaryl or heterocyclic ring may combine to form a 5- to 7-membered carbocyclic, aryl, heteroaryl, or heterocyclic ring, which in turn may be substituted as above. Nonlimiting examples of heterocyclics and heteroaromatics are pyrrolidinyl, tetrahydrofuryl, tetrahydrofuranyl, pyranyl, purinyl, tetrahydropyranyl, piperazinyl, piperidinyl, morpholino, thiomorpholino, tetrahydropyranyl, imidazolyl, pyrrolinyl, pyrazolinyl, indolinyl, dioxolanyl, or 1,4-dioxanyl, aziridinyl, furyl, furanyl, pyridyl, pyridinyl, pyridazinyl, pyrimidinyl, benzoxazolyl, 1,2,4-oxadiazolyl, 1,3,4-oxadiazolyl, 1,3,4-thiadiazole, indazolyl, triazinyl, 1,3,5-triazinyl, thienyl, isothiazolyl, tetrazolyl, pyrazinyl, benzofuranyl, quinolyl, isoquinolyl, benzothienyl, isobenzofuryl, pyrazolyl, indolyl, isoindolyl, benzimidazolyl, carbazolyl, oxazolyl, thiazolyl, benzothiazolyl, isothiazolyl, 1,2,4-thiadiazolyl, isooxazolyl, 1,2,4-oxadiazolyl, 1,3,4-oxadiazolyl, pyrrolyl, quinazolinyl, quinoxalinyl, benzoxazolyl, quinolinyl, isoquinolinyl, cinnolinyl, phthalazinyl, xanthinyl, hypoxanthinyl, pyrazole, imidazole, 1,2,3-triazole, 1,2,4-triazole, 1,2,3-oxadiazole, thiazine, pyridazine, triazolopyridinyl, or pteridinyl wherein said heteroaryl or heterocyclic group can be optionally substituted with one or more substituent selected from the same substituents as set out above for aryl groups. Functional oxygen and nitrogen groups on the heteroaryl group can be protected as necessary or desired. Suitable protecting groups can include trimethylsilyl, dimethylhexylsilyl, t-butyldimethylsilyl, t-butyldiphenylsilyl, trityl or substituted trityl, alkyl groups, acyl groups such as acetyl and propionyl, methanesulfonyl, and p-toluenesulfonyl.

The term "aralkyl," as used herein, and unless otherwise specified, refers to an aryl group as defined above linked to the molecule through an alkyl group as defined above. The term "alkaryl" or "alkylaryl" as used herein, and unless otherwise specified, refers to an alkyl group as defined above linked to the molecule through an aryl group as defined above. In each of these groups, the alkyl group can be optionally substituted as describe above and the aryl group can be optionally substituted with one or more moieties selected from the group consisting of alkyl, halo, haloalkyl, hydroxyl, carboxyl, acyl, acyloxy, amino, amido, azido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrazine, carbamate, phosphonic acid, phosphonate, or any other viable functional group that does not inhibit the pharmacological activity of this compound, either unprotected or protected as necessary, as known to those skilled in the art, for example, as taught in Greene et al., *Protective Groups in Organic Synthesis*, John Wiley & Sons, Second Edition, 1991, hereby incorporated by reference. Specifically included within the scope of the term aryl are phenyl; naphthyl; phenylmethyl; phenylethyl; 3,4,5-trihydroxyphenyl; 3,4,5-trimethoxyphenyl; 3,4,5-triethoxyphenyl; 4-chlorophenyl; 4-methylphenyl; 3,5-di-tertiarybutyl-4-hydroxyphenyl; 4-fluorophenyl; 4-chloro-1-naphthyl; 2-methyl-1-naphthylmethyl; 2-naphthylmethyl; 4-chlorophenylmethyl; 4-t-butylphenyl; 4-t-butylphenylmethyl, and the like.

The term "alkylamino" or "arylamino" refers to an amino group that has one or two alkyl or aryl substituents, respectively.

The term "halogen," as used herein, includes fluorine, chlorine, bromine, and iodine.

The term "pseudohalogen" as used herein includes azides, cyanides, isocyanates, and isothiocyanates.

The term "amino acid" includes naturally occurring and synthetic α, β, γ, or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine, and histidine. In a preferred embodiment, the amino acid is in the L-configuration. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl, or β-histidinyl.

The term "host," as used herein, refers to a unicellular or multicellular organism in which the virus can replicate, including cell lines and animals, and preferably a human. Alternatively, the host can be carrying a part of the Flaviviridae viral genome, whose replication or function can be altered by the compounds of the present invention. The term host specifically refers to infected cells, cells transfected with all or part of the Flaviviridae genome and animals, in particular, primates (including chimpanzees) and humans. In most animal applications of the present invention, the host is a human patient. Veterinary applications, in certain indications, however, are clearly anticipated by the present invention (such as chimpanzees).

Pharmaceutically Acceptable Salts and Prodrugs

The terms "pharmaceutically acceptable salt" or "pharmaceutically acceptable prodrug" are used throughout the specification to describe any pharmaceutically acceptable form (such as an ester, phosphate ester, or salt of an ester or a related group) of a nucleoside compound which, upon administration to a patient, provides the nucleoside compound. Pharmaceutically acceptable salts include those derived from pharmaceutically acceptable inorganic or organic bases and acids. Suitable salts include those derived from alkali metals such as potassium and sodium and alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. The compounds of this invention possess antiviral activity against a Flaviviridae infection, or are metabolized to a compound that exhibits such activity.

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium, or lithium) or alkaline earth metal (for example, calcium) salts of carboxylic acids can also be made.

Any of the compounds described herein can be administered as a prodrug to increase the activity, bioavailability, stability, or otherwise alter the properties of the compound. A number of prodrug ligands are known. In general, alkylation, acylation, or other lipophilic modification of the free hydroxyls or amines of the compound can increase the stability of the compound. Examples of substituent groups that can replace one or more hydrogen on the hydroxyl or amine moiety are alkyl, aryl, steroids, carbohydrates, including sugars, 1,2-diacylglycerol, and alcohols. Many are described in R. Jones and N. Bischofberger, *Antiviral Research*, 27 (1995) 1-17. Any of these can be used in combination with the disclosed compounds to achieve a desired effect.

The active compounds can also be provided as a C(7) or C(8)-phosphoether lipid or a C(7) or C(8) ether lipid. Non-limiting examples of U.S. patents that disclose suitable lipophilic substituents that can be covalently incorporated into the compound or lipophilic preparations, include U.S. Pat. Nos. 5,149,794 (Sep. 22, 1992, Yatvin et al.); 5,194,654 (Mar. 16, 1993, Hostetler et al.); 5,223,263 (Jun. 29, 1993, Hostetler et al.); 5,256,641 (Oct. 26, 1993, Yatvin et al.); 5,411,947 (May 2, 1995, Hostetler et al.); 5,463,092 (Oct. 31, 1995, Hostetler et al.); 5,543,389 (Aug. 6, 1996, Yatvin et al.); 5,543,390 (Aug. 6, 1996, Yatvin et al.); 5,543,391 (Aug. 6, 1996, Yatvin et al); and 5,554,728 (Sep. 10, 1996; Basava et al.), all of which are incorporated herein by reference. Foreign patent applications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721. The compounds can also be provided as "SATE" derivatives.

Alternatively, the bicyclo[4.2.1]nonane can also be provided as a C(7) or C(8)-alkyl esters or amino acid esters, including biologically cleavable moieties at C(7) (otherwise referred to as the 3' position) and/or at C(8) (otherwise referred to as the 2' position). Preferred moieties are amino acid esters including valyl and alkyl esters including acetyl. Therefore, this invention specifically includes 2'-L-amino acid esters, 3'-L-amino acid esters, and 2',3'-L-diamino acid esters of the bicyclo[4.2.1]nonane, wherein the parent drug has an $EC_{50}$ of less than 15 micromolar, and preferably less than 10 micromolar in 2.2.15 cells; 2'-(alkyl or aryl ester)-, 3'-(alkyl or aryl ester)-, or 2',3'-L-di(alkyl or aryl ester)-bicyclo[4.2.1]nonanes, wherein the parent drug has an $EC_{50}$ of less than 10 or 15 micromolar in 2.2.15 cells; and prodrugs of bicyclo[4.2.1]nonanes wherein (i) the 2' ester is an amino acid ester and the 3'-ester is an alkyl or aryl ester; (ii) both esters are amino acid esters; (iii) both esters are independently alkyl or aryl esters; and (iv) the 2' ester is independently an alkyl or aryl ester and the 3'-ester is an amino acid ester, wherein the parent drug has an $EC_{50}$ of less than 10 or 15 micromolar in 2.2.15 cells.

Combination and Alternation Therapies for the Treatment of Flaviviridae Infection It has been recognized that drug-resistant variants of Flaviviridae can emerge after prolonged treatment with an antiviral agent. Drug resistance most typically occurs by mutation of a gene that encodes for an enzyme used in viral replication. The efficacy of a drug against a Flaviviridae infection can be prolonged, augmented, or restored by administering the compound in combination or alternation with a second, and perhaps third, antiviral compound that induces a different mutation from that caused by the principle drug. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

Nonlimiting examples of antiviral agents that can be used in combination and/or alternation with the compounds disclosed herein include:

(1) Protease Inhibitors—

Non-limiting examples include substrate-based NS3 protease inhibitors (Attwood et al., Antiviral peptide derivatives, PCT WO 98/22496, 1998; Attwood et al., *Antiviral Chemistry and Chemotherapy* 1999, 10, 259-273; Attwood et al., Preparation and use of amino acid derivatives as anti-viral agents, German Patent Pub. DE 19914474; Tung et al., Inhibitors of serine proteases, particularly hepatitis C virus NS3 protease, PCT WO 98/17679), including alphaketoamides and hydrazinoureas, and inhibitors that terminate in an electrophile such as a boronic acid or phosphonate (Llinas-Brunet et al., Hepatitis C inhibitor peptide analogues, PCT WO 99/07734); non-substrate-based NS3 protease inhibitors such as 2,4,6-trihydroxy-3-nitro-benzamide derivatives (Sudo K. et al., *Biochemical and Biophysical Research Communications*, 1997, 238, 643-647; Sudo K. et al., *Antiviral Chemistry and Chemotherapy*, 1998, 9, 186), including RD3-4082 and RD3-4078, the former substituted on the amide with a 14 carbon chain and the latter possessing a para-phenoxyphenyl group; and Sch 68631, a phenanthrenequinone, an HCV protease inhibitor (Chu M. et al., *Tetrahedron Letters* 37:7229-7232, 1996).

Sch 351633, isolated from the fungus *Penicillium griseofulvum*, was identified as a protease inhibitor (Chu M. et al., *Bioorganic and Medicinal Chemistry Letters* 9:1949-1952). Eglin c, isolated from leech, is a potent inhibitor of several serine proteases such as *S. griseus* proteases A and B, α-chymotrypsin, chymase and subtilisin. Qasim M. A. et al., *Biochemistry* 36:1598-1607, 1997.

U.S. patents disclosing protease inhibitors for the treatment of HCV include, for example, U.S. Pat. No. 6,004,933 to Spruce et al., which discloses a class of cysteine protease inhibitors for inhibiting HCV endopeptidase 2; U.S. Pat. No. 5,990,276 to Zhang et al., which discloses synthetic inhibitors of hepatitis C virus NS3 protease; U.S. Pat. No. 5,538,865 to Reyes et al.; WO 02/008251 to Corvas International, Inc., and WO 02/08187 and WO 02/008256 to Schering Corporation. HCV inhibitor tripeptides are disclosed in U.S. Pat. Nos. 6,534,523, 6,410,531, and 6,420,380 to Boehringer Ingelheim and WO 02/060926 to Bristol Myers Squibb. Diaryl peptides as NS3 serine protease inhibitors of HCV are disclosed in WO 02/48172 to Schering Corporation. Imidazolidindiones as NS3 serine protease inhibitors of HCV are disclosed in WO 02/08198 to Schering Corporation and WO 02/48157 to Bristol Myers Squibb. WO 98/17679 to Vertex Pharmaceuticals and WO 02/48116 to Bristol Myers Squibb also disclose HCV protease inhibitors;

(2) Thiazolidine derivatives (non-limiting examples include those which show relevant inhibition in a reverse-phase HPLC assay with an NS3/4A fusion protein and NS5A/5B substrate (Sudo K. et al., *Antiviral Research*, 1996, 32, 9-18), especially compound RD-1-6250, possessing a fused cinnamoyl moiety substituted with a long alkyl chain, RD4 6205 and RD4 6193);

(3) Thiazolidines and benzanilides (non-limiting examples include those identified in Kakiuchi N. et al., *J. EBS Letters* 421, 217-220; Takeshita N. et al., *Analytical Biochemistry*, 1997, 247, 242-246);

(4) Phenanthrenequinone (non-limiting examples include those possessing activity against protease in a SDS-PAGE and autoradiography assay isolated from the fermentation culture broth of *Streptomyces* sp., Sch 68631 (Chu M. et al., *Tetrahedron Letters*, 1996, 37, 7229-7232), and Sch 351633, isolated from the fungus *Penicillium griseofulvum*, which demonstrates activity in a scintillation proximity assay (Chu M. et al., *Bioorganic and Medicinal Chemistry Letters* 9, 1949-1952));

(5) Helicase inhibitors (non-limiting examples include those identified in Diana G. D. et al., Compounds, compositions and methods for treatment of hepatitis C, U.S. Pat. No. 5,633,358; Diana G. D. et al., *Piperidine derivatives*, pharmaceutical compositions thereof and their use in the treatment of hepatitis C, PCT WO 97/36554);

(6) Nucleotide polymerase inhibitors and gliotoxin (non-limiting examples include those identified in Ferrari R. et al., *Journal of Virology*, 1999, 73, 1649-1654, and the natural product cerulenin (Lohmann V. et al., *Virology*, 1998, 249, 108-118));

(7) Antisense phosphorothioate oligodeoxynucleotides (S-ODN) (non-limiting examples include those which are complementary to sequence stretches in the 5' non-coding region (NCR) of the virus (Alt M. et al., *Hepatology*, 1995, 22, 707-717), or nucleotides 326-348 comprising the 3' end of the NCR and nucleotides 371-388 located in the core coding region of the HCV RNA (Alt M. et al., *Archives of Virology*, 1997, 142, 589-599; Galderisi U. et al., *Journal of Cellular Physiology*, 1999, 181, 251-257));

(8) Inhibitors of IRES-dependent translation (non-limiting examples include those identified in Ikeda N. et al., Agent for the prevention and treatment of hepatitis C, Japanese Patent Pub. JP-08268890; Kai Y. et al., Prevention and treatment of viral diseases, Japanese Patent Pub. JP-10101591);

(9) Ribozymes (non-limiting examples include nuclease-resistant ribozymes (Maccjak, D. J. et al., *Hepatology* 1999, 30, abstract 995) and those disclosed in U.S. Pat. No. 6,043,077 to Barber et al. and U.S. Pat. Nos. 5,869,253 and 5,610,054 to Draper et al.);

(10) Nucleoside Analogs—

Non-limiting examples include any of the compounds described by Idenix Pharmaceuticals in International Publication Nos. WO 01/90121 and WO 01/92282.

Other patent applications disclosing the use of certain nucleoside analogs to treat hepatitis C virus include: PCT/CA00/01316 (WO 01/32153; filed Nov. 3, 2000) and PCT/CA01/00197 (WO 01/60315; filed Feb. 19, 2001) filed by BioChem Pharma, Inc. (now Shire Biochem, Inc.); PCT/US02/01531 (WO 02/057425; filed Jan. 18, 2002) and PCT/US02/03086 (WO 02/057287; filed Jan. 18, 2002) filed by Merck & Co., Inc.; PCT/EP01/09633 (WO 02/18404; published Aug. 21, 2001) filed by Roche; and PCT Publication Nos. WO 01/79246 (filed Apr. 13, 2001), WO 02/32920 (filed Oct. 18, 2001), and WO 02/48165 by Pharmasset, Ltd.

PCT Publication No. WO 99/43691 to Emory University, entitled "2'-Fluoronucleosides" discloses the use of certain 2'-fluoronucleosides to treat HCV;

(11) Other miscellaneous compounds (including 1-aminoalkylcyclohexanes (U.S. Pat. No. 6,034,134 to Gold et al.), alkyl lipids (U.S. Pat. No. 5,922,757 to Chojkier et al.), vitamin E and other antioxidants (U.S. Pat. No. 5,922,757 to Chojkier et al.), squalene, amantadine, bile acids (U.S. Pat. No. 5,846,964 to Ozeki et al.), N-(phosphonoacetyl)-L-aspartic acid, (U.S. Pat. No. 5,830,905 to Diana et al.), benzenedicarboxamides (U.S. Pat. No. 5,633,388 to Diana et al.), polyadenylic acid derivatives (U.S. Pat. No. 5,496,546 to Wang et al.), 2',3'-dideoxyinosine (U.S. Pat. No. 5,026,687 to Yarchoan et al.), benzimidazoles (U.S. Pat. No. 5,891,874 to Colacino et al.), plant extracts (U.S. Pat. No. 5,837,257 to Tsai et al., U.S. Pat. No. 5,725,859 to Omer et al., and U.S. Pat. No. 6,056,961), and piperadines (U.S. Pat. No. 5,830,905 to Diana et al.)); and

(12) Any other compound currently in preclinical or clinical development for treatment of hepatitis C virus including: interleukin-10 by Schering-Plough, IP-501 by Interneuron, merimebodib (VX-497) by Vertex, SYMMETREL® (amantadine) by Endo Labs Solvay, HEPTAZYME® by RPI, IDN-6556 by Idun Pharma., XTL-002 by XTL., HCV/MF59 by Chiron, CIVACIR® (hepatitis C immune globulin) by NABI, levovirin by ICN/Ribapharm, viramidine by ICN/Ribapharm, ZADAXIN® (thymosin alpha-1) by Sci Clone, thymosin plus pegylated interferon by Sci Clone, CEPLENE® (histamine dihydrochloride) by Maxim, telaprevir VX 950/LY 570310 by Vertex/Eli Lilly, ISIS 14803 by Isis Pharmaceutical/Elan, IDN-6556 by Idun Pharmaceuticals, Inc., JTK 003 by AKROS Pharma, BILN-2061 by Boehringer Ingelheim, CellCept (mycophenolate mofetil) by Roche, T67, a β-tubulin inhibitor, by Tularik, a therapeutic vaccine directed to E2 by Innogenetics, FK788 by Fujisawa Healthcare, Inc., 1 dB 1016 (Siliphos, oral silybin-phosphatdylcholine phytosome), RNA replication inhibitors (e.g., VP50406) by ViroPharma/Wyeth, therapeutic vaccine by Intercell, therapeutic vaccine by Epimmune/Genencor, IRES inhibitor by Anadys, ANA 245 and ANA 246 by Anadys, immunotherapy (THERAPORE®) by Avant, protease inhibitor by Corvas/Schering, helicase inhibitor by Vertex, fusion inhibitor by Trimeris, T cell therapy by CellExSys, polymerase inhibitor by Biocryst, targeted RNA chemistry by PTC Therapeutics, Dication by Immtech, Int., protease inhibitor by Agouron, protease inhibitor by Chiron/Medivir, antisense therapy by AVI BioPharma, antisense therapy by Hybridon, hemopurifier by Aethlon Medical, therapeutic vaccine by Merix, protease inhibitor by Bristol-Myers Squibb/Axys, CHRON VACC®, a therapeutic vaccine, by Tripep, UT 231 B by United Therapeutics, protease, helicase and polymerase inhibitors by Genelabs Technologies, IRES inhibitors by Immusol, R803 by Rigel Pharmaceuticals, INFERGEN® (interferon alphacon-1) by InterMune, OMNIFERON® (natural interferon) by Viragen, ALBUFERON® (albinterferon alpha 2b) by Human Genome Sciences, REBIF® (interferon beta-1a) by Ares-Serono, omega interferon by BioMedicine, oral interferon alpha by Amarillo Biosciences, interferon gamma, interferon tau, and interferon gamma-1b by InterMune.

In one embodiment, the compounds of the invention may be employed together with at least one other antiviral agent chosen from protease inhibitors, fusion inhibitors, polymerase inhibitors, and helicase inhibitors.

In addition, compounds according to the present invention can be administered in combination or alternation with one or more anti-retrovirus, anti-HBV, anti-HCV, or anti-Herpetic agent or interferon, or anti-cancer or antibacterial agents, including other compounds of the present invention. Certain compounds according to the present invention may be effective for enhancing the biological activity of certain agents according to the present invention by reducing the metabolism, catabolism, or inactivation of other compounds and, as such, are co-administered for this intended effect.

Pharmaceutical Compositions

Pharmaceutical compositions based upon a β-D compound of formula (I) or the β-L counterpart can be prepared that include the above-described compound or its salt or prodrug in a therapeutically effective amount for treating a Flaviviridae infection, optionally in combination with a pharmaceutically acceptable additive, carrier, or excipient. A host, including humans, infected with a Flaviviridae virus, or a gene fragment thereof, can be treated by administering to the patient an effective amount of the active compound or a pharmaceutically acceptable prodrug or salt thereof in the presence of a pharmaceutically acceptable carrier or diluent. The therapeutically effective amount may vary with the infection or condition to be treated, its severity, the treatment regimen to be employed, and the pharmacokinetics of the agent used, as well as the patient treated. The active materials can be administered by any appropriate route.

In general, it is preferable to administer the pharmaceutical composition in an orally administrable form, but formulations may be administered via parenteral, intravenous, intramuscular, transdermal, buccal, subcutaneous, suppository, or topical administration, among other routes of administration. Enteric-coated oral tablets may also be used to enhance bioavailability and stability of the compounds from an oral route of administration. Intravenous and intramuscular formulations are preferably administered in sterile saline. One of ordinary skill in the art may modify the formulation within the teachings of the specification to provide numerous formulations for a particular route of administration without rendering the compositions of the present invention unstable or compromising its therapeutic activity. In particular, a modification of a desired compound to render it more soluble in water or other vehicle, for example, may be easily accomplished by routine modification (salt formulation, esterification, etc.). Administration of the active compound may range from continuous (intravenous drip) to several oral administrations per day (for example, Q.I.D., B.I.D., etc.).

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred dose of the compound for a Flaviviridae infection will be in the range from about 1 to 50 mg/kg, preferably 1 to 20 mg/kg, of body weight per day, more generally 0.1 to about 100 mg per kilogram body weight of the recipient per day or more, depending upon the compound used, the condition or infection treated, and the route of administration. The effective dosage range of the pharmaceutically acceptable salts and prodrugs can be calculated based on the weight of the parent compound to be delivered. If the salt or prodrug exhibits activity in itself, the effective dosage can be estimated as above using the weight of the salt or prodrug or by other means known to those skilled in the art. For purposes of the present invention, a prophylactically or preventively effective amount of the compositions, according to the present invention, falls within the same concentration range as set forth above for therapeutically effective amount and is usually the same as a therapeutically effective amount.

The compound is conveniently administered in unit any suitable dosage form, including but not limited to one containing 7 to 3000 mg, preferably 70 to 1400 mg of active ingredient per unit dosage form. An oral dosage of 50-1000 mg is usually convenient, including in one or multiple dosage forms of 50, 100, 200, 250, 300, 400, 500, 600, 700, 800, 900, or 1000 mg. Lower doses may be used, for example from 10-100 mg, 1-50 mg, 0.1-50 mg, 0.1-20 mg, or 0.1-10.0 mg.

Ideally the active ingredient should be administered to achieve peak plasma concentrations of the active compound of from about 0.2 to 70 µM, preferably about 1.0 to 10 µM. This may be achieved, for example, by the intravenous injection of a 0.1 to 5% solution of the active ingredient, optionally in saline, or administration as a bolus of the active ingredient.

In particularly preferred embodiments according to the present invention, the compounds and compositions are used to treat, prevent, or delay the onset of Flaviviridae infections. Preferably, to treat, prevent, or delay the onset of infection, the compositions will be administered in oral dosage form in amounts ranging from about 250 micrograms up to about 1 gram or more at least once a day, preferably, or up to four times a day. The present compounds are preferably administered orally, but may be administered parenterally, topically, or in suppository form.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents and/or adjuvant materials can be included as part of the composition.

The tablets, pills, capsules, troches, and the like can contain any of the following ingredients, or compounds of a similar nature: a binder such as microcrystalline cellulose, gum tragacanth, or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum, or the like. A syrup may contain, in addition to the active compounds, sucrose as a sweetening agent and certain preservatives, dyes and colorings, and flavors.

The compound or a pharmaceutically acceptable prodrug or salts thereof can also be mixed with other active materials that do not impair the desired action, or with materials that supplement the desired action, such as antibiotics, antifungals, anti-inflammatories, or other antivirals, including other nucleoside compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates, and agents for the adjustment of tonicity such as sodium chloride or dextrose. The parenteral preparation can be enclosed in ampoules, disposable syringes, or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation.

In certain pharmaceutical dosage forms, the prodrug form of the compound, especially including acylated (acetylated or other) and ether derivatives, phosphate esters, and various salt forms of the present compounds, is preferred. One of ordinary skill in the art will recognize how to readily modify the present compound to a prodrug form to facilitate delivery of active compound to a targeted site within the host organism or patient. The artisan also will take advantage of favorable pharmacokinetic parameters of the prodrug form, where applicable, in delivering the desired compound to a targeted site within the host organism or patient to maximize the intended effect of the compound in the treatment of Flaviviridae infection (including HCV infection).

To prepare the pharmaceutical compositions according to the present invention, a therapeutically effective amount of one or more of the compounds according to the present invention is preferably mixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs, and solutions, suitable carriers and additives including water, glycols, oils, alcohols, flavoring agents, preservatives, coloring agents, and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents, and the like may be used. If desired, the tablets or capsules may be enteric-coated for sustained release by standard techniques. The use of these dosage forms may significantly impact the bioavailability of the compounds in the patient.

For parenteral formulations, the carrier will usually comprise sterile water or aqueous sodium chloride solution, though other ingredients, including those that aid dispersion, also may be included. Where sterile water is to be used and maintained as sterile, the compositions and carriers must also be sterilized. Injectable suspensions may also be prepared, in which case appropriate liquid carriers, suspending agents, and the like may be employed.

Liposomal suspensions (including liposomes targeted to viral antigens or liposomes targeted to infected cells with monoclonal antibodies to viral antigens) may also be prepared by conventional methods to produce pharmaceutically acceptable carriers. This may be appropriate for the delivery of free nucleosides, acyl nucleosides, or phosphate ester prodrug forms of the nucleoside compounds according to the present invention. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

The compounds according to the present invention, because of their low toxicity to host cells in certain instances, may be advantageously employed prophylactically to prevent Flaviviridae infection or to prevent the occurrence of clinical symptoms associated with the viral infection. Thus, the present invention also encompasses methods for the prophylactic treatment of viral infection, and in particular Flaviviridae infection. In this aspect, according to the present invention, the present compositions are used to prevent or delay the onset of a Flaviviridae infection (including HCV). This prophylactic method comprises administration to a patient in need of such treatment, or who is at risk for the development of HCV disease, an amount of a compound according to the present invention effective for alleviating, preventing, or delaying the onset of the viral infection. In the prophylactic treatment according to the present invention, it is preferred that the antiviral compound utilized should be low in toxicity and preferably non-toxic to the patient. It is particularly preferred in this aspect of the present invention that the compound that is used should be maximally effective against the virus and should exhibit a minimum of toxicity to the patient. In the case of HCV infection, compounds according to the present invention, which may be used to treat these disease states, may be administered within the same dosage range for therapeutic treatment (i.e., about 250 micrograms up to 1 gram or more from one to four times per day for an oral dosage form) as a prophylactic agent to prevent the proliferation of a Flaviviridae infection, or alternatively, to prolong the onset of a Flaviviridae infection, which manifests itself in clinical symptoms.

Synthetic Protocol

Compounds of formula (I) in the present invention can be roughly divided into eight classes: (i) a compound of formula (I) in which both nitrogens at the $2^{nd}$ and $4^{th}$ positions are part of a bicyclic ring system and $N^2$ is a part of 6-membered ring and $N^4$ a part of 5-membered ring, such as compound 1 (A-D), (ii) a compound of formula (I) in which both nitrogens at the $2^{nd}$ and $4^{th}$ positions are part of a bicyclic ring system and $N^2$ is a part of 5-membered ring and $N^4$ a part of 6-membered ring, such as compound 2 (A-D), (iii) a compound of class (i) but lacks the 6-membered ring, such as 3 (E-F), (iv) a compound of class (i) but lacks the 5-membered ring, such as 4 (E-F), (v) a compound of class (ii) but lacks the 5-membered ring, such as 5 (E-F), (vi) a compound of class (ii) but lacks the 6-membered ring, such as 6 (E-F), and (vii) a compound in which both $2^{nd}$ and $4^{th}$ nitrogens are parts of other bicyclic ring, such as 7 (A-C). Finally (viii) a compound in which both $2^{nd}$ and $4^{th}$ nitrogens are not parts of another ring, such as 8 (C).

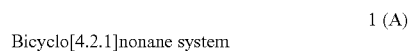

Bicyclo[4.2.1]nonane system

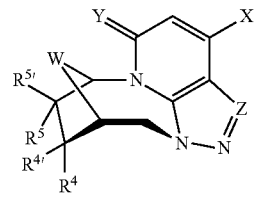

1 (A)

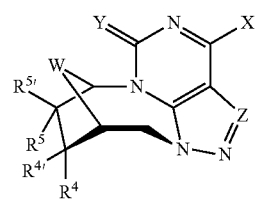

1 (B)

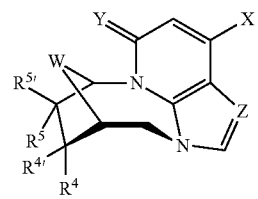

1 (C)

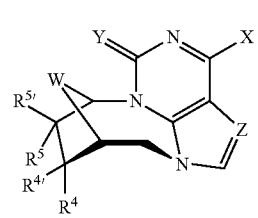

1 (D)

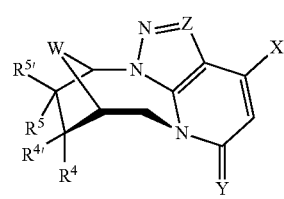

2 (A)

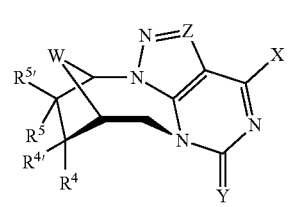

2 (B)

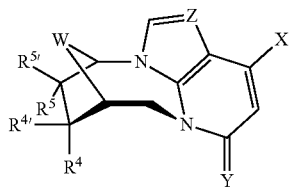
2 (C)

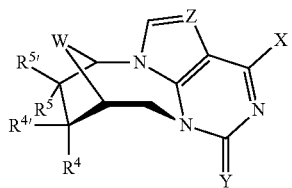
2 (D)

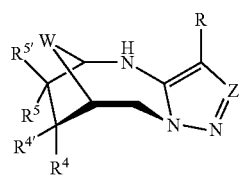
3 (E)

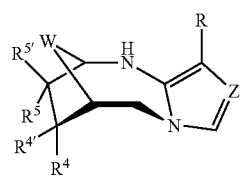
3 (F)

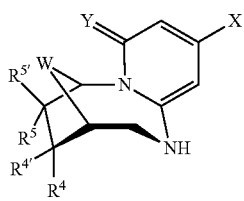
4 (E)

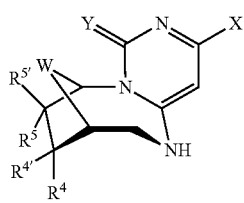
4 (F)

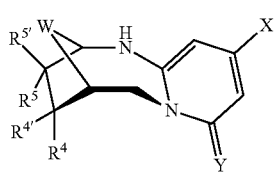
5 (E)

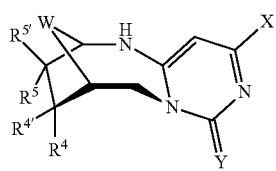
5 (F)

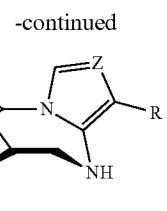
6 (E)

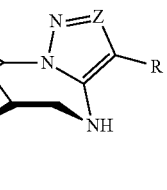
6 (F)

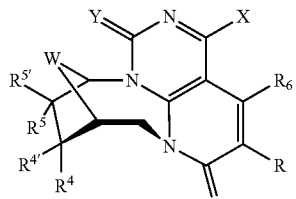
7 (A)

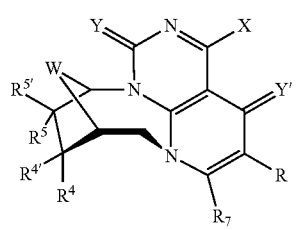
7 (B)

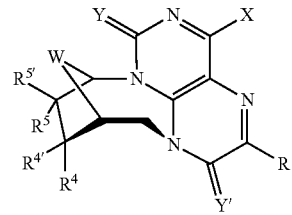
7 (C)

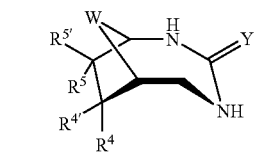
8 (C)

Synthesis of Class 1(A-B) Compounds

A compound of class 1, in which the 6-membered part of the bicyclic heteroring links directly to the tetrahydrofuran or tetrahydrothiophene or cyclopentane derivative, and the 5-membered ring contains 3 nitrogens, one of which is linked to the tetrahydrofuran or tetrahydrothiophene or cyclopentane derivative through a methylene bridge [1(A) and 1(B)] can be synthesized by the following way (Scheme 1). For example, 5-nitropyrimidin-2-one (9, Y=H, Z=N) or 5-nitropyridine (9, Y=H, Z=CH) is condensed with 1-O-acetyl-2,3,5-tri-O-benzoyl-D-ribofuranose by Vorbruggen procedure to give nucleoside 10 (R=Bz, Ac, substituted Bz, benzyl, or the like). Treatment of 10 with sodium or lithium azide in an inert solvent, such as alkanol, acetonitrile, N,N-dimethylformamide (DMF), dimethylsulfoxide (DMSO), or hexamethyl phosphoric triamide (HMPA), gives the corresponding v-triazolo[4,5-b]pyrimidine (11, Y=H, Z=N) or v-triazolo[4,5-b]pyridine product (11, Y=H, Z=CH). After deprotection, 11 is converted into the 2',3'-O-isopropylidene derivative 12 by treatment with acetone and mineral or Lewis acid (e.g., $H_2SO_4$, $CuSO_4$, or $ZnCl_2$, or the like) or with 2,2-dimethoxypropane in acetone in the presence of a catalytic amount of acid, such as HCl, TsOH, or MsOH. Tosylation or mesylation to 13 followed by heating afford the cyclonucleoside 14. It has also been discovered that the benzoyloxy group itself in compound 11 can act as a leaving group. Especially, an acyloxy group containing an electron-withdrawing group, such as p-fluorobenzoyl, p-nitrobenzoyl, or the like, at the C-5' position gives a good result. Deacetonation in dilute acetic acid, trifluoroacetic acid, diluted mineral acid, or an acidic resin gives the desired compound 15. Compound 14 and 15 can be reduced to the corresponding saturated product (X and Y can be independently $CH_2$, CH-halogen, CH-alkyl, NH, N-alkyl). Alternatively, application of Mitsunobu reaction to 12 gives 14 directly. Also, a protected natural nucleoside, such as cytidine or uridine (Z=N, Y=$NH_2$ or OH, R=Ac, Bz, substituted Bz, benzyl, or the like, or R',R''=iso-propylidene) is nitrated to 10, and subsequent series of reactions yield 15. From a L-ribosyl derivative, the L-enantiomer of 15 can be synthesized by the same chemistry.

An intermediate 11 can also be prepared by Vorbruggen's condensation (Rizkalla, B. H.; Broom, A. D. *J. Org. Chem.*, 1972, 37, 3980) of a purine containing 2-oxo function, such as xanthine, or a strong electron-releasing group at C6, such as 6-dimethylaminopurine, with a protected ribofuranose. The present invention also includes our discovery that certain protected intermediates (10 and 11, R=Bz) can be directly converted into the desired cyclonucleoside 15. This novel process has a great advantage over the traditional synthesis as the targeted compound 15 can be obtained in only 3 steps (see Example 7).

The compounds of Class 1(A) can also be synthesized from a pyrimidine nucleoside bearing a good leaving group at the C-5 position (Scheme 2). 5-Bromo-2',3'-di-O-isopropylideneuridine (17) is sulfonylated with tosyl chloride, mesyl chloride, triflyl chloride, or triflic anhydride in the presence or the absence of base such as pyridine, triethylamine, DBU, DBN, 4-dimethylaminopyridine, or lutidine to give 18. Treatment of 18 with $NaN_3$, $LiN_3$, or $KN_3$ in an inert solvent, such as DMF, DMSO, HMPA, or the like, gives the 5'-azido derivative 19. Upon heating 19 in an inert solvent, compound 14 is produced in high yield.

Scheme 1

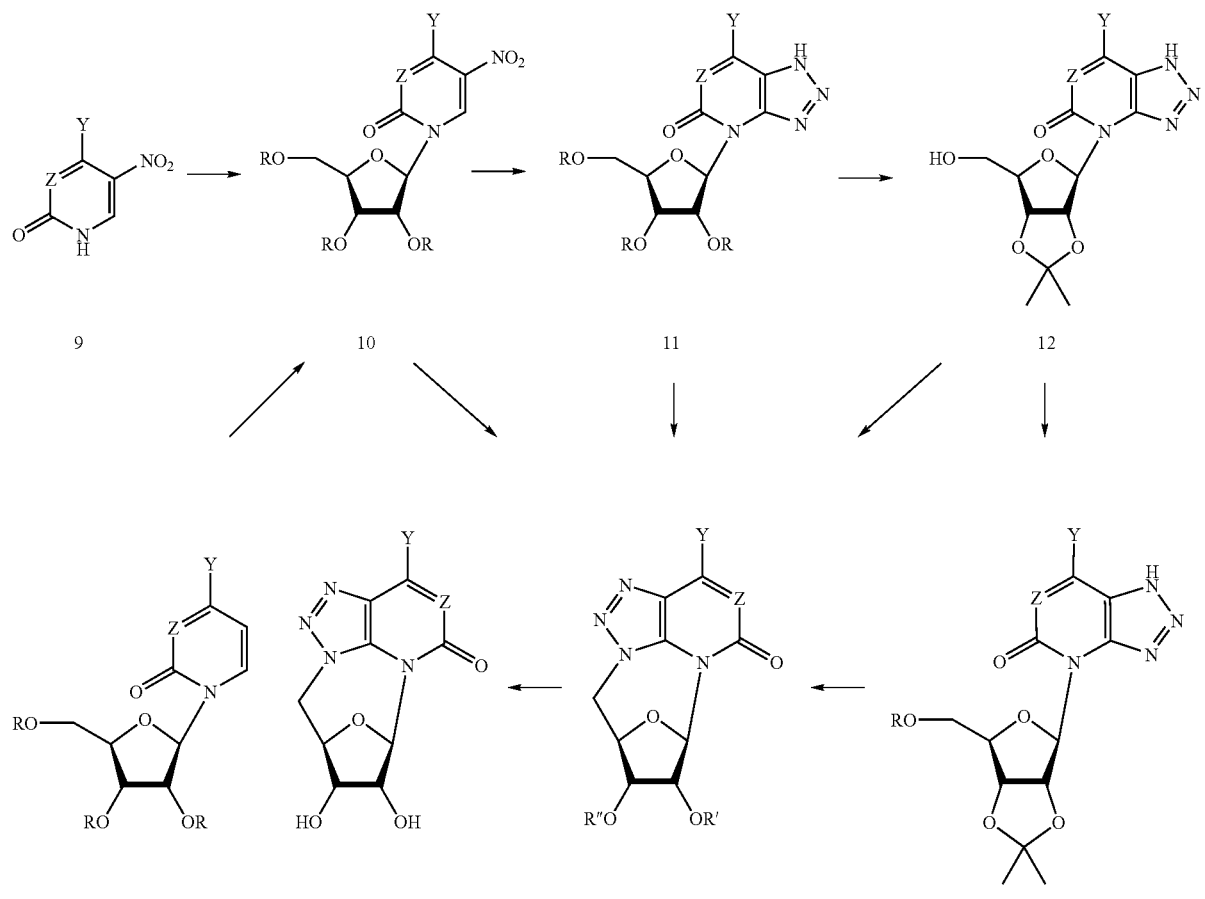

Scheme 2

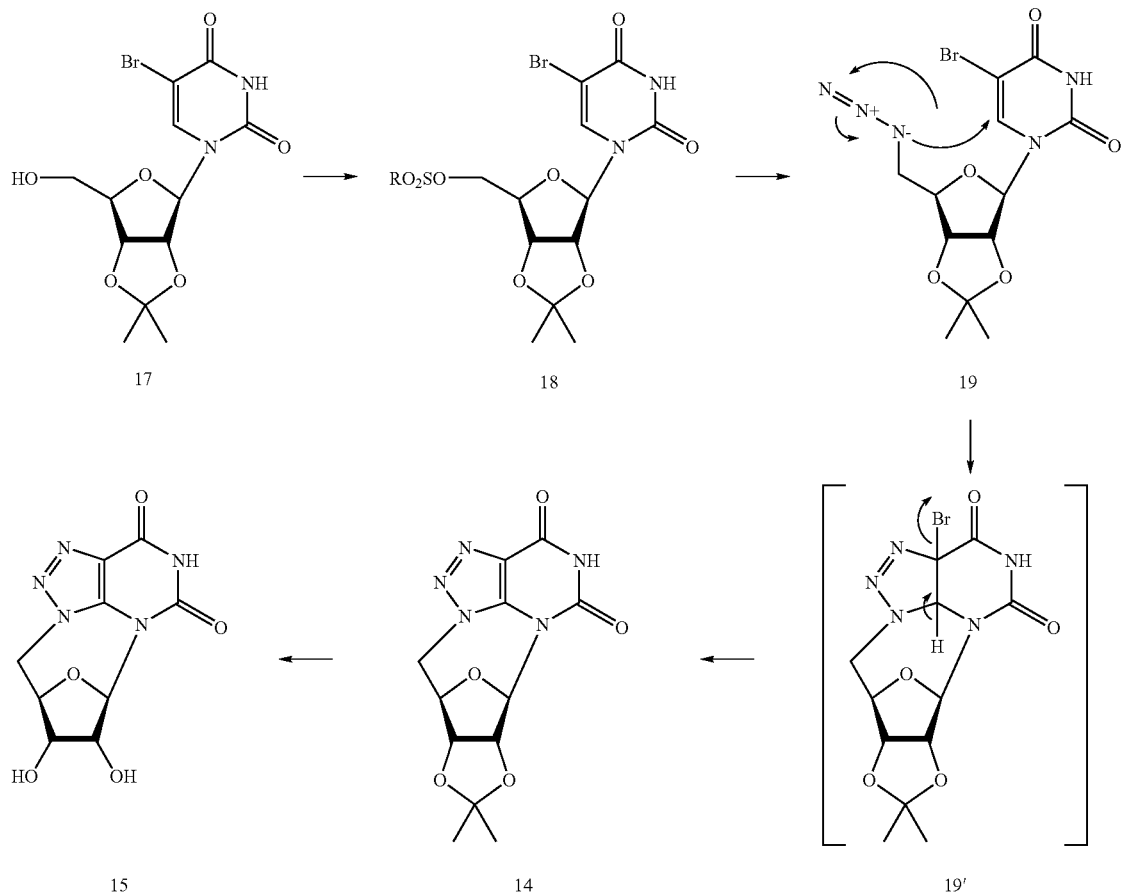

A plausible mechanism for the formation of 14 from 19 would be through a [2,3]-dipolar addition of the 5'-azido moiety to the 5,6-double bond, concomitant with elimination of HBr from the adduct. Deacetonation of 14 under acidic conditions affords the corresponding free compound 15.

Synthesis of Class 1(C-D) Compounds

Condensation of 6-aminocytosine with tetra-O-protected ribofuranose, such as 20 (Scheme 3), under Vorbruggen's conditions affords the protected nucleoside 21, which, on nitrosation gives the 5-nitroso product 22. Reduction of the nitroso group gives the triaminopyrimidine nucleoside 23. Conversion of 23 to purine 24 can be accomplished by treatment with DMF with phosphoryl chloride. De-O-benzoylation in base, such as alcoholic metal alkoxide or alcoholic ammonia, followed by isopropylidenation yields 25. Intramolecular Mitsunobu reaction of 25 gives the cyclic product 26, which, upon acid hydrolysis, affords the desired product 27.

Scheme 3

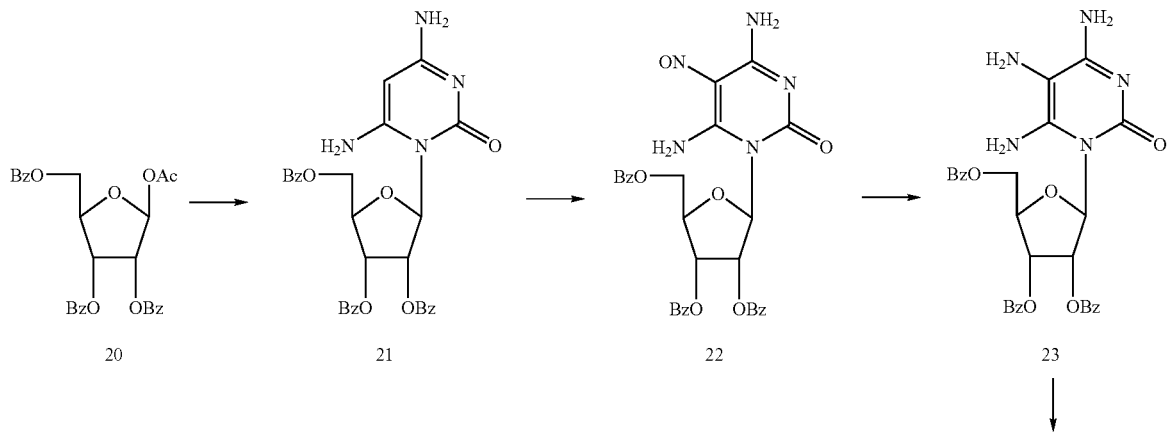

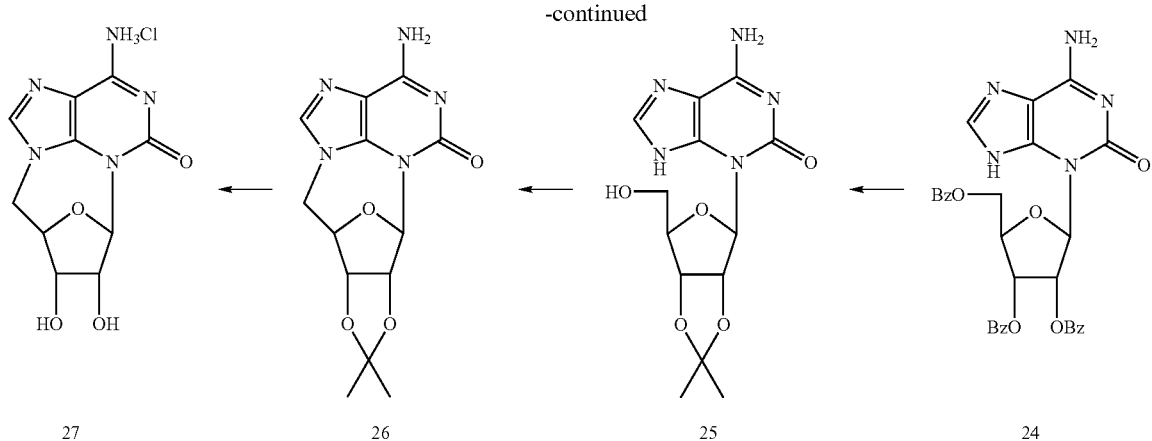

Alternatively, uridine can be converted into 5-halo-5'-O-sulfonyl-uridine-2',3'-O-acetal or ketal, such as 5-bromo-2', 3'-O-isopropylidene-5'-O-tosyl derivative (28, R=Ts, Scheme 4). Base treatment of 28 affords the 6,5'-O-cyclo derivative 29, which, upon ammonolysis, gives 6-amino-2', 3'-O-isopropylidene uridine 30. Nitrosation of 30 gives 31, and subsequent reduction to 32, followed by cyclization produces 33, which is converted to 9,5'-cyclo derivative 35 by treatment under Mitsunobu conditions to 34, followed by de-O-acetonation with acid.

Scheme 4

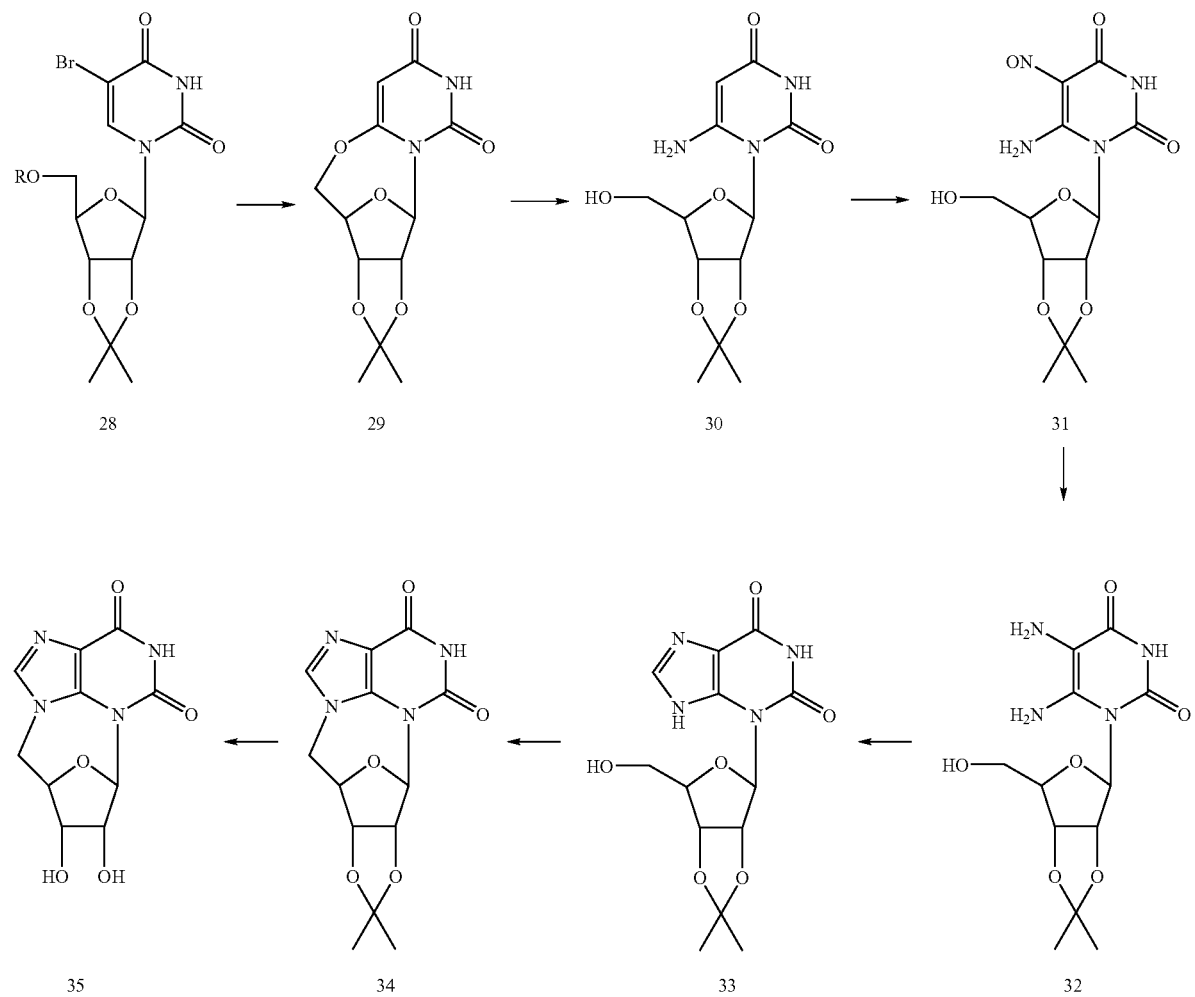

Compound 34 can be prepared from 5'-azido-5'-deoxy-2', 3'-O-isopropylidene uridine (36, Scheme 5). Bromination of 36 to 19 can be furnished by treatment with LiBr and ammonium cerium nitrate in acetonitrile. Compound 19 can be directly converted into the 6,5'-imino derivative 37 in high yield with triphenyl phosphine and ammonium hydroxide in tetrahydrofuran. Nitrosation of 37, followed by reduction gives 38, which is readily converted into 34. Compound 34 can be thiated with phosphorus pentasulfide in pyridine or with Lawesson's reagent in an inert solvent such as toluene to give 39. De-O-isopropylidenation of 39 with acid gives 40, which can be desulfated to 41 by treatment with Raney nickel. Alternatively, treatment of 39 with Raney nickel and subsequent acid hydrolysis gives 41. Treatment of 37 with chloroacetaldehyde gives pyrrolopyrimidine 42 (Scheme 6). Acidic de-O-isopropylidenation of 42 affords 43. Also alkylation with various alkyl halides in the presence of base, such as sodium or potassium carbonate or sodium or potassium hydroxide in an inert solvent, such as dimethylformamide, acetonitrile, tetrahydrofuran, or the like affords the corresponding 1-alkyl derivative 44, which, upon acid hydrolysis, gives 45.

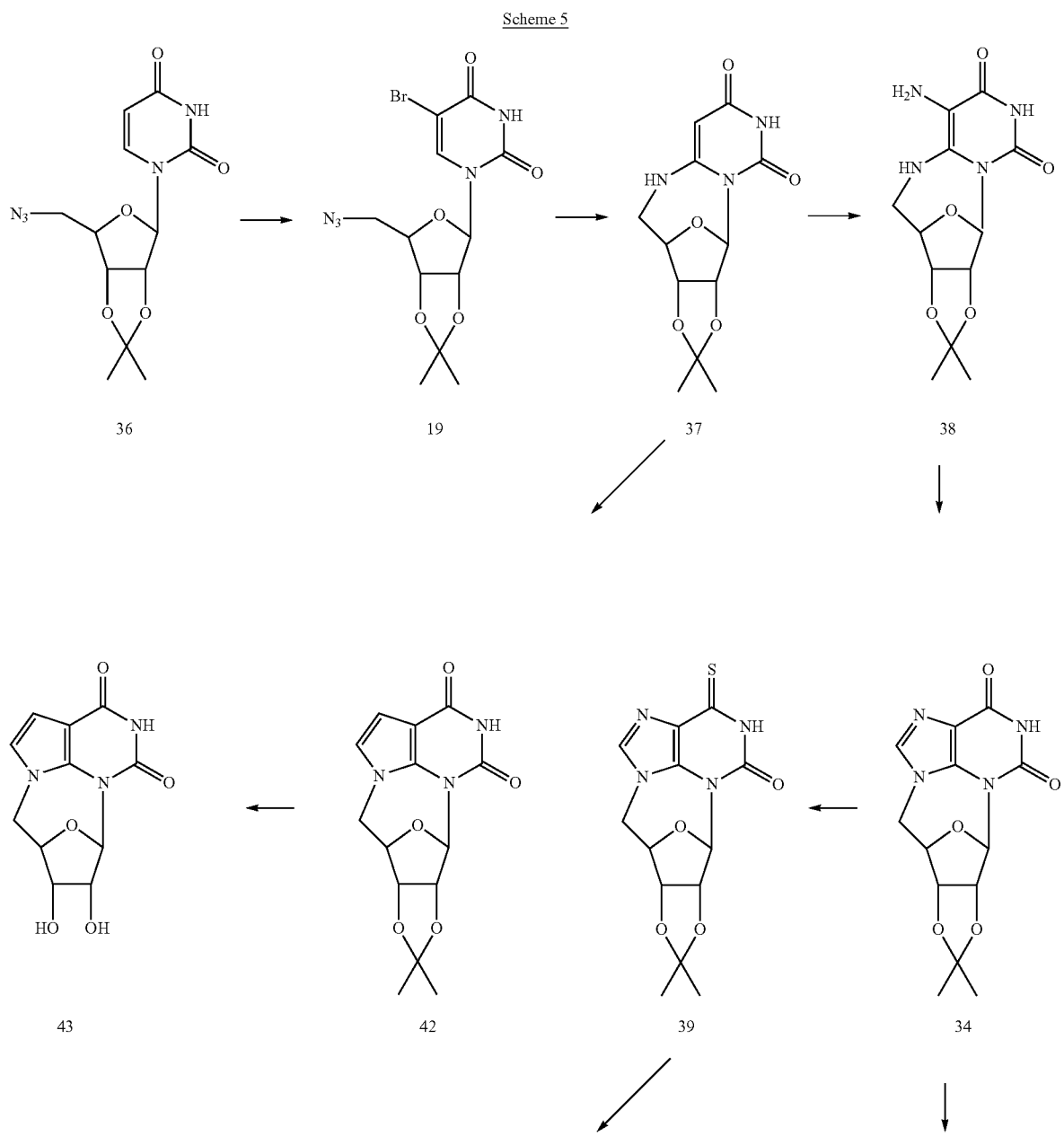

Scheme 5

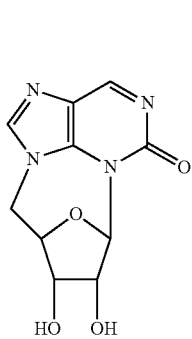

41

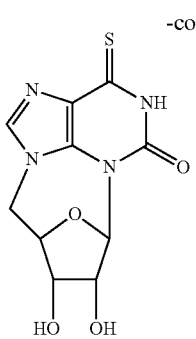

40

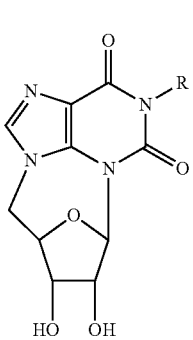

45

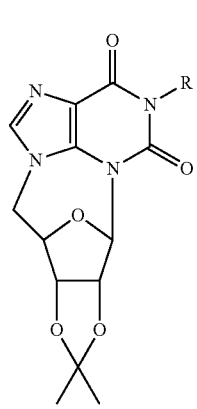

44

R=H, lower alkyl of $C_{1-6}$, ω-hydroxy-, ω-sulfhydryl-, ω-halo(F, Cl, Br, or I)—, ω-azido-, ω-amino-, ω-cyano-lower alkyl of $C_{1-6}$, or benzyl.

Treatment of 39 with ammonia gives 26, which, upon acid hydrolysis, affords the adenine derivative 27. Treatment of 42 with Lawesson's reagent affords the thio derivative 46 (Scheme 6), which can be converted to the 6-amino derivative 47 by treatment with ammonia. De-O-isopropylidenation gives 7-deazaadenine derivative 48.

Scheme 6

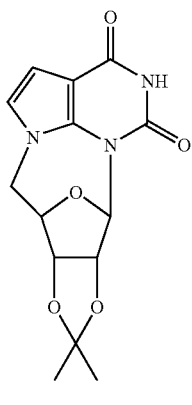

42

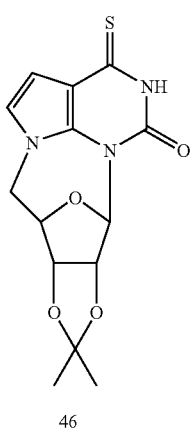

46

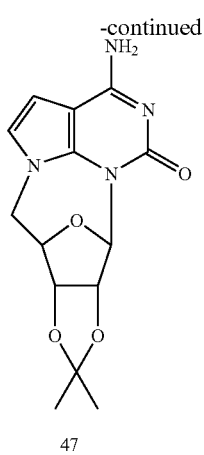

47

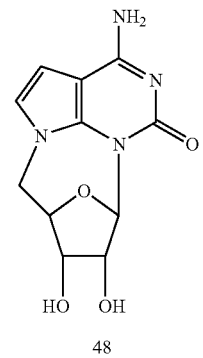

48

Condensation of sugar 20 with 6-aminouracil under Vorbruggen's conditions results in the exclusive formation of 3-ribosyl-6-aminouracil derivative (49, Scheme 7). Nitrosation of 49, followed by reduction gives 50, which, on cyclization affords 51, which is converted into the free nucleoside 52 by saponification. Isopropylidenation of 52 with 2,2-dimethoxypropane in acetone in the presence of a small amount of p-toluenesulfonic acid gives 53, which, upon treatment under Mitsunobu conditions, is converted into 54.

Scheme 7

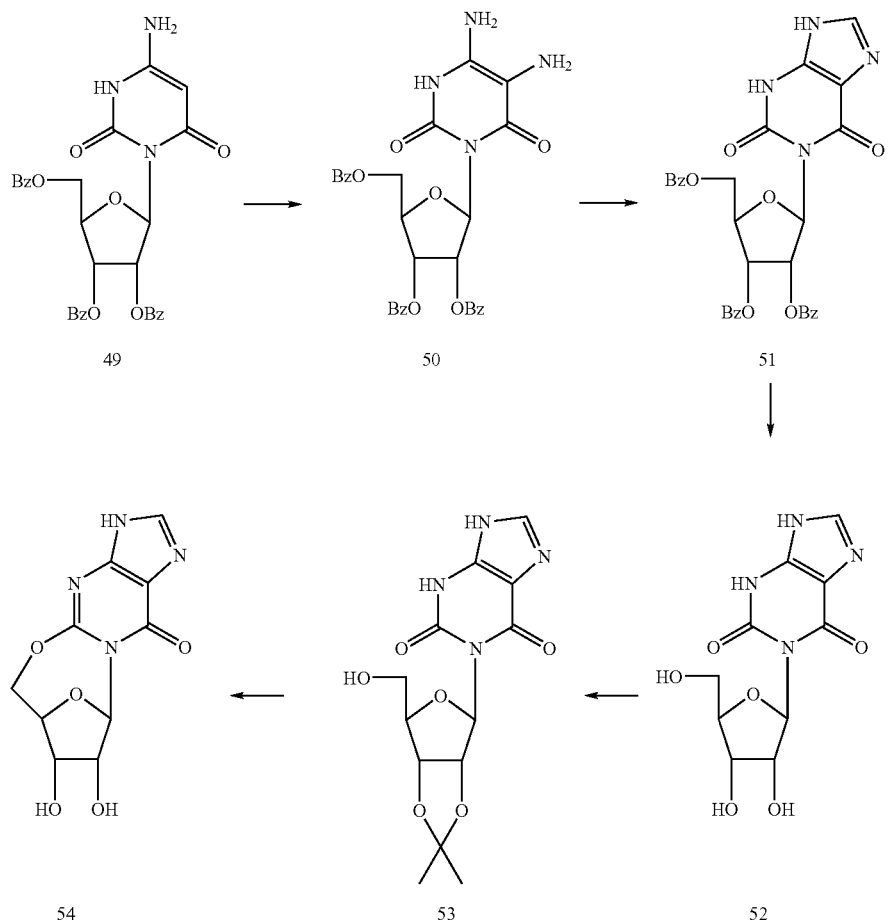

From sugar modified nucleosides, modified furan ring containing compounds are made. Sugar modified nucleosides can be prepared by (i) condensation of modified sugar with a base or (ii) by conversion of the sugar moiety in preformed nucleosides. For example, condensation of 1,2-O-acetyl-5-O-methoxycarbonyl-3-deoxy-D-glyceropentofuranose (55, Scheme 8) with 5-nitropyrimidine-2-one affords 56. The methoxycarbonyloxy group at C-5' is not a good enough leaving group, which just undergoes saponification upon treatment with base to give the free nucleoside 57. The free nucleoside 57 is benzoylated to 58, which, upon treatment with sodium azide in DMF gives 59. Saponification of 59 affords 60. Using different sugars, such as 2-deoxy-D-ribofuranose, 3-deoxy-3-fluoro-D-xylofuranose, 3-deoxy-3-fluoro-D-ribofuranose, 2-deoxy-2-fluoro-D-ribose, 2-deoxy-2-fluoro-D-arabinofuranose, and their L-sugar counterparts give their corresponding sugar modified analogues of 60.

Scheme 8

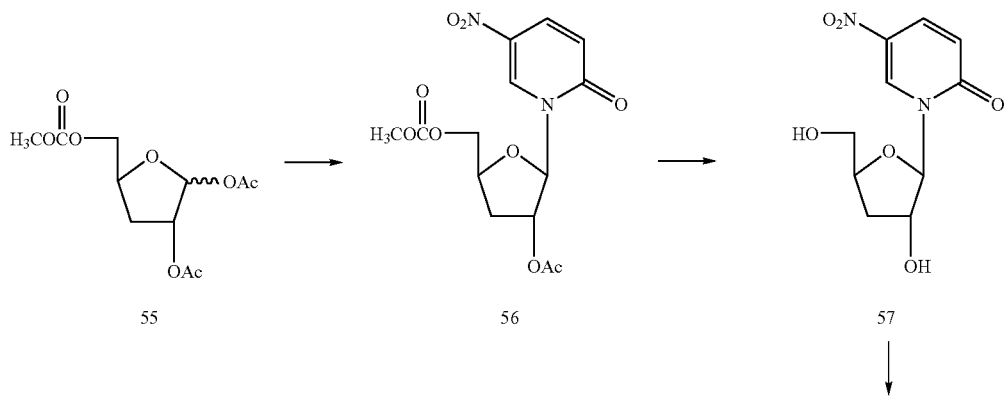

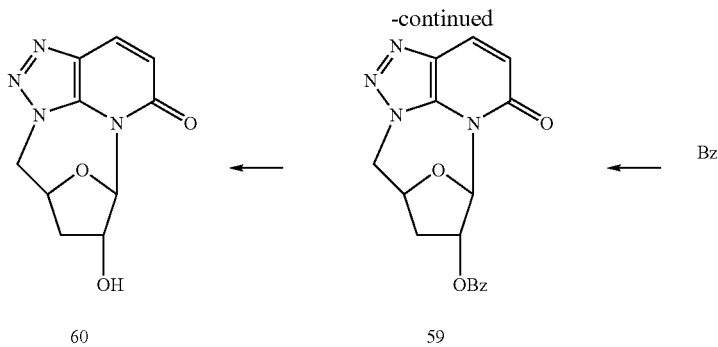

Another type of sugar-modified nucleoside that can be used in the present invention is carbocyclic sugar nucleosides. A typical example is shown in Scheme 9. Compound 61 is sulfonylated, typically mesylated, to 62, which, without isolation is treated with alkali metal azide to give 63. Heating 63 affords the 8-azaxanthine derivative 64. Acid hydrolysis of 64 gives 65. Thiation of 64 with Lawesson's reagent gives 66, which is converted into the 8-azaadenine derivative 67 by treatment with ammonia. Acid hydrolysis to remove the isopropylidene protecting group from 67 affords 68.

Post Synthetic Modifications. Various new molecules can be made from class 1 compounds. Compound 14 (Y=H, Z=CH, R'=R"=Bz) is converted into the corresponding thione (69, Scheme 10) by treatment with Lawesson's reagent in an inert solvent such as toluene or phosphorus pentasulfide in pyridine or tetraline. Saponification of the benzoyl groups affords the free compound 70. Bromination of 15 (Y=H, Z=CH) with bromine water or NBS in acetic acid gives 6-bromide 71 (X=Br) while treatment with NCS in acetic acid converts 15 into the chloride 71 (X=Cl). After treatment of 6-halide derivatives such as compound 71 with a nucleophilic agent such as various amines, a Michael addition and elimination reaction proceeds and results in 7-substituted products 72.

Scheme 9

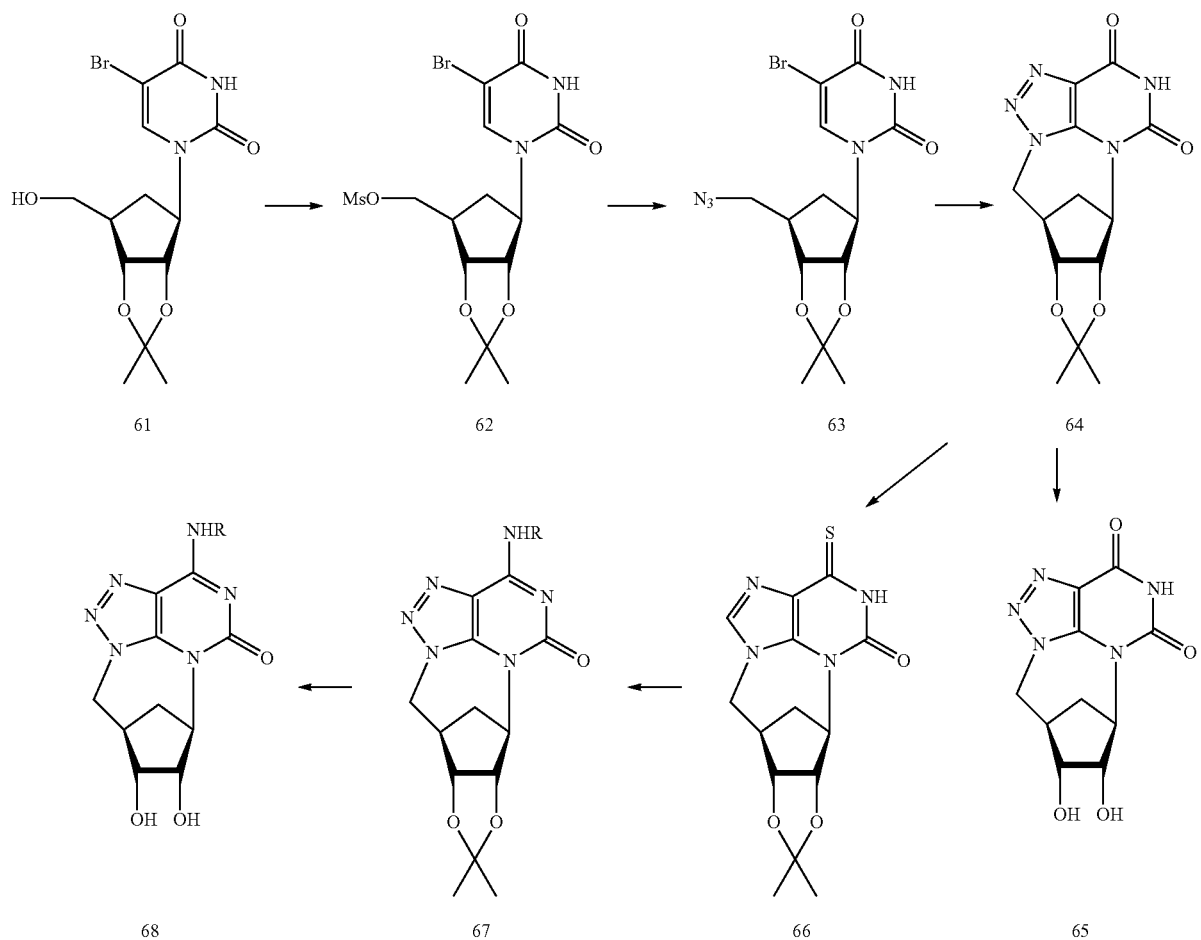

Scheme 10

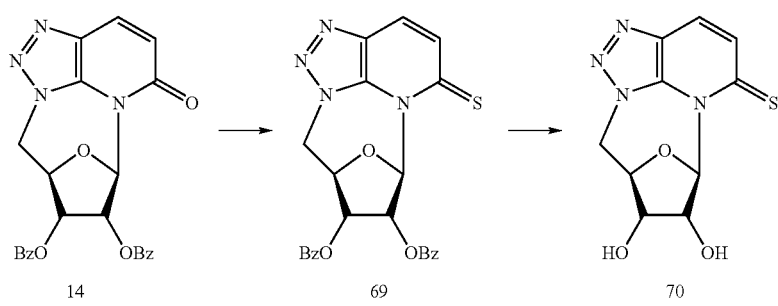

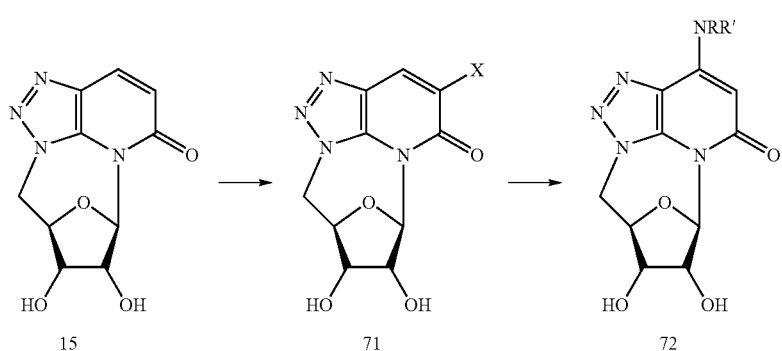

There are several ways to convert 8-azaxanthine derivatives into the corresponding 8-azaisoguanine derivatives. In Scheme 11, treatment of 14 with phosphorus pentasulfide in pyridine or with Lawesson's reagent in an inert solvent, such as toluene or methylene chloride or the like, results in the thio derivative (73, X=SH). Treatment of the thio derivative (73, X=SH) or the imidazolyl, triazolyl, or tetrazolyl derivative (73, X=imidazolyl, triazolyl, tetrazolyl, or O-sulfonyl) with various amines affords the corresponding amino derivatives 74, which, on removal of sugar protecting groups, give the corresponding free cyclonucleosides 75. It should be noted that 74 and 75 are in an equilibrium mixture of amino-imino tautomers. Also, alkylation of 14 gives the N1-substituted nucleoside 76, which is converted into the free nucleoside 77 by de-O-isopropylidenation.

Scheme 11

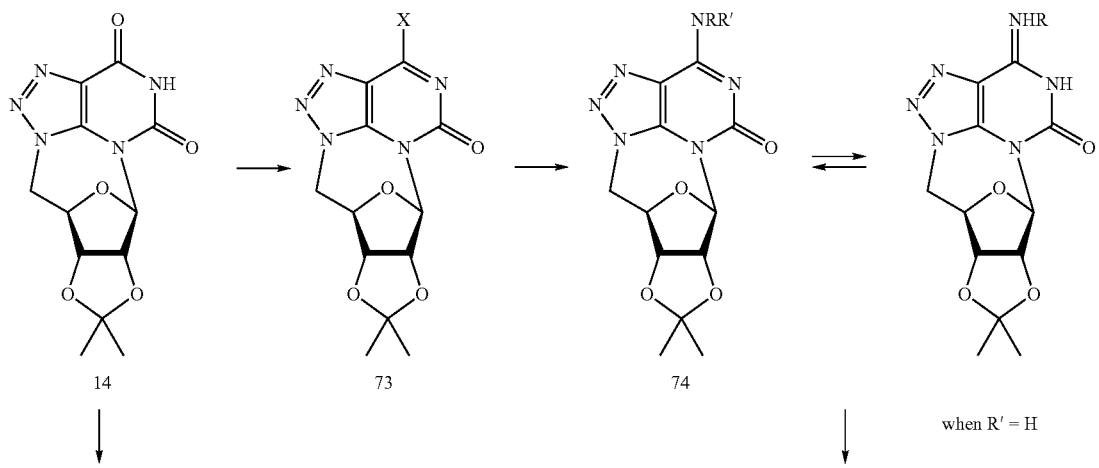

-continued

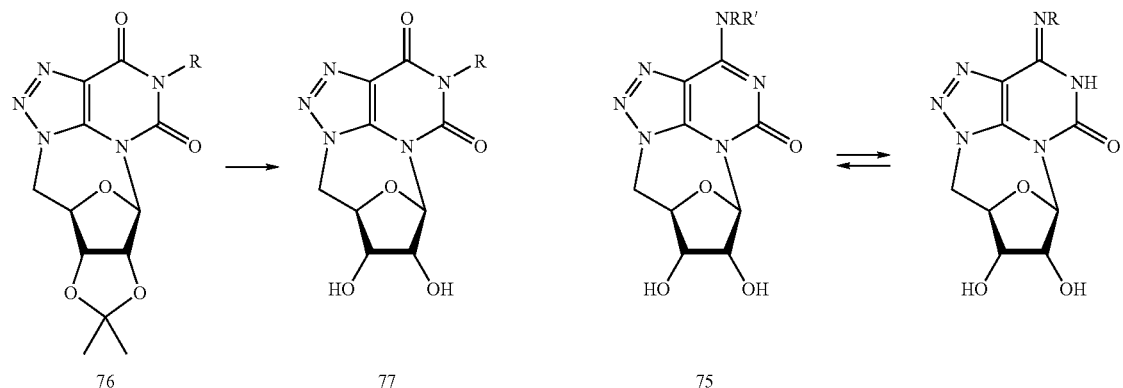

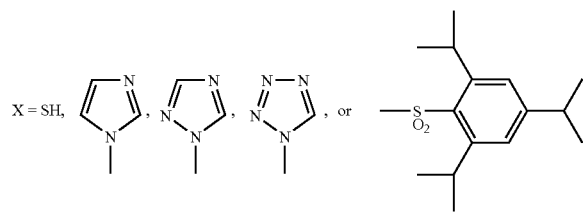

R=H, lower alkyl of $C_{1-6}$, ω-hydroxy-, ω-sulfhydryl-, ω-halo (F, Cl, Br, I)—, ω-azido-, ω-amino-, ω-cyano-lower alkyl of $C_{1-6}$, or benzyl.

The sugar portion of 15 can also be modified. Sulfonylation of 15 to 78 (Scheme 12), followed by NaI treatment gives the olefin 79. Aqueous base treatment of 78 leads to the formation of epoxide 80, which is susceptible to nucleophilic attack to produce 3-substituted arabino derivatives 81. Cyclic thiocarbonylation of 15 to 82, followed by Barton reduction affords a separable mixture of 2'- and 3'-deoxy products 83 and 84, respectively.

Scheme 12

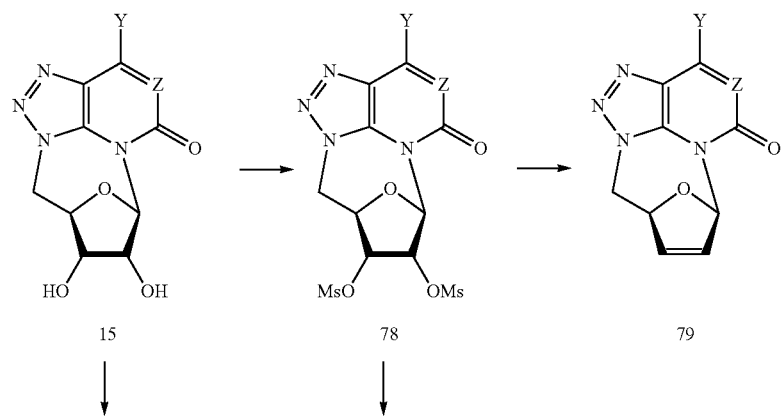

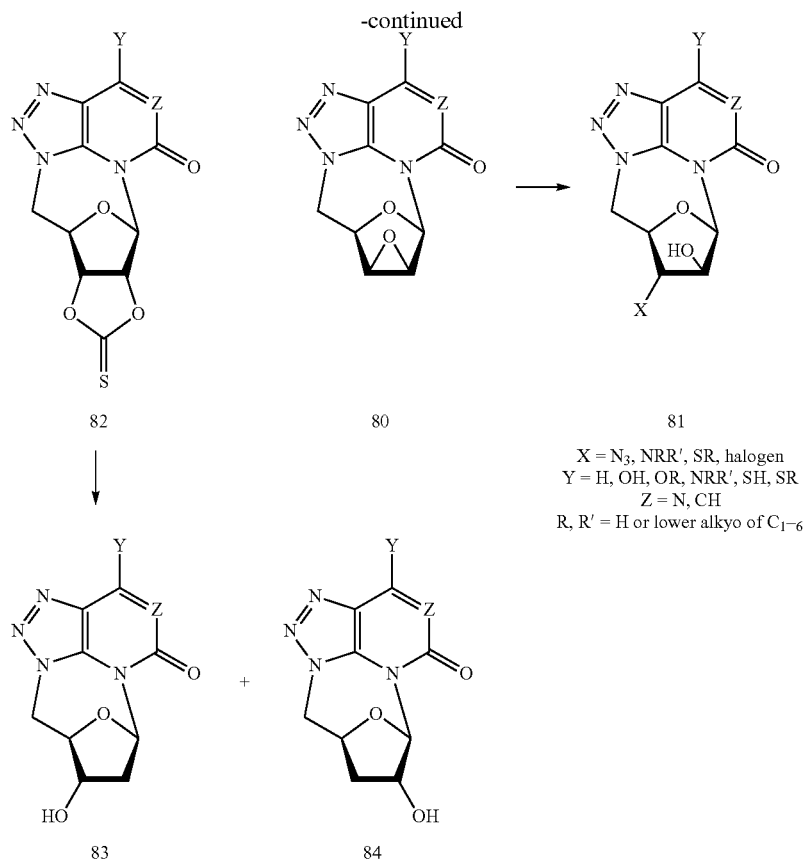

X = N₃, NRR', SR, halogen
Y = H, OH, OR, NRR', SH, SR
Z = N, CH
R, R' = H or lower alkyo of C₁₋₆

Synthesis of Class 2 Compounds

This class of compounds can be prepared from natural 2-oxo or 6-oxo or 2,6-dioxopurine nucleosides. For example, inosine (85, X=H, Scheme 13) or guanosine (85, X=NH₂) is iso-propylidenated to 86, which under Mitsunobu conditions gives the 3,5'-cyclo-derivative 87. After deacetonation of 87, the desired class 2, such as compound 88 is obtained. Similarly, xanthosine (89, Y=OH) or isoguanosine (89, Y=NH₂) is treated with 2,2-dimethoxypropane in acetone in the presence of a catalytic amount of an acid to the corresponding 2',3'-O-isopropylidene derivative 90, which, under Mitsunobu conditions, is converted to 3,5'-cyclonucleoside 91. De-O-isopropylidenation with acid furnishes the free cyclonucleoside 92.

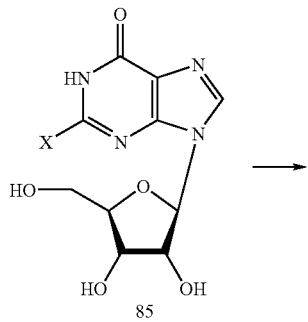

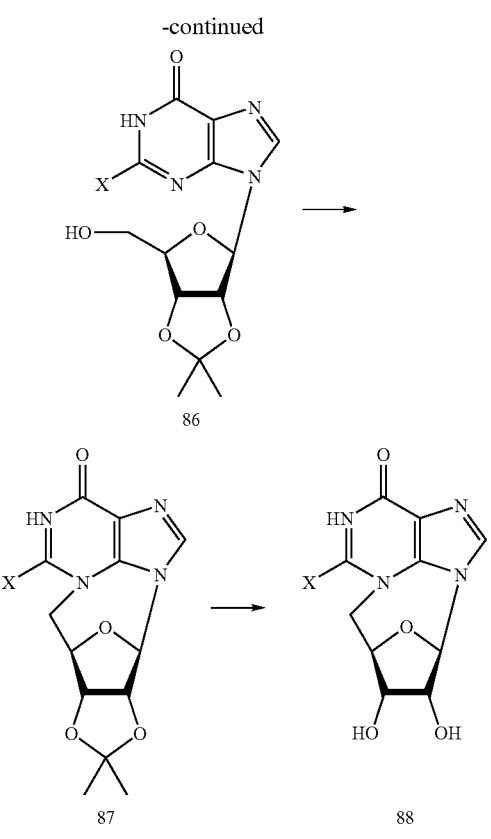

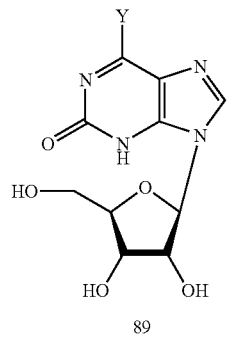

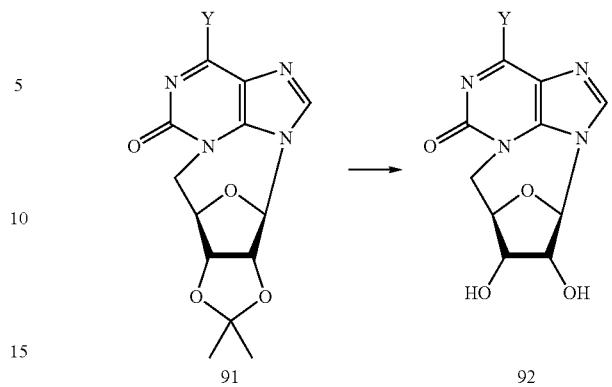

Synthesis of Class 3 Compounds

Treatment of 1-methyl 5-amino-5-deoxy-riboside (93, Scheme 14) with ethyl N-carbamoyl-cyanomethyl formimidate (94) affords the 1'-methyl riboside-5'-ylimidazole (95) (Shaw, G.; Warrener, R. N.; Butler, D. N.; Ralph, R. K, J. Chem. Soc., 1959, 1648). Upon acetolysis, 95 is converted into the desired cyclic compound 96. After saponification, the targeted product 97 is obtained. The reagent 94 can be prepared by treatment of aminocyanoacetamide with ethyl formimidate hydrochloride (Shaw, G.; Warrener, R. N.; Butler, D. N.; Ralph, R. K, J. Chem. Soc., 1959, 1648) or triethyl orthoformate (Cusack, N. J.; Hildick, B. J.; Robinson, D. H.; Rugg, P. W.; Shaw, G., J. Chem. Soc., Perkin Trans. I, 1973, 1720).

Alternatively, intermediate 95 is prepared from 5-chloro-5-deoxy-riboside (98, Scheme 14) in the following manner. Treatment of 98 with methyl 5-nitroimidazole-4-carboxylate affords 99, which is reduced to the corresponding amine 100. Ammonolysis of the ester 100 gives 95. Also, 100 is cyclized under acetolysis conditions to 101, which, upon ammonolysis gives 97.

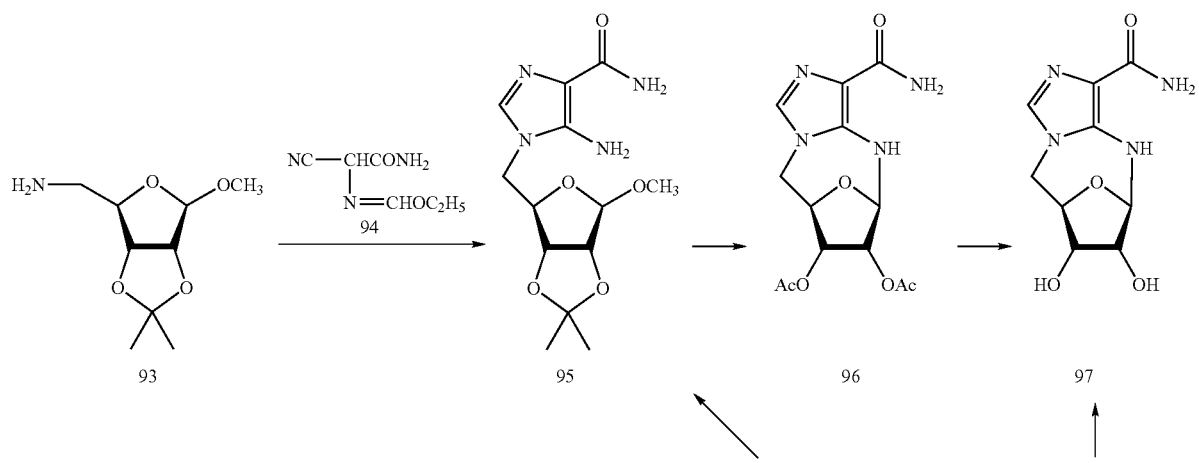

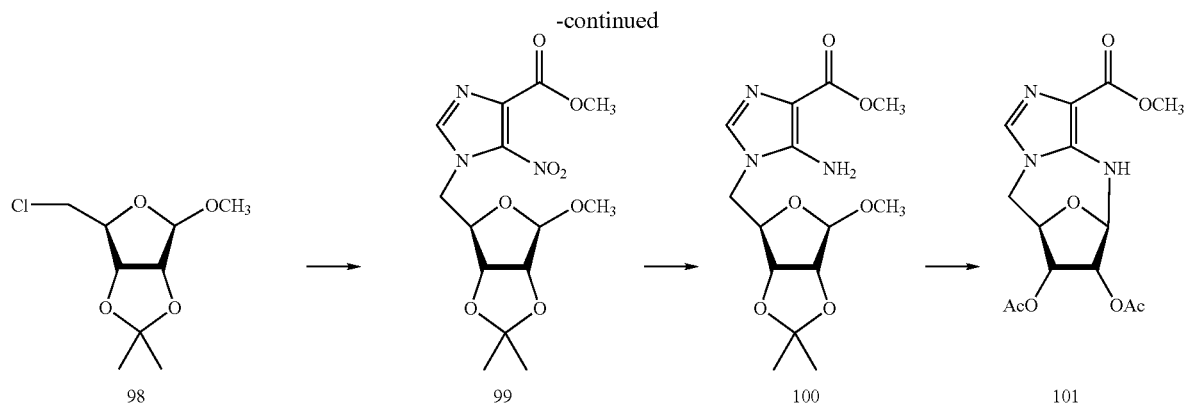

Synthesis of Class 4 Compounds

Class 4 compounds are synthesized by three different ways. The first process is to start with a pyrimidine nucleoside bearing a non-leaving group at C-5, such as 2',3'-O-isopropylidene-5-methyluridine (102, Scheme 15). After sulfonylation of 102, the product 103 is converted into the 5'-azido-5'-deoxy derivative 104, which, upon heating, in an inert solvent such as DMF, gives the cyclic product 106 via the intermediate 105 with concomitant release of nitrogen gas. A [2,3]-dipolar addition of the azido moiety to the 5,6-double bond results in the formation of the triazolo intermediate 105, which undergoes elimination of the 6-proton and subsequent elimination of $N_2$ results in the formation of 106.

Scheme 15

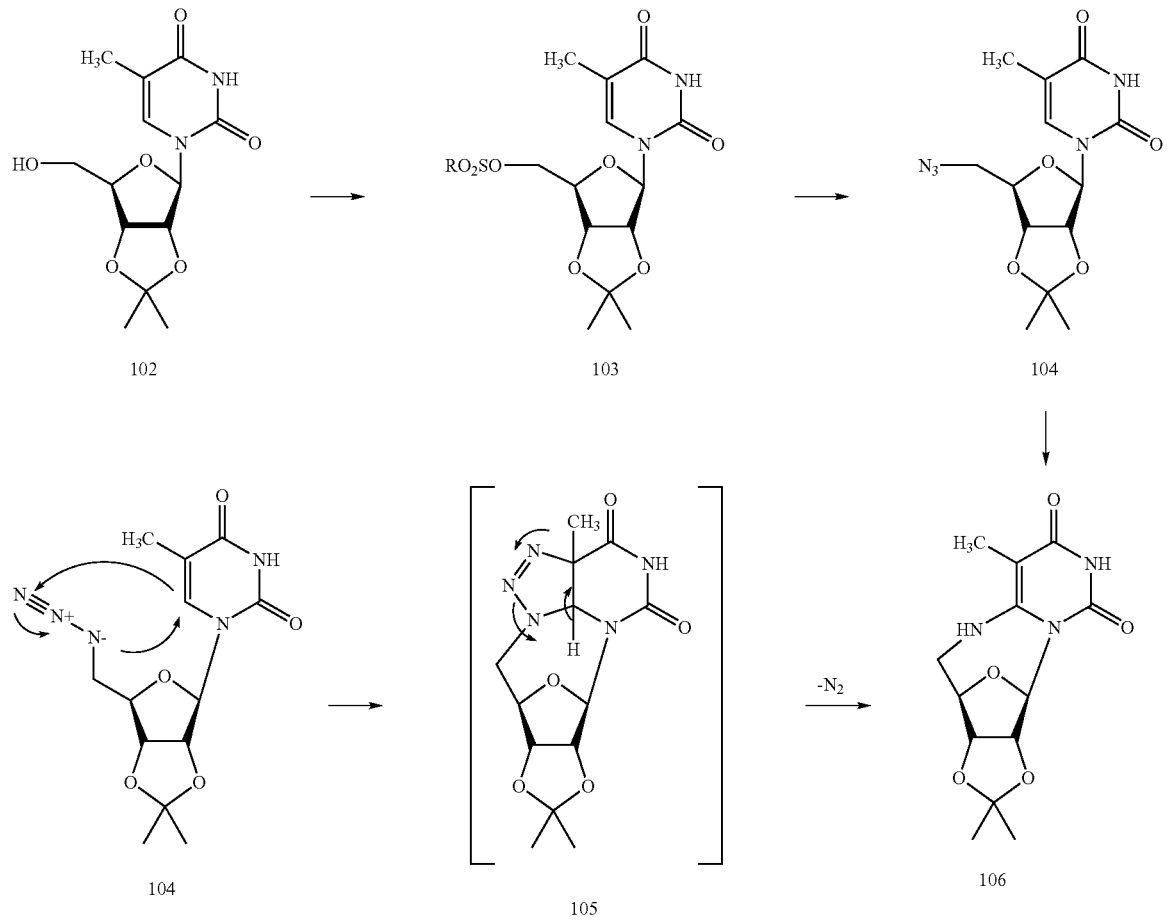

Cyclic carbonate, cyclic orthoester, benzylidene, or other cyclic groups can also serve as protecting groups.

Compound 19 (Scheme 5) from uridine can be converted into 37, which, after de-O-isopropylidenation gives 107 (Scheme 16). In a similar manner 108 can be obtained from 38.

The third route starts with alkylation of 6-amino-pyrimidinone (Z=N) or -pyridone (Z=CH), with 5-halogeno-5-deoxy-2,3-O-isopropylidene-riboside (112, Scheme 18) in base to give 113. Acetolysis of 113 affords cyclization product 114, which is converted to dihydroxy compound 115 by saponification.

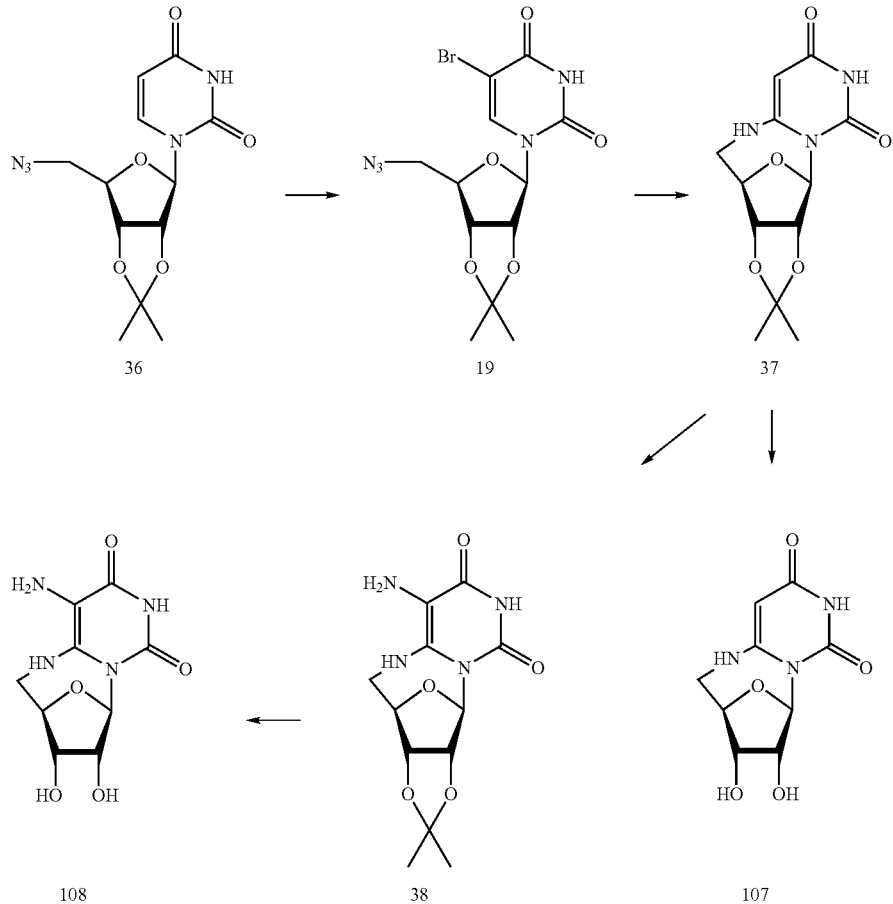

When 5-bromo-2',3'-O-isopropylidene-5'-O-sulfonyluridine (18) is treated with ammonia or methylamine, 6,5'-cyclonucleoside 111 (Scheme 17) is obtained via intermediates 109 and 110.

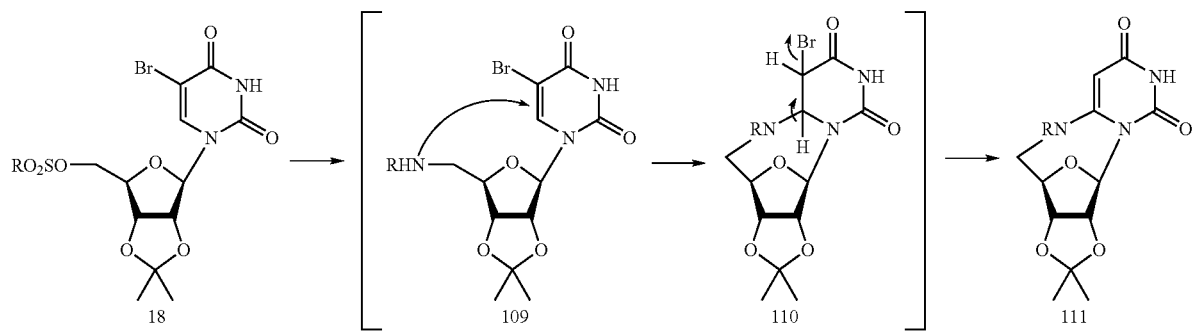

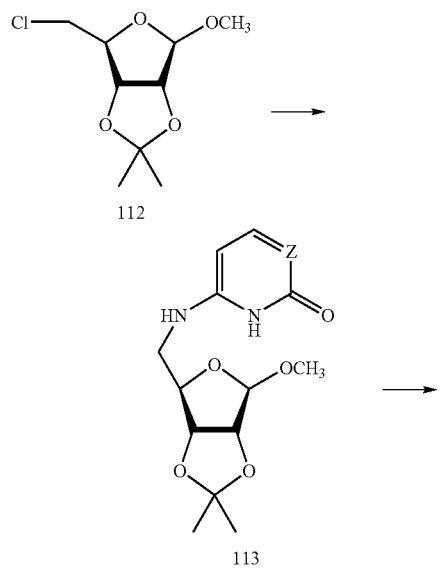

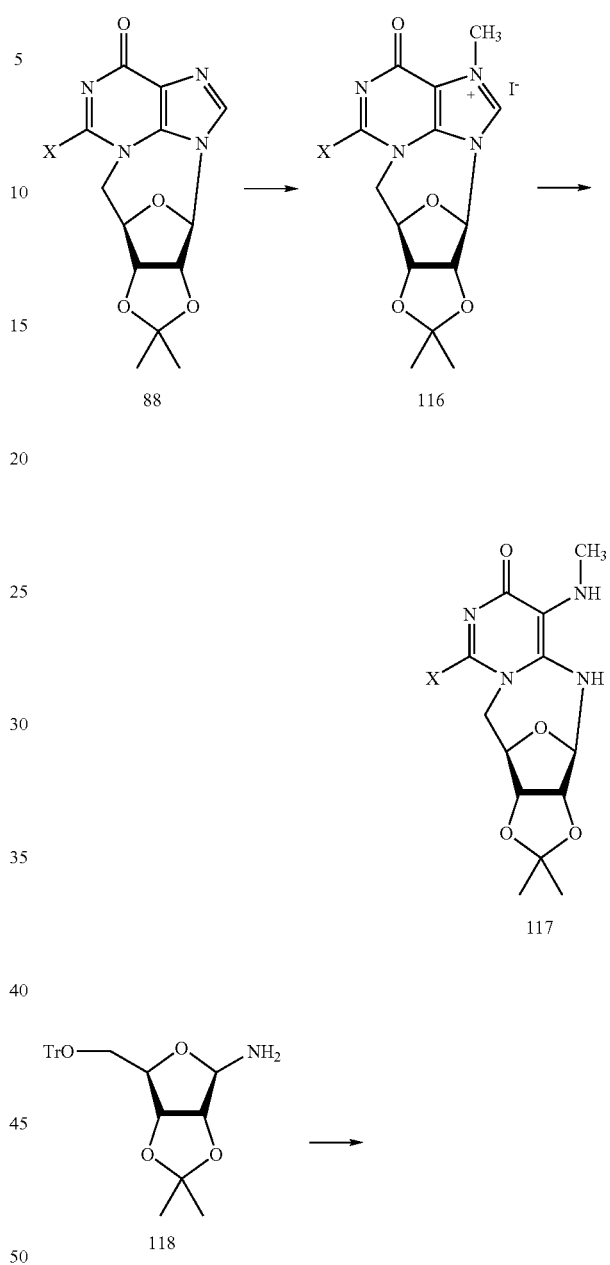

Synthesis of Class 5 Compounds

Treatment of 3,5'-cyclo-2',3'-O-isopropylidene-guanosine (88, X=NH$_2$) or -inosine (88, X=H) or another nucleoside in which X is halogen, small alkyl, S-alkyl, N-alkyl, with methyl iodide gives the corresponding 7-methyl derivative 116 (Scheme 19). Mild base treatment of the quaternary salt opens the imidazole, giving the desired product 117.

Alternatively, reaction of 2,4-dichloropyrimidine with 2,3-O-isopropylidene-5-O-trityl-ribosylamine (118) gives 119, which is converted in two steps (selective de-O-tritylation and sulfonylation with tosyl chloride in pyridine) into the quaternary salt 120. Treatment of 120 with water, followed by neutralization affords the desired cyclic compound 121. Instead of the isopropylidene protecting group, cyclic carbonate, cyclic orthoester, benzylidene, or other cyclic groups can also serve as protecting groups.

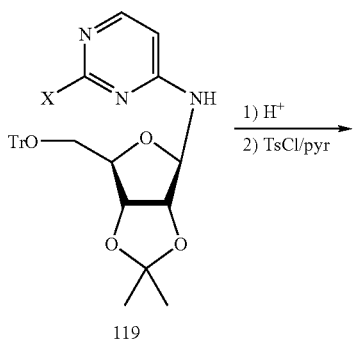

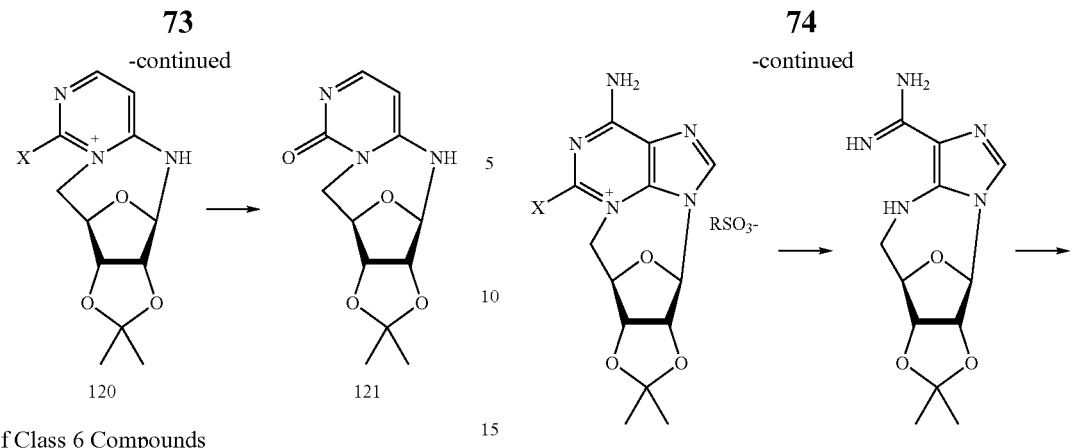

Synthesis of Class 6 Compounds

This type of compounds can be synthesized from regular purine nucleosides. For example, 2',3'-O-isopropylideneadenosine (122, X=H, Scheme 20) is sulfonylated to 123, which, upon heating, cyclizes to a quaternary salt 124. Base treatment of 124 affords 125 which is then treated with acid to give the desired product 126. This sequence of reactions can be applicable to other purine nucleosides and purine nucleoside analogues, such as guanosine, inosine, toyokamycin, tubercidin, or formycin, etc.

Naturally-occurring imidazole nucleoside, AICAR (127) can be converted into the 2',3'-O-isopropylidene derivative 128, which, after sulfonylation to 129, followed by heating in an inert solvent in the presence of a strong base such as DBU, cyclized to yield the cyclic product 130. Deacetonation of 130 in acid affords the desired compound 131. This sequence of reactions can be applicable to other 5-amino-imidazole, -triazole, or 2-amino-pyrrole nucleosides. Instead of the isopropylidene protecting group, cyclic carbonate, cyclic orthoester, benzylidene, or other cyclic groups can also serve as protecting groups.

Scheme 20

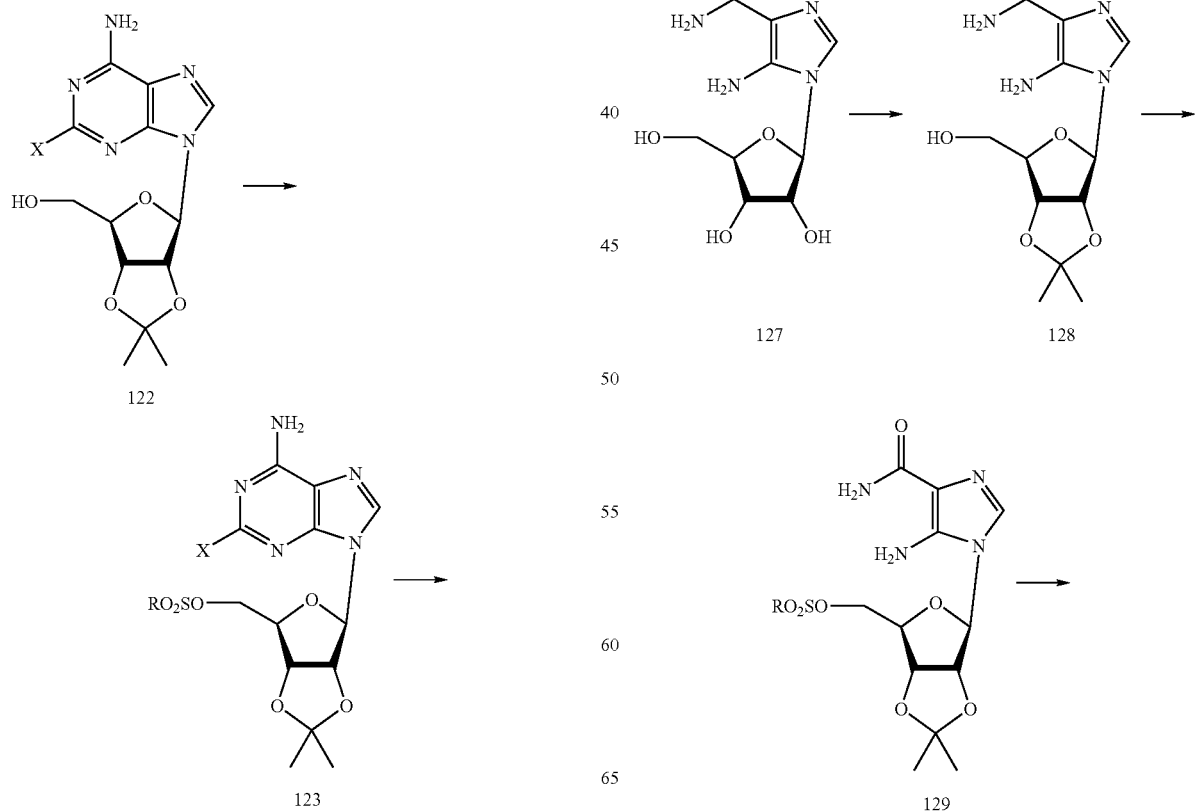

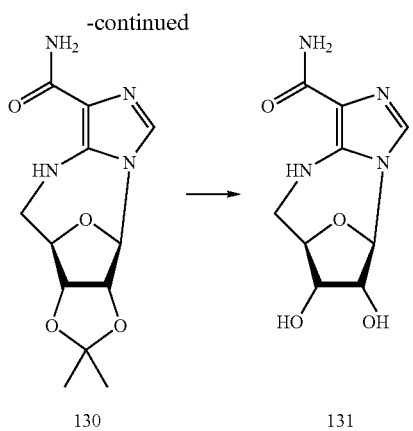

130    131

Synthesis of Class 7 Compounds

This class of compounds can be synthesized from 1-ribofuranosylpyrido[2,3-d]pyrimidines (Rizkalla, B. H.; Broom, A. D., *J. Org. Chem.,* 1972, 37, 3980; Anderson, G. L.; Broom, A. D., *J. Org. Chem.,* 1977, 42, 977) or 8-ribofuranosyl-pteridines (Pfleiderer, W.; Autenrieth, D.; Schranner, M., *Chem. Ber.,* 1973, 106, 317). However, the easiest approach is to start with 5-cyanouridine (134, Scheme 21), which can be prepared in two-steps from 2',3'-O-isopropylidene-5'-O-trityl-5-bromouridine (132) (Anderson, G. L.; Broom, A. D., *J. Org. Chem.,* 1977, 42, 977). Treatment of 132 with benzyloxymethyl chloride in DMF in the presence of DBU affords the protected nucleoside (133) in high yield. Conversion of 133 into 134 in high yield is achieved by treatment of 133 with sodium cyanide in DMF according to Inoue and Ueda (Inoue, H.; Ueda, T., *Chem. Pharm. Bull.,* 1978, 26, 2657). When 134 is treated with ethyl cyanoacetate in alcoholic sodium alkoxide, such as ethanolic sodium ethoxide, 7-amino-3-benzyloxymethyl-1-(2',3'-O-isopropylidene-5'-O-trityl-β-D-ribofuranosyl)pyrido[2,3-d]pyrimidine-2,4(1H,3H)-dione-6-ethylcarboxylate (135) is obtained in good yield. Reduction of 135 over palladium charcoal removes the protecting groups at N3 and O5' simultaneously giving 136 in good yield. The 7-amino group in 136 is converted into the oxo group by deamination with nitrous acid to give 137, which, upon treatment with triphenylphosphine and diethyl azodicarboxylate, furnishes cyclization to one of the targeted compounds 138. Reaction of 139 with liquid ammonia or ethanolic ammonia gives the corresponding carboxamide 140, which is further converted into 6-cyano derivative 141 by treatment with trifluoroacetic anhydride in a mixture of dioxane and pyridine.

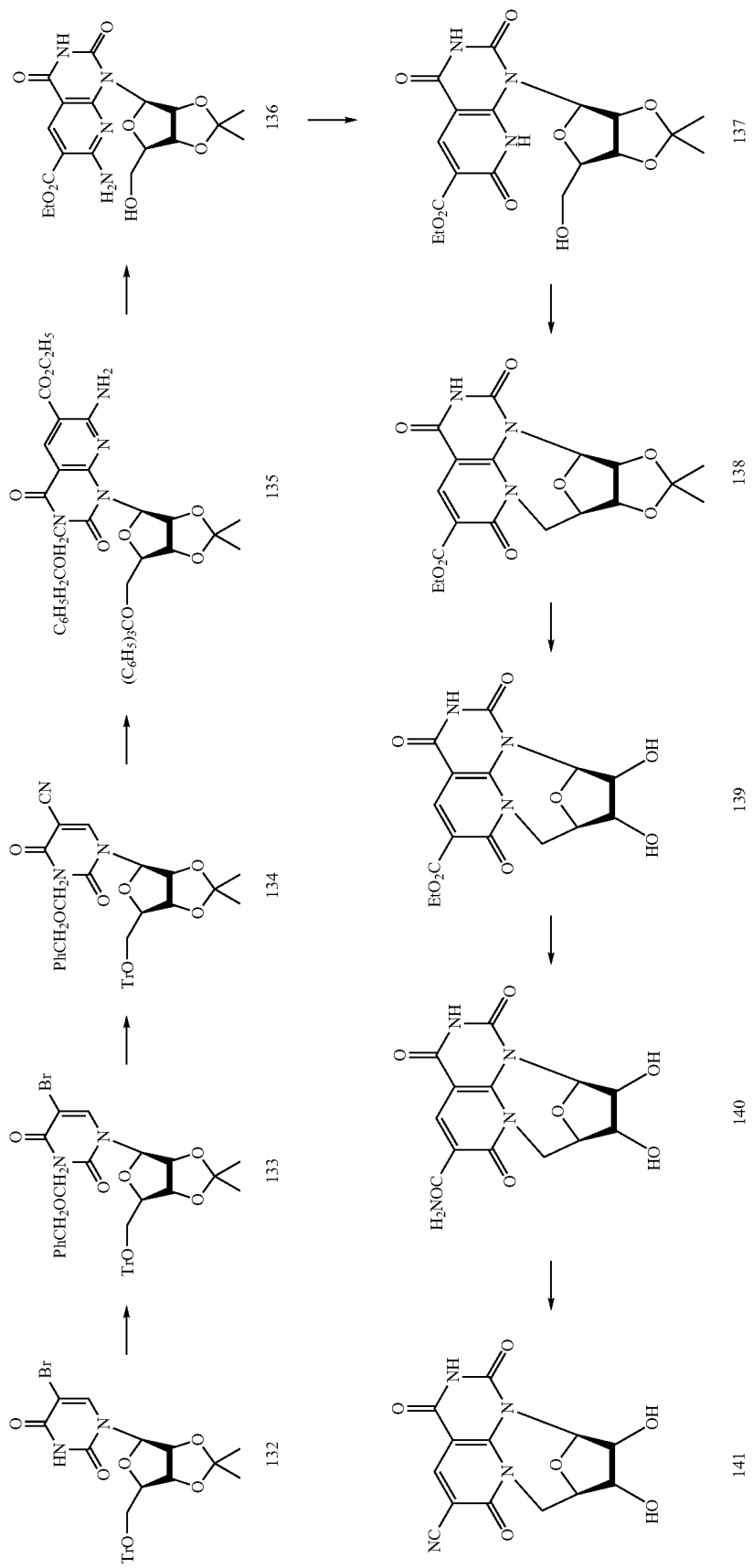

Synthesis of Class 8 Compounds

1-Amino-1-deoxy-2,3-O-isopropylidene-5-O-trityl-D-ribofuranose (142, Scheme 22) is treated with ethyl carbamate to give (2,3-O-isopropylidene-5-O-trityl-D-ribofuranosyl) urethane (143). Selective de-O-tritylation of 143 in 80% aqueous acetic acid, followed by ammonia treatment affords isopropylidene ribosylurea (144). Application of Mitsunobu reaction on 144 with triphenyl phosphine and diethyl azocarboxylate gives the desired cyclic urea 145 (X=O). Deacetonation of 145 affords the target compound 146.

Alternatively, 2,3-O-isopropylidene-D-ribofuranose (147) is chlorinated with thionyl chloride in anhydrous ether or tetrahydrofurane to give 1,5-dichloro-1,5-dideoxy derivative 148. Cyclization of 148 with urea or guanidine affords the desired cyclic urea 145 (X=O) or cyclic guanidine (145, X=NH). Deacetonation of 145 affords 146.

or m (multiplet). All J-values are in Hz. FAB mass spectra were recorded in the positive- ($FAB_>0$) or negative- ($FAB_<0$) ion mode on a JEOL DX 300 mass spectrometer. The matrix was 3-nitrobenzyl alcohol (NBA) or a mixture (50:50, v/v) of glycerol and thioglycerol (GT). Specific rotations were measured on a Perkin-Elmer 241 spectropolarimeter (path length 1 cm) and are given in units of $10^{-1}$ deg $cm^2$ $g^{-1}$. Elemental analyses were performed by Atlantic Microlab Inc. (Norcross, Ga.). Analyses indicated by the symbols of the elements or functions were within ±0.4% of theoretical values. Thin layer chromatography was performed on Whatman PK5F silica gel plates, with visualization of products being accomplished by UV absorbency followed by charring with 10% ethanolic sulfuric acid and heating. Column chromatography was carried out on Silica Gel (Fisher, S733-1) at atmospheric pressure.

Scheme 22

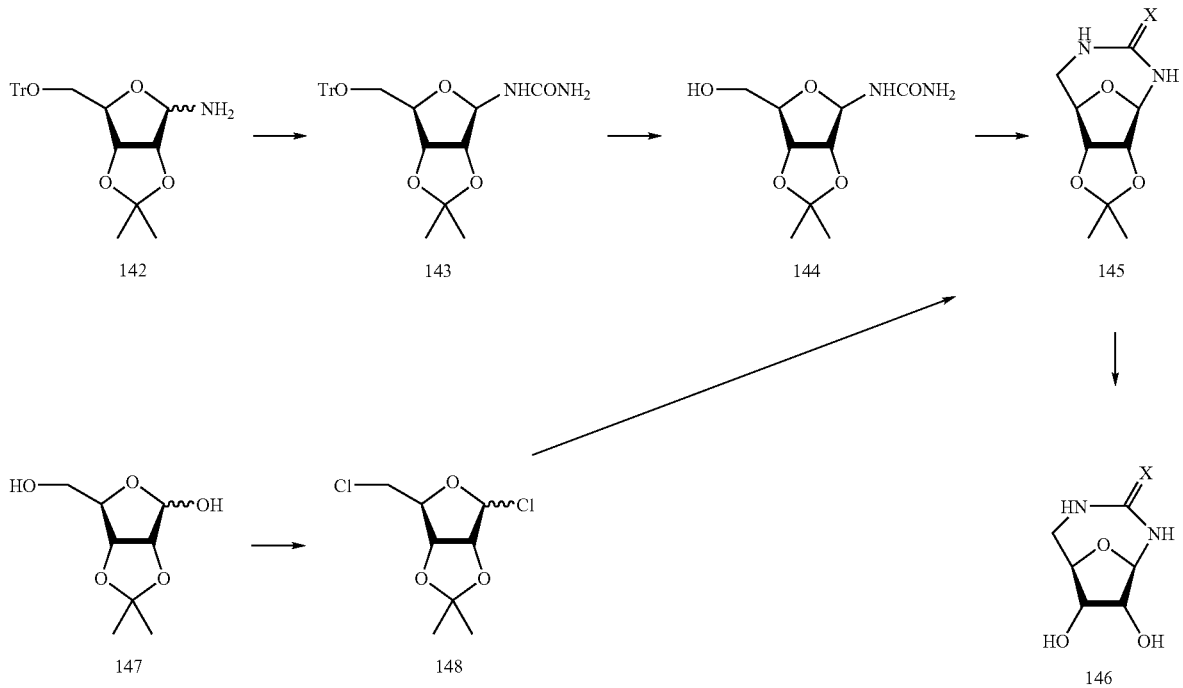

This invention is further illustrated in the Experimental Details section which follows. The Experimental Details section and Examples contained therein are set forth to aid in an understanding of the invention. This section is not intended to, and should not be interpreted to, limit in any way the invention set forth in the claims which follow thereafter.

EXAMPLES

Melting points were determined in open capillary tubes on an Electrothermal digit melting point apparatus and are uncorrected. The UV absorption spectra were recorded on an Uvikon 931 (KONTRON) spectrophotometer in ethanol. $^1$H-NMR spectra were run at room temperature with a Varian Unity Plus 400 spectrometer. Chemical shifts are given in ppm downfield from internal tetramethylsilane as reference. Deuterium exchange, decoupling experiments, or 2D-COSY were performed in order to confirm proton assignments. Signal multiplicities are represented by s (singlet), d (doublet), dd (doublet of doublets), t (triplet), q (quadruplet), br (broad), Example 1

1-(2',3',5'-Tri-O-benzoyl-β-D-ribofuranosyl)-5-nitropyridine-2(1H)-one (10, R=Bz, Y=H, Z=CH)

5-Nitro-2-pyridone (5.6 g, 40 mmol) in hexamethyldisilazane (80 mL) was refluxed with a catalytic amount of ammonium sulfate for 6 hour in an argon atmosphere. Excess solvent was removed in vacuo, and the residue dissolved in 1,2-dichloroethane (100 mL). To this solution were added 1-acetyl-2,3,5-tri-O-benzoyl-β-D-ribofuranose (19 g, 37.6 mmol) in anhydrous 1,2-dichloroethane (100 mL) and 1N solution of tin (IV) chloride in methylene chloride (7.68 mL), and the mixture was heated under reflux for 8 hours. After being kept at room temperature overnight, the reaction mixture was diluted with methylene chloride, washed with saturated sodium carbonate solution, and filtered through a Celite pad. The organic layer was separated, washed with water, dried, filtered, and concentrated to give a residue, which was crystallized from ethanol. The product 10 (15.53 g, 70%) was obtained as a solid. The $^1$H NMR parameters in DMSO-$d_6$ were very similar to those reported for this structure.

Example 2

1-(β-D-Ribofuranosyl)-5-nitropyridine-2(1H)-one (10, R=Y=H, Z=CH)

A mixture of 5-nitro-1-(2',3',5'-tri-O-benzoyl-β-ribofuranosyl)-2-pyridone (10, R=Bz, Y=H, Z=CH; 100 mg, 0.17 mmol) and saturated methanolic ammonia (10 mL) was stirred at room temperature for 12 h. The mixture was concentrated to dryness, and the residue triturated with EtOH to precipitate 10 (R=Y=H, Z=CH), which was collected and recrystallized from water (37 mg, 81%) as a white solid. $^1$H NMR (DMSO-$d_6$+$D_2O$) δ 3.64 (m, 1H), 3.90 (m, 1H), 4.01 (m, 3H), 5.89 (s, 1H), 6.48 (d, J=10.4 Hz, 1H), 8.12 (dd, J=3.2, 10 Hz, 1H), 9.65 (d, J=3.2 Hz, 1H).

Example 3

3-(β-D-Ribofuranosyl)-1-deaza-8-azapurine-2-one (11, R=V=H, Z=CH)

A mixture of 10 (R=Y=H, Z=CH, 54 mg, 0.2 mmol) and sodium azide (20 mg, 0.3 mmol) in DMF (20 mL) was stirred at 110-120° C. for 12 h. The mixture was concentrated to dryness, and the residue purified by silica gel column chromatography with 15% MeOH in $CH_2Cl_2$ to give 11 (R=Y=H, Z=CH) (32 mg, 60%) as a solid. $^1$H NMR (DMSO-$d_6$) δ 3.53 (m, 1H), 3.66 (m, 1H), 3.88 (m, 1H), 4.16 (dd, J=5.2, 9.2 Hz, 1H), 4.79 (m, 1H), 5.04 (d, J=5.2 Hz, 1H), 5.17 (d, J=6 Hz, 1H), 6.33 (d, J=6 Hz, 1H), 6.46 (d, J=9.6 Hz, 1H), 8.01 (d, J=9.6 Hz, 1H). Anal. Calc'd for $C_{10}H_{12}N_4O_6$: C, 44.78; H, 4.51; N, 20.89; Found: C, 44.60; H, 4.53; N, 20.60.

Example 4

3-(2',3'-O-Isopropylidene-β-D-ribofuranosyl)-1-deaza-8-azapurine-2-one (12, Y=H, Z=CH)

To a solution of 11 (R=Y=H, Z=CH) (5.0 g, 18.65 mmol) in a mixture of acetone (25 mL) and DMF (50 mL) at 0° C. were added p-TsOH (353 mg, 1.86 mmol) and 2,2-dimethoxypropane (7.7 g, 74.6 mmol), and the mixture was stirred overnight at room temperature. The mixture was neutralized with sodium bicarbonate, and the precipitates formed removed by filtration. The filtrate was concentrated in vacuo, and the residue dissolved in $CH_2Cl_2$ and washed successively with brine and water. The organic layer was dried ($Na_2SO_4$), concentrated, and the residue purified by silica gel column chromatography to give 4.0 g (75%) of 12 (Y=H, Z=CH).
$^1$H NMR ($CDCl_3$) δ 1.29 (s, 3H), 1.57 (s, 3H), 3.80 (m, 1H), 3.90 (m, 1H), 4.34 (m, 1H), 5.05 (m, 1H), 5.24 (m, 1H), 6.54 (d, 1H, J=5.6 Hz), 6.64 (d, 1H, J=9.6 Hz), 7.78 (d, 1H, J=9.6 Hz).

Example 5

3-(2',3'-O-Isopropylidene-5'-O-tosyl-β-D-ribofuranosyl)-1-deaza-8-azapurine-2-one (13, R=p-MePhSO$_2$, Y=H, Z=CH)

To a solution of 12 (Y=H, Z=CH, 5.0 g, 16.9 mmol) in $CH_2Cl_2$ (50 mL) and pyridine (50 mL) were added at 0° C. p-dimethylaminopyridine (2.47 g, 20.3 mmol) and TsCl (3.86 g, 20.3 mmol), and the mixture was stirred at room temperature overnight. The mixture was concentrated in vacuo, and the residue dissolved in ethyl acetate (100 mL) and washed with water (2×50 mL). The organic layer was dried ($Na_2SO_4$), concentrated, and the residue purified by silica gel column chromatography to give 13 (R=p-MePhSO$_2$, Y=H, Z=CH) as a yellow solid (5.9 g, 80%). This product was unstable.

Example 6

9,5'-Cyclo-3-(2',3'-di-O-benzoyl-β-D-ribofuranosyl)-1-deaza-8-azapurine-2-one directly from 10 (R=Bz, Y=H, Z=CH) (14, R'=R"=Bz, =H, Z=CH)

A mixture of 10 (1 g, 1.71 mmol), sodium azide (167 mg, 2.56 mmol), and N,N-dimethylformamide (28 mL) was stirred and heated at 110-120° C. for 3 days. The solvent was removed in vacuo, and the residue purified by silica gel column chromatography with EtOAc in hexanes to give 14 as a solid. $^1$H NMR (DMSO-$d_6$) 5.00 (dd, J=4.4 and 14 Hz, 1H), 5.33 (m, 2H), 5.79 (t, J=4.8 Hz, 1H), 5.88 (d, J=5.2 Hz, 1H), 6.44 (d, J=9.6 Hz, 1H), 6.75 (s, 1H), 7.32-8.08 (m, 10H), 8.14 (d, 1H, J=9.6).

Example 7

9,5'-Cyclo-3-(β-D-ribofuranosyl)-1-deaza-8-azapurine-2-one (15, V=H, Z=CH).

Compound 14 (Y=H, Z=CH, 160 mg, 0.35 mmol) was treated with 0.5 M methanolic sodium methoxide at room temperature for 1 hour. The mixture was neutralized with acetic acid, concentrated in vacuo to dryness, and the residue purified by silica gel column chromatography with 5% MeOH in $CH_2Cl_2$ to give 15 (54 mg, 62%) as a white solid. $^1$H NMR (DMSO-$d_6$) δ 3.98 (t, J=4.4 Hz, 1H), 4.13 (m, 1 H), 4.61 (t, J=4.2 Hz, 1H), 4.83 (dd, J=4 and 13.6 Hz, 1H), 5.02 (d, J=13.6 Hz, 1H), 5.37 (d, J=7.2 Hz, 1H), 5.76 (d, J=4.8 Hz, 1H), 6.21 (s, 1H), 6.36 (d, J=9.6 Hz, 1H), 8.05 (d, J=9.6 Hz, 1H). Anal. Calc'd for $C_{10}H_{10}N_4O_4$: C, 48.00; H, 4.03; N, 22.39. Found: 48.10; H, 4.06; N, 22.45.

Example 8

2',3'-O-Isopropylidine-5-bromouridine (17)

5-Bromouridine (130 g, 0.403 mol) was suspended in acetone (1 L) and treated with 1M HCl in $Et_2O$ (25 mL) for 48 h at room temperature with stirring. The mixture was neutralized with 1N $NH_4OH$ to pH=7, and the solvent evaporated in vacuo. The residue was crystallized from EtOH to give 17 (137 g, 94%) as a white solid. $^1$H-NMR (DMSO-$d_6$) δ 1.28 (3H, s, $CH_3$), 1.48 (3H, s, $CH_3$), 3.59 (2H, m, H-5'a and H-5'b), 4.12 (1H, br q, H-4'), 4.75 (1H, dd, H-3', J=3.6, J=6.4 Hz), 4.92 (1H, dd, H-2', J=2.4, J=6.0 Hz), 5.32 (1H, t, J=5.2 Hz), 5.83 (1H, d, H-1', J=2.8 Hz), 8.38 (1H, s, H-6), 11.92 (1H, s, NH).

Example 9

5'-O-Benzoyl-2',3'-O-isopropylidine-5-bromouridine.

Benzoyl chloride (7.7 mL, 66.1 mmol) was added dropwise to a solution of 17 (12 g, 33.0 mmol) in pyridine (50 mL) at 0° C. The mixture was stirred at room temperature for 3 h, and then the reaction was quenched with ice-$H_2O$ and stirred for a further 30 min. The solvent was evaporated and co-evaporated with toluene. The residue was partitioned between EtOAc and H$_2$O. The organic phase was washed with sat. NaHCO$_3$ and H$_2$O and dried over MgSO$_4$. The solvent was evaporated to give a white solid (13.0 g, 84%) which was crystallized from MeOH. $^1$H-NMR (CDCl$_3$) δ 8.70 (1H, br s, NH), 8.01 (2H, m, Bz), 7.65-7.45 (3H, m, Bz), 5.74 (1H, d, H-1'), 4.99 (1H, dd, 5' a), 4.91 (1H, dd, 5'b), 4.65-4.53 (3H, m, H2', H-3', and H-4'), 1.60 (3H, s, CH$_3$), 1.39 (3H, s, CH$_3$).

Example 10

5'-O-(4-Fluorobenzoyl)-2',3'-O-isopropylidine-5-bromouridine

4-Fluorobenzoyl chloride (0.9 mL, 7.6 mmol) was added dropwise to a solution of 17 (2.5 g, 6.88 mmol) in pyridine (20 mL) at 0° C. The mixture was stirred at room temperature for 1 h, and then the reaction was quenched with ice-H$_2$O and stirred for a further 30 min. The solvent was evaporated and co-evaporated with toluene. The residue was partitioned between EtOAc and H$_2$O. The organic phase was washed with sat. NaHCO$_3$ and H$_2$O and dried over MgSO$_4$. The solvent was evaporated, and the residue purified by a flash silica gel column (eluant: 20% EtOAc in hexanes) to give 5'-O-4-fluorobenzoyl-2',3'-O-isopropylidine-5-bromouridine as a white solid (2.91 g, 87%). $^1$H-NMR (DMSO-d$_6$) δ 11.93 (1H, br s, NH), 8.14 (1H, s, H-6), 8.03 (2H, dd, F-Bz), 7.35 (2H, dd like t, F-Bz), 5.79 (1H, d, H-1'), 5.14 (1H, d, H-2'), 4.92 (1H, br dd, H-5' a), 4.52 (1H, dd, 5'b, J=3.6, J=11.6 Hz), 4.46-4.39 (2H, m, H-3' and H-4'), 1.50 (3H, s, CH$_3$), 1.31 (3H, s, CH$_3$).

Example 11

5'-Azido-5'-deoxy-2',3'-O-isopropylidine-5-bromouridine (19)

To a solution of 17 (3 g, 8.3 mmol) in dry pyridine (20 mL) was added MsCl (0.7 mL, 9.1 mmol) at 0° C. The mixture was stirred for 1 h at 0° C., then another (0.12 ml) MsCl was added, and the stirring continued for 1 h. The solvent was evaporated and coevaporated with toluene 2 times, and the residue partitioned between CH$_2$Cl$_2$ and H$_2$O. The organic layer was separated and dried over MgSO$_4$, and the solvent removed in vacuo to give 18 as a pale yellow foam, which was used in the next step without further purification. NaN$_3$ (2.15 g. 33.2 mmol) was added to a solution of the foam in DMF (20 mL), and the mixture heated for 2 h at 80° C. After cooling to room temperature, the mixture was concentrated in vacuo, and the residue purified by a flash silica gel column (eluant: 5% MeOH in CHCl$_3$) to give 19 (2.78 g, 86%) as a colorless solid which was crystallized from EtOH in hexanes. $^1$H-NMR (DMSO-d$_6$) 11.96 (1H, s, NH), 8.27 (1H, s, H-6), 5.81 (1H, s, H-1'), 5.13 (1H, br dd, H-2'), 4.76 (1H, dd, H-3', J=4.4, J=6.0 Hz), 4.15 (1H, q, H-4'), 3.60 (2H, br d, H-5'a and H-5'b), 1.49 (3H, s, CH$_3$), 1.29 (3H, s, CH$_3$).

Example 12

9,5'Cyclo-3-(2',3'O-isopropylidine β-D-ribofuranosyl)-8-azaxanthine (14, Y=OH, Z=N). Method A.

A solution of 19 (1 g, 2.58 mmol) in DMF (10 mL) was heated for 30 h at 110-120° C. The solvent was removed in vacuo, and the residue partitioned between EtOAc and H$_2$O. The organic layer was dried over MgSO$_4$ and evaporated to leave a pale crystalline residue. Recrystallization from MeOH and EtOAc gave 14 (602 mg, 76%) as a colorless solid. $^1$H-NMR (DMSO-d$_6$) δ 11.67 (1H, s, NH), 6.30 (1H, s, H-1'), 5.21 (1H, d, H-5' a), 4.95-4.89 (3H, m, H-2', H-3', and H-4'), 4.61 (1H, d, H-5'b), 1.45 (3H, s, CH$_3$), 1.24 (3H, s, CH$_3$).

Method B.

A mixture of 5'-O-benzoyl-2',3'-O-isopropylidine-5-bromouridine (3.82 g, 8.22 mmol) and NaN$_3$ (3.2 g, 49.2 mmol) in DMF (30 mL) was heated for 3 days at 110-120° C. The mixture was cooled to room temperature, and the insoluble material removed by filtration. The filtrate was concentrated to dryness, and the residue worked up as above to give 14 (2.0 g, 79%).

Method C.

A mixture of 5'-O-4-fluorobenzoyl-2',3'-O-isopropylidine-5-bromouridine (23 g, 47.4 mmol) and NaN$_3$ (4.6 g, 71.1 mmol) in DMF (500 mL) was heated for 5 days at 110-120° C. The mixture was cooled to room temperature, and the insoluble material removed by filtration. The filtrate was concentrated to dryness, and the residue partitioned between EtOAc and H$_2$O. The organic layer was evaporated, and the residue crystallized from MeOH and EtOAc to give 19 (9.04 g, 62.2%). The aqueous layer was evaporated to dryness, and the residue combined to that obtained from evaporation of the mother liquor of the organic layer and purified by a flash silica gel column (hexanes:EtOAc, 1:1.5) to give 2.1 g, 14.5% of 14 to make the total yield 76.7%.

Example 13

9,5'Cyclo-3-(β-D-ribofuranosyl)-8-azaxanthine (15, V=OH, Z=N)

A solution of 14 (4.1 g, 13.35 mmol) in THF:1 N HCl (1:1, 40 mL) was heated at 90° C. for 4 h. Upon cooling the mixture to room temperature, white crystals separated, which were collected, washed with cold water, and dried in vacuo to give 15 (15 g, 98%). $^1$H-NMR (DMSO-d$_6$) δ 11.59 (1H, s, NH), 5.98 (1H, s, H-1'), 5.74 (1H, d, 2'-OH, J=4.8 Hz), 5.39 (1H, d, 3'-OH, J=7.2 Hz), 4.98 (1H, d, H5'a, J=13.6 Hz), 4.80 (1H, dd, H5'b, J=13.6, J=4.0 Hz), 4.56 (1H, dd like t, H-2), 4.16-4.06 (2H, m, H-3' and H-4').

Example 14

6-Amino-1-(2',3',5'-tri-O-benzoyl-β-D-ribofuranosyl)cytosine (21)

A mixture of 6-aminocytosine (1.00 g, 5.71 mmol) and HMDS (10 mL) was refluxed for 3 h and concentrated to give a solid, which was dissolved in anhydrous CH$_2$Cl$_2$ (15 mL). To the solution were added 1-O-acetyl-2,3,5-tri-O-benzoyl-D-ribose (1.92 g, 3.81 mmol) and TMSOTf (1.66 mL, 8.59 mmol) at 0° C., and the mixture was stirred at room temp. for 12 h and poured into saturated sodium bicarbonate solution with vigorous stirring. The mixture was extracted with CHCl$_3$ (150 mL×2), the combined extracts dried (Na$_2$SO$_4$) and concentrated in vacuo, and the residue purified by silica gel column chromatography (CHCl$_3$:MeOH=30:1) to give compound 21 (1.18 g, 54%) as a white foam. $^1$H NMR (DMSO-d$_6$) δ 7.97-7.40 (m, 15H), 6.18 (s, 1H), 6.18 (m, 3H), 5.10 (s, 1H), 4.65 (m, 3H).

Example 15

1-(1',3',5'-tri-O-Benzoyl-β-D-ribofuranosyl)-5,6-diaminocytosine (23)

To a mixture of compound 21 (4.00 g, 7.01 mmol) in $H_2O$—AcOH (2: 20 mL) was added $NaNO_2$ (551 mg, 7.99 mmol) at <10° C., and the mixture was stirred at –0° C. for 5 h. After concentration of the mixture to dryness, the residue, crude 22, was washed with water and suspended in DMF-$H_2O$ (50:50 mL). Sodium hydrosulfite (4.88 g, 28.03 mmol) was added to the suspension, and the mixture refluxed at 150° C. for 2 h during which product was precipitated. The precipitates were collected by filtration and dried under high vacuum to give compound 23 (3.10 g, 73%, crude) as a green solid.

Example 16

6-Amino-3-(2',3',5'-tri-O-benzoyl-β-D-ribofuranosyl)-2-oxopurine (24)

To a solution of 23 (2.23 g, 3.81 mmol) in anhydrous DMF was added $POCl_3$ (0.58 mL, 6.22 mmol) slowly at room temperature. The mixture was stirred at room temperature for 30 min, and then poured into saturated sodium bicarbonate solution with vigorous stirring for 10 min, and extracted with $CH_2Cl_2$ several times. The combined organic extracts were dried, concentrated, and purified on a silica gel column ($CHCl_3$:MeOH=30:1 to 10:1) to give compound 24 (270 mg, 12%). FAB HRMS estimated 594.1625, observed 594.1626 (M-H) for $C_{31}H_{24}N_5O_8$.

Example 17

6-Amino-3-(2',3'-di-O-isopropylidene-β-D-ribofuranosyl)-2-oxopurine (25)

A mixture of compound 24 (270 mg, 0.453 mmol) and n-butylamine (3 mL) in MeOH (20 mL) was stirred at room temperature for 24 hr, concentrated, washed with EtOAc, and dried by high vacuum to give a solid, which was treated with 2,2-dimethoxypropane and TsOH in acetone. The mixture was stirred at room temperature for 24 hr, neutralized with triethylamine, concentrated, and purified on a silica gel column ($CHCl_3$:MeOH=10:1) to give compound 25 (95 mg, 65%) as a solid.

Example 18

6-Amino-5',9-cyclo-3-(2',3'-di-O-isopropylidene-β-D-ribofuranosyl)-2-oxo-purine (26)

To a solution of compound 25 (50 mg, 0.16 mmol) and triphenylphosphine (42 mg, 0.16 mmol) in DMF was added slowly DEAD (25 µL, 0.16 mmol) at room temperature. The resulting mixture was concentrated, and the residue purified by silica gel column chromatography ($CHCl_3$:MeOH 10:1 to 5:1) to give compound 26 (20 mg, 55%) as a solid. $^1H$ NMR (DMSO-$d_6$) δ 7.56 (s, 2H), 6.42 (s, 1H), 4.83 (d, 1H, J=5.6 Hz), 4.76 (d, 1H, J=3.2 Hz), 4.71 (d, 1H, J=13.6 Hz), 4.56 (d, 1H, J=5.6 Hz), 4.19 (dd, 1H, J=3.6, 13.6 Hz), 1.45 (s, 3H), 1.24 (s, 3H).

Example 19

6-Amino-5',9-cyclo-3-(β-D-ribofuranosyl)-2-oxo-purine HCl salt (27).

Compound 26 (20 mg, 0.065 mmol) was dissolved in 5N HCl (1 mL). After stirring at room temperature for 2 hr, the mixture was concentrated, co-evaporated with MeOH (3 mL×3), and triturated with MeOH to give crystalline 27, which was collected and dried under high vacuum (10 mg, 51%). UV $\lambda_{max}$ 245, 287 nm (MeOH); $^1H$ NMR (DMSO-$d_6$) δ 9.81 (br s, 1H), 8.65 (br s, 1H), 8.15 (s, 1H), 6.12 (s, 1H), 5.80 (s, 1H), 5.45 (s, 1H), 4.73 (d, 1H, J=14 Hz), 4.55 (m, 1H), 4.48 (dd, 1H, J=3.6, 13.6 Hz), 4.12 (m, 2H); FAB HRMS estimated 300.0500, observed 300.0497 (M-H) for $C_{10}H_{11}ClN_5O_4$.

Example 20

5-Bromo-1-(2',3'-di-O-isopropylidene-β-D-ribofuranosyl)uridine (28, R=H)

To a solution of uridine (5.00 g, 20.48 mmol) in water (130 mL) was added $Br_2$ (1.36 mL, 26.46 mmol) dropwise at room temperature. The reaction mixture was stirred at room temperature for 15 hr, concentrated at 35° C., and the residue co-evaporated several times with ethanol to give a crystalline solid, which was dissolved in acetone (50 mL) containing 2,2-dimethoxy-propane (30 mL). The reaction mixture was stirred at room temperature for 2 hr and concentrated to give a solid, which was washed with acetone-hexane (1:3) to afford compound 28 (R=H) as a gray solid (5.16 g, 69%).

Example 21

5',6-O-Cyclo-1-(2',3'-di-O-isopropylidene-β-D-ribofuranosyl)barbituric acid (29)

To a solution of potassium tert-butoxide in anhydrous ethanol (100 mL) was added compound 28 (R=Ts, 2.0 g, 5.51 mmol) at room temp. under a nitrogen atmosphere. The resulting reaction mixture was refluxed for 2 hr, cooled, diluted with water (100 mL), neutralized by acetic acid, extracted, and purified by silica gel column chromatography ($CHCl_3$:MeOH=30:1) to give compound 29 (1.0 g, 64%) as a white solid. UV $\lambda_{max}$ 260 nm (MeOH).

Example 22

6-Amino-2',3'-di-O-isopropylidene uridine (30)

A mixture of compound 29 (1.00 g, 3.54 mmol) and WWI (500 mg) in liquid ammonia was sealed in a steel bomb, and then heated at 60° C. for 15 hr. The reaction mixture was cooled, concentrated, and purified by silica gel column chromatography ($CHCl_3$:MeOH=10:1) to give compound 30 (255 mg, 24%) as a white foam. UV $\lambda_{max}$ 270 nm (MeOH); $^1H$ NMR (DMSO-$d_6$) δ 10.60 (s, 1H), 6.85 (s, 2H), 6.15 (d, 1H, J=3.2 Hz), 5.38 (t, 1H, J=4.4 Hz), 5.07 (dd, 1H, J=3.2, 6.4 Hz), 4.79 (dd, 1H, J=4.4, 6.4 Hz), 4.63 (s, 1H), 4.00 (m, 1H), 3.61 (m, 2H).

Example 23

3-(2',3'-di-O-Isopropylidene-β-D-ribofuranosyl)xanthine (33)

To a solution of compound 30 (530 mg, 1.77 mmol) and $NaNO_2$ (244 mg, 3.54 mmol) in dioxane-water was added 5N HCl slowly to pH 5 at 0° C. The resulting mixture was stirred for 10 min, neutralized with saturated sodium bicarbonate solution, and concentrated to give a purple solid. The solid was dissolved in methanol, and insoluble material removed by filtration. The filtrate was concentrated, and the residue suspended in water and treated with $Na_2S_2O_4$ (1.0 g, 5.74 mmol). The mixture was refluxed for 30 min (by this time, the color of reaction solution became green), concentrated, and purified by silica gel column chromatography ($CHCl_3$:MeOH=5:1) to give compound 32 (830 mg, crude). Crude 32 was suspended in diethoxymethyl acetate-DMF (10:10 mL), heated at 90° C. for 2 hr and 150° C. for 30 min, and cooled. After concentration in vacuo, the residue was dissolved in water, heated for 20 min, cooled, neutralized with saturated sodium bicarbonate solution, concentrated, and the residue purified by silica gel column chromatography ($CHCl_3$:MeOH=10:1) to give compound 33 (200 mg, 35%).

Example 24

5',9-Cyclo-3-(2,3-di-O-isopropylidene-β-D-ribofuranosyl)xanthine (34)

To a mixture of 33 (130 mg, 0.40 mmol) and triphenylphosphine (316 mg, 1.21 mmol) in anhydrous dioxane (5 mL) was added DEAD (0.19 mL, 1.21 mmol) slowly at room temperature, and the mixture was stirred at room temperature for 30 min, concentrated, and purified on a silica gel column ($CHCl_3$:MeOH=10:1) to give compound 34 (85 mg, 68%) as a white solid. UV $\lambda_{max}$ 236, 265 nm (MeOH); $^1$H NMR (DMSO-$d_6$) δ 11.27 (s, 1H), 7.72 (s, 1H), 6.33 (s, 1H), 4.87-4.81 (m, 3H), 4.74 (d, 1H, J=14.0 Hz), 4.19 (dd, 1H, J=4.0, 14.4 Hz), 1.45 (s, 3H), 1.24 (s, 3H); $^{13}$C NMR (DMSO-$d_6$) δ 157, 149, 138, 118, 112, 90, 85, 83, 81, 52, 26, 24.

Example 25

5',9-Cyclo-3-(β-D-ribofuranosyl)xanthine (35)

Compound 34 (50 mg, 0.16 mmol) was dissolved in 5N HCl (1 mL), stirred at room temperature for 2 hr, concentrated, co-evaporated with MeOH (3 mL×3), and triturated with MeOH. Compound 35 precipitated as colorless crystals, which were collected and dried under high vacuum (14 mg, 98%). UV $\lambda_{max}$ 238, 264 nm (MeOH); $^1$H NMR (DMSO-$d_6$) δ 11.26 (s, 1H), 7.84 (s, 1H), 6.18 (br s, 2H), 6.04 (s, 1H), 4.65 (d, 1H, J=12.8 Hz), 4.51 (m, 1H), 4.39 (dd, 1H, J=3.2, 13.6 Hz), 4.14 (t, 1H, J=5.2 Hz), 4.041 (d, 1H, J=4.8 Hz); FAB HRMS estimated 265.0573, observed 265.0574 (M-H) for $C_{10}H_9N_4O_6$.

Example 26

5'-Azido-2',3'-O-isopropylidene uridine (36)

A mixture of uridine (10 g, 44.60 mmol), 2,2-dimethoxypropane (6 mL), and TsOH (cat amt) in acetone (200 mL) was refluxed for 1 hr, neutralized by triethylamine, and concentrated to dryness. The residue was dissolved in anhydrous methylene chloride (130 mL) containing anhydrous pyridine (50 mL) and TsCl (13.0 g, 68.19 mmol). The mixture was stirred at room temperature for 15 hr, diluted with methylene chloride, washed with cold water several times, dried with sodium sulfate, concentrated, and dried by high vacuum. The residue was dissolved in anhydrous DMF (100 mL) and treated with sodium azide (5.80 g, 89.22 mmol) at 80° C. for 24 hr. The mixture was concentrated, and the residue purified by silica gel column chromatography ($CHCl_3$:MeOH=30:1) to give compound 36 (7.6 g, 55%) as a solid.

Example 27

5'Azido-5-bromo-2',3'-aisopropylidene uridine (19) from 36

A mixture of 36 (2.30 g, 7.44 mmol), ammonium cerium nitrate (6.52 g, 11.89 mmol), and LiBr (768 mg, 8.84 mmol) in anhydrous acetonitrile (120 mL) was heated at 80° C. for 30 min, neutralized by triethylamine, and concentrated. The residue was partitioned between water and chloroform. The aqueous layer was extracted with chloroform, the combined extracts concentrated, and the residue purified on a silica gel column ($CHCl_3$:MeOH=30:1) to give compound 19 (2.23 g, 77%). $^1$H NMR (CDCl$_3$) δ 8.80 (br s, 1H), 7.67 (s, 1H), 5.66 (d, 1H, J=2.0 Hz), 4.86 (m, 1H), 4.73 (m, 1H), 4.21 (m, 1H), 3.59 (m, 2H), 1.51 (s, 3H), 1.29 (m, 3H).

Example 28

6-Amino-5',6-N-Cyclo-2',3'-aisopropylidene uridine (37)

A mixture of 33 (1.83 g, 4.70 mmol) and triphenylphosphine (1.48 g, 5.64 mmol) in anhydrous THF (50 mL) was stirred at room temperature for 6 hr. Then 29% ammonium hydroxide (20 mL) was added, and the mixture stirred at room temperature for 15 hr, concentrated, and co-evaporated with toluene. The residue was dissolved in anhydrous pyridine, refluxed for 1 hr, concentrated, and the residue purified by silica gel column chromatography ($CHCl_3$:MeOH=10:1) to give 37 (1.10 g, 82%). $^1$H NMR (DMSO-$d_6$) δ 10.85 (s, 1H), 6.86 (d, 1H, J=6.8 Hz), 6.37 (s, 1H), 4.91 (s, 1H), 4.73 (dd, 2H, J=5.6, 8.0 Hz), 4.45 (s, 1H), 3.34 (m, 1H), 2.99 (d, 1H, J=13.2 Hz), 1.41 (s, 3H), 1.26 (s, 3H).

Example 29

5',6-N-Cyclo-5,6-diamino-2',3'-O-isopropylidene uridine (38)

To a solution of 37 (900 mg, 3.04 mmol) and NaNO$_2$ (392 mg, 5.68 mmol) in dioxane-H$_2$O (32:8 mL) was added conc. HCl at 0° C. slowly to pH 5. The mixture was stirred for 10 min, neutralized with saturated sodium bicarbonate solution, and concentrated. The residue was dissolved in water-DMF (10:10 mL), refluxed with Na$_2$S$_2$O$_4$ (1.60 g, 9.20 mmol) for 40 min, concentrated, and the residue purified by silica gel column chromatography ($CHCl_3$:MeOH=5:1) to give 38 (800 mg, 88%). UV $\lambda_{max}$ 288 nm (MeOH); $^1$H NMR (DMSO-$d_6$) δ 11.20 (br s, 1H), 6.75 (d, 1H, J=6.8 Hz), 6.39 (s, 1H), 5.46 (s, 2H), 4.78 (d, 1H, J=5.6 Hz), 4.68 (d, 1H, J=5.6 Hz), 4.44 (s, 1H), 3.51 (m, 1H), 2.91 (m, 1H).

Example 30

5',9-Cyclo-3-(2',3'-O-isopropylidene-β-D-ribofuranosyl)xanthine (34) from 38

A solution of 38 (800 mg, 2.70 mmol) in anhydrous mixture of DMF and diethoxy acetate (5:5 mL) was heated at 90° C. for 2 hr, neutralized with saturated sodium bicarbonate solution, concentrated, and purified by silica gel column chromatography ($CHCl_3$:MeOH=5:1) to give compound 34 (554 mg, 67%).

Example 31

5',9-Cyclo-3-(2',3'-O-isopropylidene-β-D-ribofuranosyl)-6-thioxanthine (39)

A mixture of 34 (50 mg, 0.13 mmol) and Lawesson's reagent (64 mg, 0.16 mmol) in 1,2-dichloroethane (8 mL) was refluxed for 15 hr, concentrated, and the residue purified by silica gel column chromatography ($CHCl_3$:MeOH=30:1) to give compound 39 (34 mg, 78%).

Example 32

5',9-Cyclo-3-(β-D-ribofuranosyl)-6-thioxanthine (40)

A solution of 39 (34 mg, 0.16 mmol) in 5N HCl (1 mL) was stirred at room temperature for 2 hr, concentrated, co-evaporated with MeOH (3 mL×3), and triturated with MeOH. The precipitated crystals of 40 were collected and dried under high vacuum (15 mg, 50%). UV $\lambda_{max}$ 256, 341 nm (MeOH); $^1$H NMR (DMSO-$d_6$) δ 12.37 (s, 1H), 7.84 (s, 1H), 6.03 (s, 1H), 4.59 (d, 1H, J=13.6 Hz), 4.48 (m, 1H), 4.41 (dd, 1H, J=3.6, 14.0 Hz), 4.15 (t, 1H, J=4.8 Hz), 4.04 (d, 1H, J=5.2 Hz).

Example 33

5',9-Cyclo-3-(β-D-ribofuranosyl)-2-oxo-purine (41)

A mixture of 34 (110 mg, 0.36 mmol) and Lawesson's reagent (220 mg, 0.54 mmol) in 1,2-dichloroethane (15 mL) was refluxed for 15 hr, concentrated, and the residue purified by silica gel column chromatography ($CHCl_3$:MeOH=30:1) to give 39 (85 mg), which was treated with Raney Ni (ca 200 mg) in water (5 mL) at reflux for 1.5 hr. The mixture was cooled, filtered, concentrated, and purified by silica gel column chromatography ($CHCl_3$:MeOH=10:1 v/v) to give a 6-deoxo intermediate, which was dissolved in 5N HCl (2 mL) and stirred at room temperature for 2 hr, concentrated, co-evaporated with MeOH (3 mL×3), and triturated with MeOH to crystallize 41. After being dried under high vacuum the yield of 41 was 35 mg, 39%. $^1$H NMR (DMSO-$d_6$) δ 8.59 (s, 1H), 7.57 (s, 1H), 5.96 (s, 1H), 4.72 (d, 1H, J=14 Hz), 4.47 (s, 1H), 4.36 (m, 1H), 4.12 (m, 1H), 3.98 (d, 1H, J=5.2 Hz).

Example 34

5',9-Cyclo-7-deaza-3-(2',3'-O-isopropylidene-β-D-ribofuranosyl)xanthine (42)

To a mixture of 37 (100 mg, 0.36 mmol) and NaOAc (35 mg, 0.42 mmol) in EtOH (2 mL) were added chloroacetaldehyde (0.16 mL, 2.5 mmol) and NaOAc (75 mg) at 70° C. The mixture was refluxed for 15 hrs, concentrated, and purified by silica gel column chromatography ($CHCl_3$:MeOH=10:1 v/v) to give 42 (35 mg, 32%). UV $\lambda_{max}$ 254, 328 nm (MeOH); $^1$H NMR (DMSO-$d_6$) δ 8.29 (s, 1H), 7.40 (d, 1H, J=2.8 Hz), 6.89 (d, 1H, J=2.8 Hz), 6.83 (s, 1H), 4.69 (dd, 2H, J=5.6, 12.8 Hz), 4.57 (s, 1H), 3.64 (m, 1H), 3.34 (buried by solvent peak, 1H).

Example 35

5',9-Cyclo-7-deaza-3-(β-D-ribofuranosyl)xanthine (43)

A solution of 42 (35 mg, 0.11 mmol) in 70% trifluoroacetic acid (2 mL) was stirred at room temperature for 24 hr, concentrated, and purified by silica gel column chromatography ($CHCl_3$:MeOH=10:1 v/v) to give compound 43 (22 mg, 73%). UV $\lambda_{max}$ 254, 328 nm (MeOH); $^1$H NMR (DMSO-$d_6$) δ 8.30 (s, 1H), 7.39 (d, 1H, J=2.4 Hz), 6.89 (d, 1H, J=2.4 Hz), 6.68 (s, 1H), 4.38 (s, 1H), 4.08 (d, 1H, J=6.0 Hz), 4.02 (d, 1H, J=6.4 Hz), 3.59 (dd, 1H, J=6.0, 14.0 Hz), 3.31 (buried by solvent peak, 1H).

Example 36

1-(2',3',5'-Tri-O-benzoyl-β-D-ribofuranosyl)-6-oxo-cytosine (49)

A mixture of 6-aminouracil (2.00 g, 15.74 mmol) and HMDS (20 mL) was refluxed for 3 h and concentrated to give a solid, which was dissolved in anhydrous $CH_2Cl_2$ (30 mL). 2,3,5-tri-O-Benzoyl-pentoribosyl acetate (5.30 g, 10.51 mmol) and TMSOTf (4.56 mL, 23.59 mmol) were added to the solution at 0° C., and the mixture was stirred at room temperature for 12 h. The mixture was poured into saturated sodium bicarbonate solution with vigorous stirring, extracted with $CHCl_3$ (300 mL×2), dried ($Na_2SO_4$), and purified by silica gel column chromatography ($CHCl_3$:MeOH=30:1 v/v) to give compound 49 (4.94 g, 82%) as a white foam. UV $\lambda_{max}$ 270 nm (MeOH); $^1$H NMR (DMSO-$d_6$) δ 10.75 (s, 1H), 8.00-7.31 (m, 15H), 6.52 (br s, 2H), 6.06 (m, 1H), 4.62 (m, 2H), 4.64-4.46 (m, 5H).

Example 37

5-Amino-1-(2',3',5'-Tri-O-benzoyl-β-D-ribofuranosyl)-6-oxocytosine (50)

To a solution of 49 (238 mg, 0.42 mmol) in AcOH—$H_2O$ (5: 0.5 mL) was added $NaNO_2$ over 10 min at −5° C. The resulting mixture was stirred at −5° C. for 1 hr, concentrated, and co-evaporated with toluene to give a purple solid, which was treated with acetic acid (5 mL) and Zn dust (460 mg, 7.04 mmol), and heated at 70° C. for 30 mm. The mixture was filtered through a Celite pad, and the filtrate concentrated to a slightly green solid, which was purified by silica gel column chromatography ($CHCl_3$:MeOH=10:1 v/v) to give compound 50 (217 mg, 88%).

Example 38

1-(2',3',5'-Tri-O-benzoyl-β-D-ribofuranosyl)xanthine (51)

A mixture of 50 (4.30 g, 7.33 mmol), TsOH (catalytic amount), and triethylorthoformate (90 mL) was stirred at room temperature for 24 hr, concentrated, and the residue purified on a silica gel column ($CHCl_3$:MeOH=30:1 v/v) to give compound 51 (2.20 g, 50%).

Example 39

1-(β-D-Ribofuranosyl)xanthine (52)

A solution of compound 51 (500 mg, 0.84 mmol) in saturated methanolic ammonia (10 mL) was stirred at room temperature for 24 hr, concentrated to dryness, washed with EtOAc several times, and dried to give 52 (200 mg, 84%) as a white solid.

Example 40

1-(2',3'-Di-O-isopropylidene-β-D-ribofuranosyl) xanthine (53)

A mixture of 52 (150 mg, 0.53 mmol), 2,2-dimethoxypropane (2 mL), acetone (15 mL), and TsOH (catalytic amount) was refluxed for 2 hr, cooled, neutralized by triethylamine, concentrated, and purified by silica gel column chromatography ($CHCl_3$:MeOH=10:1 to 4:1 v/v) to give 53 (100 mg, 58%).

Example 41

5',2-O-Cyclo-1-(β-D-ribofuranosyl)xanithine (54)

To a solution of 53 (150 mg, 0.46 mmol) and triphenylphosphine (400 mg, 1.53 mmol) in anhydrous DMF (3 mL) was added DEAD (0.24 mL, 1.52 mmol), and the mixture was stirred at room temperature for 1 hr, concentrated, and purified by silica gel column chromatography ($CHCl_3$:MeOH=30:1 to 10:1 v/v) to give 129 mg (92%) of the 2',3'-di-O-benzoylated product, which (0.42 mmol) was dissolved in 5N HCl (2 mL), stirred at room temperature for 2 hr, concentrated, co-evaporated with MeOH (4 mL×3), and triturated with MeOH. Compound 54 crystallized and was collected and dried under high vacuum (34 mg, 31%).

Example 42

1-(2'-O-Acetyl-3'-deoxy-5'-O-methoxycarbonyl-β-D-erythropentofuranosyl)-5-nitropyridine-2-one (56)

TMS-trifiate (1.486 ml, 8.2 mmol, 1.5 eq.) was added to the silylated 2-hydroxy-5-nitropyridine (997 mg, 7.1 mmol, 1.3 eq.) and 1,2-di-O-acetyl-5-O-carbomethoxy-3-deoxy-xylofuranose (55, 1.512 g, 5.47 mmol, 1 eq.) in anhydrous 1,2-dichloroethane (55 ml) at 0° C. The solution was stirred at room temperature for 8 h. $NaHCO_3$ and $CH_2Cl_2$ were added, and the resulting mixture partitioned. The organic layer was washed with water, dried ($Na_2SO_4$), and the solvents removed in vacuo. The residue was chromatographed on a column of silica gel with a stepwise gradient of MeOH (0 to 1%) in $CH_2Cl_2$ to give compound 56 as a pale yellow solid (1.550 g, 79.5%).

Example 43

1-(2',5'-Di-O-benzoyl-3'-deoxy-β-D-erythropentofuranosyl)-5-nitropyridine-2-one (58)

To a solution of 56 (512 mg, 1.45 mmol, 1 eq.) in MeOH (14.5 ml) was added MeONa (157 mg, 2.9 mmol, 2 eq.). The solution was stirred at room temperature for 1 h, and then neutralized by addition of a 6N HCl solution in water to pH 7. The solvent was removed in vacuo, and the crude free nucleoside 57 thus obtained was coevaporated several times with anhydrous toluene. Pyridine was added, and the mixture cooled to 0° C. Benzoyl chloride (0.503 ml, 4.36 mmol, 3 eq.) was added dropwise, and the solution stirred at room temperature for 2 h. Pyridine was removed in vacuo, and the residue, dissolved in $CH_2Cl_2$, was successively washed with a saturated $NaHCO_3$ solution and water. The organic layer was dried ($Na_2SO_4$), filtered, and the filtrate concentrated in vacuo. The residue was chromatographed on a column of silica gel with a stepwise gradient of MeOH (0 to 1%) in $CH_2Cl_2$ to afford 58 as a pale brown solid (yield 656 mg, 97%).

Example 44

9,5'-Cyclo-3-(2'-O-benzoyl-3'-deoxy-β-D-erythropentofuranosyl)-1-deaza-8-azapurine-2-one (59)

A solution of 58 (650 mg, 1.4 mmol, 1 eq.) in DMF (22.4 ml) was stirred at 115° C. for 4 days in presence of sodium azide (137 mg, 2.1 mmol, 1.5 eq.). The solvent was removed in vacuo, and 2N HCl and $CH_2Cl_2$ were added. The two layers were separated, and the aqueous phase extracted with $CH_2Cl_2$. The combined organic layers were dried ($Na_2SO_4$) and concentrated in vacuo. The residue was chromatographed on a column of silica gel with an isocratic of 50% EtOAc in hexane to afford 59 as a white solid (yield 252 mg, 53.5%).

Example 45

9,5'-Cyclo-3-(3'-deoxy-β-D-erythropentofuranosyl)-1-deaza-8-azapurine-2-one (60)

To a solution of 59 (252 mg, 0.7 mmol, 1 eq.) in MeOH (7 ml) was added MeONa (80.5 mg, 1.5 mmol, 2 eq.), and the mixture was stirred at room temperature for 1 h. MeONa was neutralized by addition of 6N HCl to pH 7. Silica was added, and the solvent removed under reduced pressure. The residue was chromatographed on a column of silica gel with a stepwise gradient of MeOH (0 to 4%) in $CH_2Cl_2$ to afford 60 as a white solid (yield 108 mg, 62%).

Example 46

9,5'-Cyclo-carba-8-azaxanthosine (65)

To a solution of compound (61, 50 mg, 0.14 mmol) in $CH_2Cl_2$ (10 mL) were added $Et_3N$ (1 mL), DMAP (224 mg, 2 mmol), and methanesulfonyl chloride (0.2 mL, 0.25 mmol), and the resulting solution was stirred at RT for 5 h. EtOAc (40 mL) was added, and the diluted solution washed with $H_2O$ (5 mL) and dried ($Na_2SO_4$). The solvent was removed to dryness. The residue, crude 62, was unstable and used directly in the next step by dissolving it in DMF (10 mL). To the solution was added $NaN_3$ (130 mg, 2 mmol), and the mixture stirred at 80° C. for 4 h. Solids were removed by filtration. The filtrate was concentrated to dryness, and the residue purified by silica gel column chromatography (3% MeOH in $CH_2Cl_2$) to give azide (63) as a syrup which was dissolved in DMF (5 mL). The resulting solution was heated at 120° C. for 3 days. Solvent was removed, and the residue, crude 64, was dissolved in MeOH (5 mL). To the solution was added HCl (1 mL, 2N in $Et_2O$), and the solution was stirred at room temperature for 5 h. Solvent was removed, and the residue purified on a silica gel column (10% MeOH in $CH_2Cl_2$) to give 65 as a solid (15 mg, 40.4% from 61). $^1H$ NMR ($CDCl_3$) δ 11.53 (br, 1H, NH, $D_2O$ exchangeable), 5.21 (d, J=3.6 Hz, 1H, OH, $D_2O$ exchangeable), 5.05 (d, J=5.6 Hz, OH, $D_2O$ exchangeable), 4.83 (d, J=5.6 Hz, 1H, 1'-H), 4.77 (d, J=12.8 Hz, 1H, 2'-H), 4.54 (dd, J=4 Hz, 13 Hz, 3'-H), 3.85 (m, 2H, 5'-H), 2.67 (m, 1H, 4'-H), 1.78, 1.29 (m, 2H, 4"-H).

Example 47

3,5% Cyclo-4-(β-D-ribofuranosyl)-vic-triazolo[4,5-b]pyridin-5-thione (70)

A mixture of 14 (R'=R"=Bz, Y=H, Z=CH, 2.0 g, 4.36 mmol) and Lawesson's reagent (2.0 g) in anhydrous dichloroethane (85 mL) was heated under reflux for 16 h. The mixture was concentrated to dryness, and the residue treated with saturated methanolic ammonia (80 mL) at room temperature for 12 h. Yellowish precipitates were collected by suction and washed with MeOH and crystallized from hot water to give 70 (910 mg, 78%) as a yellowish solid. $^1$H NMR (DMSO-$d_6$) δ 4.13 (t, J=4.4 Hz, 1H), 4.23 (m, 1H), 4.70 (t, J=4.8 Hz, 1H), 4.97 (dd, J=4.4 and 13.6 Hz, 1H), 5.11 (d, J=14 Hz, 1H), 5.43 (d, J=7.2 Hz, 1H), 5.84 (d, J=5.2 Hz, 1H), 6.88 (s, 1H), 7.31 (d, J=8.8 Hz, 1H), 7.96 (d, J=9.6 Hz, 1H). Anal. Calc'd for $C_{10}H_{10}N_4O_3S \cdot 0.2H_2O$: C, 44.50; H, 3.88; N, 20.76; Found: C, 44.25; H, 3.94; N, 20.58.

Example 48

3,5% Cyclo-6-chloro-4-(β-D-ribofuranosyl)-vic-triazolo[4,5-b]pyridin-5-one (71, X=Cl)

A mixture of 15 (R'=R"=H, Y=H, Z=CH; 94 mg, 0.38 mmol) and N-chlorosuccinimide (69 mg) in 3.5 mL of glacial acetic acid was refluxed for 30 min. The mixture was concentrated to dryness, and the residue purified by silica gel column chromatography with 1-2% MeOH in $CH_2Cl_2$ to give 71 (X=Cl) (43 mg, 40.2%) as a solid. $^1$H NMR (DMSO-$d_6$) δ 4.06 (t, J=5 Hz, 1H), 4.15 (m, 1H), 4.62 (t, J=4.2 Hz, 1H), 4.89 (dd, J=4 and 13.6 Hz, 1H), 5.05 (d, J=14 Hz, 1H), 5.42 (d, J=7.6 Hz, 1H, $D_2O$ exchangeable), 5.84 (d, J=4.8 Hz, 1H, $D_2O$ exchangeable), 6.23 (s, 1H), 8.54 (s, 1H).

Example 49

3,5'-Cyclo-6-bromo-4-(β-D-ribofuranosyl)-vic-triazolo[4,5-b]pyridin-5-one (71, X=Br)

To a stirred solution of 15 (R'=R"=H, Y=H, Z=CH; 3 g, 11.99 mmol) in $H_2O$ (60 mL) was added $Br_2$ (0.9 mL) dropwise at room temperature. The product 71 precipitated while stirring at room temperature. The precipitates were collected by suction and washed with MeOH to give 71 (X=Br, 3.35 g, 85.1%) as a solid. $^1$H NMR (DMSO-$d_6$+$D_2O$) δ 4.04 (d, J=5.2 Hz, 1H), 4.15 (t, J=4.8 Hz, 1H), 4.62 (t, J=4.4 Hz, 1H), 4.87 (dd, J=4 and 14 Hz, 1H), 5.04 (d, J=14 Hz, 1H), 6.22 (s, 1 H), 8.69 (s, 1H).

Example 50

3,5'-Cyclo-7-propylamino-4-(β-D-ribofuranosyl)-vic-triazolo[4,5-b]pyridin-5-one (72, R=H, R'=n-Pr)

A mixture of 71 (X=Br, 150 mg, 0.456 mmol) and propylamine (15 mL) was heated at 110° C. in a sealed bottle for 16 h. The mixture was cooled, and the propylamine removed in vacuo. The residue was triturated with EtOH when 72 (R=n-$C_3H_7$) precipitated (45 mg) as a white solid. $^1$H NMR (DMSO-$d_6$) δ 0.89 (t, J=7.2 Hz, 3H), 1.57 (dd, J=8 and 14.8 Hz, 2H), 3.12 (m, 2H), 3.87 (t, J=4.4 Hz, 1H), 4.08 (dd, J=5.2, 12 Hz, 1H), 4.53 (t, J=4 Hz, 1H), 4.74 (dd, J=4 and 14 Hz, 1H), 4.96 (d, J=13.2 Hz, 1H), 5.11 (s, 1H), 5.33 (d, J=7.2 Hz, 1H, $D_2O$ exchangeable), 5.67 (d, J=4.8 Hz, 1H, $D_2O$ exchangeable), 6.17 (s, 1H), 7.56 (s, 1H, $D_2O$ exchangeable).

Example 51

3,5'-Cyclo-7-methylamino-4-(β-D-ribofuranosyl)-vic-triazolo[4,5-b]pyridin-5-one (72, R=H, R'=Me)

A mixture of 71 (X=Br, 150 mg, 0.456 mmol) and 33% $MeNH_2$ in EtOH (15 mL) was heated at 110° C. in a sealed bottle for 16 h. The mixture was concentrated in vacuo, and the residue triturated with EtOH. The precipitated product was collected by suction (35 mg). $^1$H NMR (DMSO-$d_6$) δ 2.77 (d, J=4.4 Hz, 3H), 3.87 (t, J=4.8 Hz, 1H), 4.07 (dd, J=5.2, 12 Hz, 1H), 4.54 (t, J=4.4 Hz, 1H), 4.75 (dd, J=3.6 and 13.6 Hz, 1H), 4.96 (d, J=13.6 Hz, 1H), 5.05 (s, 1H), 5.34 (d, J=7.6 Hz, 1H, $D_2O$ exchangeable), 5.68 (d, J=4.8 Hz, 1H, $D_2O$ exchangeable), 6.18 (s, 1H), 7.56 (s, 1 H, $D_2O$ exchangeable).

Example 52

3,5'-Cyclo-7-ethylamino-4-(β-D-ribofuranosylyvic-triazolo[4,5-b]pyridin-5-one (72, R=H, R'=Et)

A mixture of 71 (X=Br, 150 mg, 0.456 mmol) and 75% $EtNH_2$ in $H_2O$ (15 mL) was heated at 100-110° C. in a sealed bottle for 16 h. The mixture was concentrated in vacuo, and the residue triturated with EtOH. The white precipitates were collected by suction to give 72 (R=H, R'=Et, 38 mg). $^1$H NMR (DMSO-$d_6$) δ 1.16 (t, J=4.4 Hz, 3H), 3.20 (br s, 2H), 3.87 (t, J=4.4 Hz, 1H), 4.08 (dd, J=5.2, 12.8 Hz, 1H), 4.54 (t, J=4 Hz, 1H), 4.74 (dd, J=4 and 13.6 Hz, 1H), 4.96 (d, J=13.6 Hz, 1H), 5.11 (s, 1H), 5.33 (d, J=7.2 Hz, 1H, $D_2O$ exchangeable), 5.66 (d, J=4.8 Hz, 1H, $D_2O$ exchangeable), 6.18 (s, 1H), 7.52 (t, J=5.2 Hz, 1H, $D_2O$ exchangeable).

Example 53

3,5'-Cyclo-7-(2-hydroxyethylamino)-4-(β-D-ribofuranosyl)-vic-triazolo[4,5-b]-pyridin-5-one (72, R=H, R'=$CH_2CH_2OH$)

A mixture of 71 (X=Br, 150 mg, 0.456 mmol) and ethanolamine (7 mL) was heated at 100-110° C. in a sealed bottle for 16 h. The mixture was concentrated in vacuo, and the residue triturated with EtOH to crystallize the product, which was collected by suction to give 58 mg of 72 (R=H, R'=$CH_2CH_2OH$). $^1$H NMR (DMSO-$d_6$) δ 3.23 (br s, 2H), 3.56 (dd, J=6.4, 12 Hz, 2H), 3.87 (t, J=4.8 Hz, 1H), 4.07 (dd, J=5.2, 12 Hz, 1H), 4.54 (t, J=4 Hz, 1H), 4.75 (dd, J=4 and 14 Hz, 1H), 4.79 (t, J=6 Hz, 1H, $D_2O$ exchangeable), 4.97 (d, J=14 Hz, 1H), 5.17 (s, 1H), 5.34 (d, J=7.6 Hz, 1H, $D_2O$ exchangeable), 5.68 (d, J=4.4 Hz, 1H, $D_2O$ exchangeable), 6.18 (s, 1H), 7.32 (t, J=6 Hz, 1H, $D_2O$ exchangeable).

Example 54

7-Butylamino-3,5'-cyclo-4-(β-D-ribofuranosyl)-vic-triazolo[4,5-b]pyridin-5-one (72, R=H, R'=n-$C_4H_9$)

A mixture of 71 (X=Br, 150 mg, 0.456 mmol) and butylamine (8 mL) was heated at 100-110° C. in a sealed bottle for 16 h. The mixture was concentrated in vacuo, and the residue triturated with MeOH to precipitate 72 (R=H, R'=$CH_2Ph$), which was collected by suction (42 mg). $^1$H NMR (DMSO-$d_6$) δ 0.89 (t, J=7.2 Hz, 3H), 1.33 (m, 2H), 1.53 (m, 2H), 3.15 (br s, 2H), 3.87 (t, J=4 Hz, 1H), 4.08 (dd, J=5.2, 11.6 Hz, 1H), 4.53 (t, J=3.6 Hz, 1H), 4.74 (dd, J=4 and 14 Hz, 1H), 4.96 (d, J=13.6 Hz, 1H), 5.10 (s, 1H), 5.34 (d, J=7.2 Hz, 1H, $D_2O$ exchangeable), 5.67 (d, J=4.4 Hz, 1H, $D_2O$ exchangeable), 6.17 (s, 1H), 7.55 (br s, 1H, $D_2O$ exchangeable).

Example 55

7-Amino-3,5'-cyclo-4-(β-D-ribofuranosyl)-vic-triazolo[4,5-b]pyridin-5-one (72, R=R'=H)

A mixture of 71 (X=Br, 150 mg, 0.456 mmol) and liquid ammonia (10 mL) was heated at 70° C. in a sealed bottle for

95

15 h. The sealed bottle was cooled and opened at −78° C., and 5 mL of MeOH was added. The mixture was warmed to room temperature, and the precipitated product collected (135 mg). $^1$H NMR (DMSO-$d_6$) δ 3.86 (t, J=4.8 Hz, 1H), 4.07 (dd, J=5.2, 11.6 Hz, 1H), 4.53 (t, J=4 Hz, 1H), 4.74 (dd, J=4 and 14 Hz, 1H), 4.96 (d, J=13.6 Hz, 1H), 5.16 (s, 1H), 5.34 (d, J=6.8 Hz, 1H, $D_2O$ exchangeable), 5.66 (d, J=4.8 Hz, 1H, $D_2O$ exchangeable), 6.16 (s, 1H), 6.98 (s, 2H, $D_2O$ exchangeable).

Example 56

9,5'-Cyclo-3-(2',3'-O-isopropylidine-β-D-ribofuranosyl)-6-imidazolyl-8-azapurine-2-one (73, X=imidazolyl)

A mixture of 14 (Y=OH, Z=N, R', R''=isopropylidene, 565 mg, 1.84 mmol), $PPh_3$ (1.16 g, 4.42 mmol), imidazole (0.44 g, 6.51 mmol), diisopropylethylamine (1.6 ml, 9.2 mmol), and iodine (1 g, 3.81 mmol) in toluene (15 mL) was heated for 2 h at 95-100° C. After cooling to room temperature, the mixture was concentrated in vacuo, and the residue mixed with EtOAc. Insoluble materials were filtered through a Celite pad, and the filtrate was washed with water and brine, dried ($MgSO_4$), and concentrated in vacuo. The residue was purified on a flash silica gel column (eluant: 7:3 EtOAc:hexanes) to give 73 (X=imidazolyl) as a pale yellow solid (0.536 g, 81%), which was crystallized from EtOH in hexanes. $^1$H-NMR (DMSO-$d_6$) δ 7.64 (1H, s, 6-Im), 7.11 (1H, br s, 6-Im), 6.92 (1H, br s, 6-Im), 6.37 (1H, s, H-1'), 5.23 (1H, d, H5'a, J=14 Hz), 4.92-4.81 (3H, m, H-2', H-3', and H4'), 4.66 (1H, dd, H-5'b, J=4.4, J=14 Hz), 1.47 (3H, s, $CH_3$), 1.26 (3H, s, $CH_3$).

Example 57

9,5'-Cyclo-3-(2',3'-O-isopropylidine-β-D-ribofuranosyl)-6-amino-8-azapurine-2-one (74, R=R'=H)

Triethylamine (0.35 mL, 2.48 mmol) was added to a mixture of 73 (152 mg, 0.5 mmol), DMAP (150 mg, 1.23 mmol), and triisopropylbenzenesulfonyl chloride (373 mg, 1.23 mmol) in $CH_3CN$ (10 mL) at 0° C. The mixture was stirred at room temperature for 24 h, and then treated with conc. $NH_4OH$ (20 mL). The mixture was stirred for a further 12 h, and the solvent concentrated in vacuo. The residue was purified by a flash silica gel column (eluant: EtOAc:hexanes 3:1) to give 74 (130 mg, 86%) as a pale yellow solid, which was used directly in the next step without further purification.

Example 58

9,5'-Cyclo-3-(β-D-ribofuranosyl)-6-amino-8-azapurine-2-one hydrochloride (75, R=R'=H)

A solution of 74 (120 mg, 0.39 mmol) in THF:1 N HCl (1:1, 10 mL) was heated at 90° C. for 1 h and cooled to room temperature. The solvent was evaporated and coevaporated with EtOH several times. The solid residue was crystallized from EtOH and $H_2O$ to give 75 (92 mg, 89%). $^1$H-NMR of the major isomer (DMSO-$d_6$+$D_2O$) δ 5.99 (1H, s, H-1'), 5.09 (1H, d, H5'a, J=13.6 Hz), 4.90 (1H, dd, H5'b, J=13.6, J=4.4 Hz), 4.61 (1H, t, H-4', J=4.4 Hz), 4.14-4.06 (2H, m, H-2' and H-3'); $^1$H-NMR of the minor isomer (DMSO-$d_6$+$D_2O$) δ 5.97 (1H, s, H-1'), 4.98 (1H, d, H5'a, J=14.0 Hz), 4.87 (1H, dd, H5'b, J=14.0, J=3.6 Hz), 4.56 (1H, t, H-4', J=4.4 Hz), 4.14-4.06 (2H, m, H-2' and H-3').

Example 59

9,5'-Cyclo-3-(2',3'O-thiocarbonyl-β-D-ribofuranosyl)-8-azaxanthine (82, Y=OH, Z=N)

A mixture of 9,5'-cyclo-3-β-D-ribofuranosyl)-8-azaxanthine (15, 826 mg, 3.1 mmol) and N,N-thiocarbonyldiimidazole (800 mg, 4.02 mmol) in DMF (10 mL) was heated for 2 h at 80° C. The mixture was cooled to room temperature, the solvent removed in vacuo, and the residue purified by flash silica gel column chromatography (eluant: EtOAc:$CH_2Cl_2$ 4:1) to give 82 (940 mg, 76%) as a yellowish white solid. $^1$H-NMR DMSO-$d_6$+$D_2O$) δ 6.66 (1H, s, H-1'), 5.94-5.91 (2H, m, H-2' and H-3'), 5.36 (2H, m, H-4' and H5a'), 4.71 (1H, m, H-5'b).

Example 60

9,5% Cyclo-3-(2'-deoxy-β-D-erythropentofuranosyl)-8-azaxanthine (83, Y=OH, Z=N) and 9,5'-cyclo-3-(3'-deoxyl-β-D-erythropentofuranosyl)-8-azaxanthine (84, Y=OH, Z=N)

tent-Butyl peroxide (30 μL) was added to a solution of 82 (470 mg, 1.52 mmol) and tris(trimethylsilyl)silane (1.5 mL, 2.28 mmol) in dioxane (15 mL) slowly at 80° C., and the mixture was refluxed for 2 h. The mixture was concentrated in vacuo, and the residue purified on a silica gel column (eluant: 10% MeOH in $CH_2Cl_2$) to give a 1:1 mixture (293 mg, 77%) of 83 and 84, which were partially separated by repeated silica gel chromatography. $^1$H-NMR of the latter compound (DMSO-$d_6$+$D_2O$) δ 5.99 (1H, s, H-1'), 5.15 (1H, m, H-4'), 4.84 (1H, d, H5'a, J=14 Hz), 4.74 (1H, dd, H-5'b, J=3.6 Hz, J=14 Hz), 4.32 (1H, d, H-2', J=5.2 Hz), 2.18 (1H, m, H-3' a), 1.96 (1H, m, H-3'b).

Example 61

5',3-Cyclo-2',3'-O-isopropylidene-xanthosine (91, Y=OH)

To a mixture of 2',3'-O-isopropylidene xanthosine 90 (Y=OH, 280 mg, 0.86 mmol) and triphenylphosphine (340 mg, 1.29 mmol) in anhydrous DMF (5 mL) was added DEAD (0.21 mL, 1.30 mmol) slowly at room temperature, and the mixture was stirred at room temperature for 30 min, concentrated, and purified by silica gel column chromatography ($CHCl_3$:MeOH 10:1 v/v) to give compound 91 (200 mg, 76%) as a white solid. $^1$H NMR (DMSO-$d_6$) δ 11.23 (s, 1H), 7.86 (s, 1H), 6.40 (s, 1H), 4.83 (s, 1H), 4.81 (d, 1H, J=6.0 Hz), 4.71 (dd, 1H, J=2.8, 14.8 Hz), 4.45 (d, 1H, J=6.0 Hz), 3.60 (dd, 1H, J=2.8, 14.8 Hz), 1.44 (s, 3H), 1.23 (s, 3H).

Example 62

5',3-Cyclo-xanthosine (92, Y=OH)

Compound 91 (Y=OH, 200 mg, 0.65 mmol) was treated with 5N HCl (5 mL), stirred at room temperature for 2 hr, concentrated, co-evaporated with MeOH (5 mL×3), and triturated with MeOH. Compound 92 crystallized and was collected and dried under high vacuum (142 mg, 82%) to give a yellowish solid. UV $λ_{max}$ 238, 264 nm (MeOH); $^1$H NMR (DMSO-$d_6$) δ 11.38 (s, 1H), 8.15 (s, 1H), 6.20 (s, 1H), 4.59-4.56 (m, 4H), 4.22 (dd, 1H, J=4.0, 5.6 Hz), 3.91 (d, 1H, J=6.0

Hz), 3.73 (dd, 1H, J=3.2, 14.8 Hz); FAB HRMS estimated 265.0573, observed 265.0580 (M-H) for $C_{10}H_9N_4O_6$.

Example 63

9,5'-Cyclo-1-methyl-3-(2',3'-O-isopropylidine-β-D-ribofuranosyl)-8-azaxanthine (76, R=CH$_3$)

MeI (62 μL, 1 mmol) was added to a mixture of 9,5'-cyclo-3-(2',3'-O-isopropylidine-β-D-ribofuranosyl)-8-azaxanthine (14, Y=OH, Z=N, 152 mg, 0.5 mmol) and K$_2$CO$_3$ (172 mg, 1.25 mmol) in DMF (5 mL). The mixture was stirred at room temperature for 20 h, and then the solvent was removed in vacuo. The residue was partitioned between EtOAc and H$_2$O, and the organic phase dried over (MgSO$_4$) and evaporated. The residue was purified on a silica gel column (eluant: EtOAc:hexanes 2:1) to give the title compound (150 mg, 93%) as a white solid which was crystallized from EtOAc in hexanes. $^1$H-NMR (CDCl$_3$) δ 6.68 (1H, s, H-1'), 5.05 (1H, d, H5'a, J=14 Hz), 4.92 (2H, m, H-2' and H-3'), 4.74 (1H, d, H-4', J=5.6 Hz), 4.67 (1H, dd, H-5'b, J=14, J=4 Hz), 3.41 (3H, s, N—CH$_3$), 1.58 (3H, s, CH$_3$), 1.34 (3H, s, CH$_3$).

Example 64

9,5'-Cyclo-1-methyl-3-(β-D-ribofuranosyl)-8-azaxanthine (77, R=CH$_3$)

A solution of 9,5'-cyclo-1-methyl-3-(2',3'-O-isopropylidene-β-D-ribofuranosyl)-8-azaxanthine (76, 99 mg, 0.31 mmol) in THF:1 N HCl (1:1, 10 mL) was heated at 90° C. for 3 h. The solvent was evaporated, and the residue purified by flash silica gel column chromatography (eluant: 12% MeOH in CHCl$_3$) to give 9,5'-cyclo-1-methyl-3-(β-D-ribofuranosyl)-8-azaxanthine (78 mg, 89%) as a white solid. $^1$H-NMR (DMSO-d$_6$) δ 6.03 (1H, s, H-1'), 5.77 (1H, d, 2'-OH, J=4.8 Hz), 5.42 (1H, d, 3'-OH, J=6.8 Hz), 5.03 (1H, br d, H5'a, J=15.2 Hz), 4.81 (1H, dd, H-5'b, J=14, J=4 Hz), 4.58 (1H, br dd, H-4'), 4.10 (2H, m, H-2' and H-3'), 3.20 (3H, s, N—CH$_3$).

EXMAPLE 65

1-Cyanomethyl-9,5'-cyclo-3-(2',3'-O-isopropylidine-β-D-ribofuranosyl)-8-azaxanthine (76, R=CH$_2$CN)

NaH dispersion on mineral oil (68 mg, 1.71 mmol) was added to a solution of 9,5'-cyclo-3-(2',3'-O-isopropylidine-β-D-ribofuranosyl)-8-azaxanthine (14, Y=OH, Z=N, 500 mg, 1.63 mmol) in DME:DMF (4:1, 10 mL) at 0° C. After stirring for 10 min at 0° C., LiBr (283 mg, 3.26 mmol) was added, and the suspension was stirred at room temperature for 15 min. BrCH$_2$CN (0.23 mL, 3.26 mmol) was added, and the mixture heated for 2 h at 65° C. The solvent was evaporated, and the residue partitioned between EtOAc and H$_2$O. The organic phase was dried (MgSO$_4$) and evaporated. The residue was purified by flash silica gel column chromatography (eluant: 2% MeOH in CHCl$_3$) to give the title compound (560 mg, 99%) as a white solid. $^1$H-NMR (DMSO-d$_6$) δ 6.47 (1H, s, H-1'), 5.27 (1H, d, H5'a, J=14.4 Hz), 5.01-4.87 (5H, m, H-2', H-3', and N—CH$_2$CN), 4.67 (1H, dd, H-5'b, J=14.4, J=4.0 Hz), 1.47 (3H, s, CH$_3$), 1.25 (3H, s, CH$_3$).

Example 66

1-Cyanomethyl-9,5'-cyclo-3-(β-D-ribofuranosyl)-8-azaxanthine (77, R=CH$_2$CN)

A solution of 1-cyanomethyl-9,5'-cyclo-3-(2',3'-O-isopropylidine-β-D-ribofuranosyl)-8-azaxanthine (300 mg, 0.87 mmol) in THF:1 N HCl (1:1, 10 mL) was heated for 2 h at 90° C. The solvent was evaporated to give 1-cyanomethyl-9,5'-cyclo-3-(β3-D-ribofuranosyl)-8-azaxanthine (260 mg, 98%) as a white solid which was crystallized from MeOH. $^1$H-NMR (DMSO-d$_6$+D$_2$O) δ 6.04 (1H, s, H-1'), 5.04 (1H, d, H-5'a, J=13.6 Hz), 4.91-4.81 (2H, m, H-5' b and H-4'), 4.62 (1H, m, H-3' or H-2'), 4.38 (1H, m, H-3' or H-2'), 4.20-4.06 (2H, m, N—CH$_2$CN).

Example 67

1-O-Acetyl-2,3,5-tri-O-benzoyl-β-L-ribofuranose (20, L-form)

To a solution of L-ribose (10 g, 66.6 mmol) in MeOH (200 mL) was slowly added conc. H$_2$SO$_4$ (177 μL), and the mixture was stirred for 12 h at room temperature. Dry pyridine (20 mL) was added, and the mixture concentrated in vacuo. This process was repeated 2 times, and the residue dried under vacuum to give a colorless foam, which was dissolved in dry pyridine (100 mL) and cooled to 0° C. Benzoyl chloride (50 mL, 399.6 mmol) was added drop-wise and the mixture was stirred at room temperature for 12 h. Ice-H$_2$O was added, and the mixture was stirred for 1 h. The solvent was evaporated and co-evaporated with toluene (200 mL, 2 times), and the residue partitioned between EtOAc and H$_2$O. The organic phase was washed with saturated NaHCO$_3$, H$_2$O, and brine, and dried over MgSO$_4$. The solvent was evaporated, and the residue dried under vacuum overnight. The oily residue was dissolved in AcOH (80 mL) and acetic anhydride (6.6 mL), and the mixture cooled to 0° C. Conc. H$_2$SO$_4$ (1.8 mL) was added drop-wise. The mixture was stirred at room temperature for 24 h. The solvents were evaporated in vacuo and then co-evaporated with toluene. The residual syrup was triturated with EtOH, and the solid was recrystallized from MeOH to give the title compound (19.2 g, 57%) as white crystals. $^1$H-NMR (CDCl$_3$) δ 8.02-7.24 (15H, m, BzH), 6.36 (1H, s, H-1), 5.84 (1H, dd, H-2), 5.72 (1H, d, H-3), 4.73-4.68 (2H, m, H-4 and H-5a), 4.44 (1H, m, H-5b), 1.92 (3H, s, Ac).

Example 68

1-(2',3',5'-Tri-O-benzoyl-β-L-ribofuranosyl)-5-bromouracil

A solution of 1-O-acetyl-2,3,5-tri-O-benzoyl-β-L-ribofuranose (2.3 g, 4.55 mmol) in CH$_3$CN (30 mL) was added to silylated 5-bromouracil [generated from 5-bromouracil (2.2 g, 14.3 mmol), HMDS (10 mL), and TMSCl (0.2 mL) by heating for 2 h at 80° C. followed by evaporation of the solvents], and the mixture cooled to 0° C. 1 M SnCl$_4$ (13.6 mL) was added drop-wise, and the mixture stirred for 2 h at room temperature. The mixture was diluted with CHCl$_3$ (100 mL) and quenched with cold saturated NaHCO$_3$. The mixture was filtered over a Celite pad, and the organic phase separated, dried (MgSO$_4$), and evaporated to give a white solid. The solid was washed with cold EtOAc and crystallized from EtOAc in hexanes to give the title compound (2.85 g, 98%) as a white crystals. $^1$H-NMR (CDCl$_3$) δ 8.06 (1H, br s, NH), 8.06-7.29 (15H, m, Bz) 7.68 (1H, s, H-6), 6.29 (1H, d, H-1', J=6 Hz), 5.81 (1H, m, H-3'), 5.65 (1H, t, H-2', J=6 Hz), 4.77-4.62 (3H, m, H-4', H-5'a, and 5'b).

Example 69

L-5-Bromouridine 1-(2',3',5'-Tri-O-benzoyl-β-L-ribofuranosyl)-5-bromouracil (3 g, 4.72 mmol) was dissolved in MeOH and treated with sodium methoxide 4.4 M solution in MeOH (1 mL) at 0° C., and the mixture stirred for 2 h at room temperature. The mixture was neutralized with AcOH, and the solvent evaporated in vacuo. The residue was purified on a silica gel column (eluant: EtOAc:acetone:EtOH:H$_2$O; 6:1:1:0.5) to give a white solid (1.2 g, 79%), which was crystallized from EtOH. $^1$H-NMR (DMSO-d$_6$) 11.82 (1H, s, NH), 8.48 (1H, s, H-6), 5.72 (1H, d, H-1', J=4.4 Hz), 5.44 (1H, d, 2'-OH, J=5.2 Hz), 5.29 (1H, t, J=4.8 Hz), 5.10 (1H, d, 3'-OH, J=5.2 Hz), 4.04 (1H, q, H-2', J=4.0, J=4.8 Hz), 4.02 (1H, q, H-3', J=4.0, J=4.8 Hz), 3.98 (1H, m, H-4'), 3.70 (1H, m, H-5' a), 3.57 (1H, m, H-5'b).

Example 70

1-(2',3'-O-isopropylidine-β-L-ribofuranosyl)-5-bromouridine (17, L-form)

A 2 M solution of HCl in Et$_2$O (2 mL) was added to a suspension of L-5-bromouridine (1 g, 3.1 mmol) in acetone (20 mL), and the mixture was stirred at room temperature for 20 h. The mixture was neutralized with 1M NH$_4$OH, and the solvent evaporated in vacuo. The residue was purified on a silica gel column (eluant: 7% MeOH in CH$_2$Cl$_2$) to give the title compound as a colorless foam (900 mg, 80%). $^1$H-NMR (DMSO-d$_6$) δ 11.78 (1H, s, NH), 6.34 (1H, s, H-1'), 5.14 (1H, d, H5'a, J=14 Hz), 4.87-4.84 (2H, m, H-2' and H-4'), 4.70 (1H, d, H-3', J=6.0 Hz), 4.59 (1H, dd, H-5'b, J=4.4, J=14 Hz), 1.46 (3H, s, CH$_3$), 1.34 (3H, s, CH$_3$).

Example 71

1-(5'-Azido-5'-deoxy-2',3'-aisopropylidine-β-L-ribofuranosyl)-5-bromouridine (19, L-form)

Methanesulfonyl chloride (0.2 mL, 2.54 mmol) was added drop-wise to a solution of 1-(2',3'-O-isopropylidine-β-L-ribofuranosyl)-5-bromouridine (17, L-form, 840 mg, 2.31 mmol) in pyridine (10 mL) at 0° C. After stirring for 1 h at 0° C., another 40 μL of MsCl was added, and the mixture stirred for a further 30 min. The reaction was quenched by addition of MeOH (2 mL). The mixture was concentrated in vacuo, and the residual solvents co-evaporated with toluene (3 times). The residue was partitioned between EtOAc and H$_2$O. The organic phase was dried over (MgSO$_4$), and the solvent evaporated. The residue was dried overnight under reduced pressure to give a colorless foam. To a solution of the foamy residue in DMF (10 mL) was added NaN$_3$ (600 mg, 9.24 mmol), and the mixture was heated for 4 h at 90° C. The insoluble material was filtered off, and the filtrate evaporated to dryness. The residue was partitioned between CH$_2$Cl$_2$ and H$_2$O. The organic phase was dried (MgSO$_4$), concentrated in vacuo, and the residue purified on a silica gel column (eluant: 4% MeOH in CH$_2$Cl$_2$) to give the title compound (774 mg, 89%) as a colorless foam. $^1$H-NMR (DMSO-d$_6$) 11.87 (1H, s, NH), 8.27 (1H, s, H-6), 5.82 (1H, s, H-1'), 5.11 (1H, br dd, H-2'), 4.75 (1H, dd, H-3', J=4.4, J=6.0 Hz), 4.13 (1H, q, H-4'), 3.61 (2H, br d, H-5'a and H-5'b), 1.48 (3H, s, CH$_3$), 1.27 (3H, s, CH$_3$).

Example 72

9,5'-Cyclo-3-(2',3'-O-isopropylidine-β-L-ribofuranosyl)-8-azaxanthine (14, Y=OH, Z=N, L-form)

1-(5'-Azido-5'-deoxy-2',3'-O-isopropylidine-β-L-ribofuranosyl)-5-bromouridine (500 mg, 1.29 mmol) was dissolved in DMF (10 mL) and heated for 72 h at 110-120° C. The mixture was concentrated in vacuo, and the residue purified by flash silica gel column chromatography (eluant: 4% MeOH in CHCl$_3$) to give the title compound (310 mg, 78%) as a white solid. $^1$H-NMR (DMSO-d$_6$) δ 11.67 (1H, s, NH), 6.31 (1H, s, H-1'), 5.17 (1H, d, H5'a, J=14 Hz), 4.95-4.89 (3H, m, H-2', H-3', and H4'), 4.62 (1H, dd, H-5'b, J=4.0, J=14.0 Hz), 1.46 (3H, s, CH$_3$), 1.23 (3H, s, CH$_3$).

Example 73

9,5'-Cyclo-3-(β-L-ribofuranosyl)-8-azaxanthine (15, Y=OH, Z=N, L-form)

A solution of 9,5'-cyclo-3-(2',3'-aisopropylidine-β-L-ribofuranosyl)-8-azaxanthine (120 mg, 0.39 mmol) in THF:1 N HCl (1:1, 10 mL) was heated at 90° C. for 2 h. The mixture was concentrated in vacuo. The residual solvents were co-evaporated with EtOH to leave a white solid, which was crystallized from EtOH to give the title compound (95 mg, 92%) as a white powder. $^1$H-NMR (DMSO-d$_6$) δ 11.58 (1H, s, NH), 5.01 (1H, s, H-1'), 5.73 (1H, d, 2'-OH, J=4.8 Hz), 5.37 (1H, d, 3'-OH, J=7.2 Hz), 4.99 (1H, d, H5'a, J=13.6 Hz), 4.79 (1H, dd, H5'b, J=13.6, J=4.0 Hz), 4.57 (1H, dd like t, H-2'), 4.17-4.07 (2H, m, H-3' and H-4').

Example 74

9,5'-Cyclo-3-(2',3'-O-isopropylidine-β-D-ribofuranosyl)-6-methylamino-8-azaxanthine (74, R=CH$_3$, R'=H)

Triethylamine (0.4 mL, 2.83 mmol) was added to a mixture of 9,5'-cyclo-3-(2',3'-O-isopropylidine-β-D-ribofuranosyl)-8-azaxanthine (14, Y=OH, Z=N, 200 mg, 0.65 mmol), DMAP (200 mg, 1.64 mmol), and triisopropylbenzenesulfonyl chloride (400 mg, 1.32 mmol) in CH$_3$CN (10 mL) at 0° C., and the mixture was stirred at room temperature for 12 h. CH$_3$NH$_2$ (2 mL) was added, and the mixture stirred for a further 2 h. The solvent was removed in vacuo, and the residue purified on a silica gel column (eluant: EtOAc:hexanes 3:1) to give the title compound (181 mg, 91%, white solid) as a mixture of (6-methylamino: 6-methylimino; 20:1). The ratio was determined from the integration ratio of the anomeric proton. $^1$H-NMR (DMSO-d$_6$) δ 8.93 (1H, q, 6-NH, J=4.8 Hz), 6.34 (1H, s, H-1'), 5.15 (1H, d, H-5'a, J=14.0 Hz), 4.87-4.84 (2H, dd, H-4' and H-3', J=4.4, J=5.6 Hz), 4.70 (1H, d, H-2', J=6.0 Hz), 4.59 (1H, dd, H-5'b, J=4.4, J=14.0 Hz), 2.90 (3H, d, N—CH$_3$, J=4.8 Hz), 1.46 (3H, s, CH$_3$), 1.24 (3H, s, CH$_3$).

Example 75

9,5'-Cyclo-3-(β-D-ribofuranosyl)-6-methylamino-8-azaxanthine (75, R=CH$_3$, R'=H)

A solution of 9,5'-cyclo-3-(2',3'-aisopropylidine-β-D-ribofuranosyl)-6-methylamino-8-azaxanthine (130 mg, 0.41 mmol) in THF:1 N HCl (1:1, 5 mL) was heated at 90° C. for 4 h. The reaction mixture was concentrated in vacuo, and the residue dried by several azeotropic distillations with EtOH. The solid residue was recrystallized from EtOH and H$_2$O to give the title compound (97 mg, 82%) as a mixture of (6-methylamino:6-methylimino; 5:1). The ratio was determined from the integration ratio of the anomeric proton. $^1$H-NMR of the major isomer (DMSO-d$_6$+D$_2$O) δ 6.03 (1H, s, H-1'), 5.04 (1H, d, H5'a, J=13.6 Hz), 4.86 (1H, dd, H-5'b, J=3.6 Hz, J=14

Hz), 4.61 (1H, dd like t, H-4', J=4.8, J=4 Hz), 4.15 (1H, t, H-3', J=4.8 Hz), 4.06 (1H, d, H-2', J=5.2 Hz), 3.74 (3H, s, N—CH$_3$).

Example 76

9,5'-Cyclo-3-(2',3'-O-isopropylidine-β-D-ribofuranosyl)-6-dimethylamino-8-azaxanthine (73, X=N(CH$_3$)$_2$)

Triethylamine (0.4 mL, 2.83 mmol) was added to a mixture of 9,5'-cyclo-3-(2',3'-O-isopropylidine-β-D-ribofuranosyl)-8-azaxanthine (14, Y=OH, Z=N, 200 mg, 0.65 mmol), DMAP (200 mg, 1.64 mmol), and triisopropylbenzenesulfonyl chloride (400 mg, 1.32 mmol) in CH$_3$CN (10 mL) at 0° C., and the mixture was stirred at room temperature for 12 h. Me$_2$NH (2 mL) was added, and the mixture stirred for a further 3 h. The solvent was removed in vacuo, and the residue purified on a silica gel column (eluant: 3% MeOH in CHCl$_3$) to give the title compound (183 mg, 84%) as a white solid. $^1$H-NMR (DMSO-d$_6$) δ 6.37 (1H, s, H-1'), 5.18 (1H, d, H-5'a, J=14.4 Hz), 4.86 (2H, dd like t, H-4' and H-3', J=5.2 Hz), 4.68 (1H, d, H-2', J=5.6 Hz), 4.58 (1H, dd, H-5'b, J=4.0, J=14.4 Hz), 3.71 (3H, s, N—CH$_3$), 3.20 (3H, s, N—CH$_3$), 1.46 (3H, s, CH$_3$), 1.24 (3H, s, CH$_3$).

Example 77

9,5'-Cyclo-3-(β-D-ribofuranosyl)-6-dimethylamino-8-azaxanthine (75, R=R'=CH$_3$)

A solution of 9,5'-cyclo-3-(2',3'-O-isopropylidine-β-D-ribofuranosyl)-6-dimethylamino-8-azaxanthine (140 mg, 0.42 mmol) in THF:1 N HCl (1:1, 5 mL) was heated for 4 h at 90° C. The mixture was concentrated in vacuo, and the residue azeotropically dried with EtOH several times. The solid residue was recrystallized from EtOH to give the title compound (101 mg, 83%) as a white powder. $^1$H-NMR (DMSO-d$_6$+D$_2$O) δ 6.05 (1H, s, H-1'), 4.96 (1H, d, H-5'a, J=14.0 Hz), 4.76 (1H, dd, H-5'b, J=4.4, J=14.0 Hz), 4.57 (1H, dd like t, H-4', J=4.0 Hz), 4.11 (1H, t, H-3', J=5.2 Hz), 3.96 (1H, t, H-2', J=5.2 Hz), 3.75 (3H, s, N—CH$_3$), 3.71 (3H, s, N—CH$_3$).

Example 78

9,5'-Cyclo-3-(2',3'-O-isopropylidine-β-D-ribofuranosyl)-6-isopropylamino-8-azaxanthine (74, R=CH(CH$_3$)$_2$, R'=H)

Triethylamine (0.4 mL, 2.83 mmol) was added to a mixture of 9,5'-cyclo-3-(2',3'-O-isopropylidine-β-D-ribofuranosyl)-8-azaxanthine (200 mg, 0.65 mmol), DMAP (200 mg, 1.64 mmol), and triisopropylbenzenesulfonyl chloride (400 mg, 1.32 mmol) in CH$_3$CN (10 mL) at 0° C. The mixture was stirred at room temperature for 12 h, then treated with isopropylamine (2 mL), and the mixture was stirred for a further 3 h at room temperature. The solvent was evaporated, and the residue purified by a flash silica gel column (eluant: 2% MeOH in CHCl$_3$) to give the title compound (162 mg, 72%, as a pale yellow solid) as a mixture of (6-iso-propylamino: 6-iso-propylimino; 9.1:1). The ratio was determined from the integration ratio of the anomeric proton. $^1$H-NMR (DMSO-d$_6$) δ 8.86 (1H, d, 6-NH, J=8.0 Hz), 6.33 (1H, s, H-1'), 5.14 (1H, d, H-5'a, J=14.0 Hz), 4.87-4.84 (2H, dd, H-4', and H-3', J=4.0, J=6.0 Hz), 4.71 (1H, d, H-2', J=6.0 Hz), 4.58 (1H, dd, H-5'b, J=4.0, J=14.0 Hz), 3.38 (1H, m, N—CHMe$_2$), 1.46 (3H, s, CH$_3$), 1.24 (3H, s, CH$_3$), 1.21 (3H, s, N—CHMe$_2$), 1.19 (3H, s, N—CHMe$_2$).

Example 79

9,5'-Cyclo-3-(2',3'-O-isopropylidine-β-D-ribofuranosyl)-6-butylamino-8-azaxanthine (74, R=n-C$_4$H$_9$, R'=H)

Triethylamine (0.4 mL, 2.83 mmol) was added to a mixture of 9,5'-cyclo-3-(2',3'-O-isopropylidine-β-D-ribofuranosyl)-8-azaxanthine (14, Y=OH, Z=N, 200 mg, 0.65 mmol), DMAP (200 mg, 1.64 mmol), and triisopropylbenzenesulfonyl chloride (400 mg, 1.32 mmol) in CH$_3$CN (10 mL) at 0° C., and the mixture was stirred at room temperature for 12 h. n-BuNH$_2$ (2 mL) was added, and the mixture stirred for a further 2 h at room temperature. The solvent was evaporated, and the residue purified by a flash silica gel column (eluant: 2% MeOH in CHCl$_3$) to give the title compound (225 mg, 95%, white solid) as a mixture of (6-butylamino: 6-butylimino; 13.6:1). The ratio was determined from the integration ratio of the anomeric proton. $^1$H-NMR (DMSO-d$_6$) δ 9.00 (1H, t, 6-NH, J=5.6 Hz), 6.33 (1H, s, H-1'), 5.16 (1H, d, H-5'a, J=14.0 Hz), 4.88-4.84 (2H, dd, H-4' and H-3', J=4.0, J=6.0 Hz), 4.71 (1H, d, H-2', J=6.0 Hz), 4.60 (1H, dd, H-5'b, J=4.0, J=14.0 Hz), 3.41 (2H, m, N-Bu), 1.59-1.52 (2H, m, N-Bu), 1.46 (3H, s, CH$_3$), 1.37-1.28 (2H, m, N-Bu), 1.24 (3H, s, CH$_3$), 0.90 (3H, t, N-Bu, J=5.6 Hz).

Example 80

9,5'-Cyclo-3-(β-D-ribofuranosyl)-6-butylamino-8-azaxanthine (75, R=n-C$_4$H$_9$, R'=H)

A solution of 9,5'-cyclo-3-(2',3'-O-isopropylidine-β-D-ribofuranosyl)-6-butylamino-8-azaxanthine (74, R=n-C$_4$H$_9$, 150 mg, 0.41 mmol) in THF:1 N HCl (1:1, 10 mL) was stirred for 24 h at room temperature. The solvent was evaporated, and the residue partitioned between CHCl$_3$ and H$_2$O. The aqueous phase was evaporated in vacuo to leave the title compound (96 mg, 85%, as a white powder) as a mixture of (6-butylamino: 6-butylimino; 13.6:1). The ratio was determined from the integration ratio of the anomeric proton. $^1$H-NMR (DMSO-d$_6$+D$_2$O) δ 6.00 (1H, s, H-1'), 4.94 (1H, d, H5'a, J=13.6 Hz), 4.76 (1H, dd, H-5'b, J=4.0, J=13.6 Hz), 4.54 (1H, dd like t, H-4', J=3.6), 4.12 (1H, dd like t, H-3', J=5.2 Hz), 3.96 (1H, d, H-2', J=5.2 Hz), 3.40 (2H, m, N-Bu), 1.59-1.52 (2H, m, N-Bu), 1.37-1.28 (2H, m, N-Bu), 0.90 (3H, t, N-Bu, J=7.2 Hz).

Example 81

9,5'-Cyclo-3-(2',3'-O-isopropylidine-β-D-ribofuranosyl)-6-tetrahydro-2H-pyran-2-yl-hydroxylamino-8-azaxanthine (74, R=OTHP, R'=H)

Triethylamine (0.4 mL, 2.83 mmol) was added to a mixture of 9,5'-cyclo-3-(2',3'-O-isopropylidine-β-D-ribofuranosyl)-8-azaxanthine (200 mg, 0.65 mmol), DMAP (200 mg, 1.64 mmol), and triisopropylbenzenesulfonyl chloride (400 mg, 1.32 mmol) in CH$_3$CN (10 mL) at 0° C., and the mixture was stirred at room temperature for 16 h. O-Tetrahydro-2H-pyran-2-yl-hydroxylamine (1 g) was added, and the mixture stirred for a further 12 h. The solvent was removed in vacuo, and the residue purified by a flash silica gel column (eluant: 2% MeOH in CHCl$_3$) to give the title compound (243 mg, 92%) as a white solid. $^1$H-NMR (DMSO-d$_6$) δ 10.68 (1H, s, NH), 6.26 (1H, s, H-1'), 5.14 (2H, m, H5'a and H-1"-THP), 4.96-4.84 (3H, m, H-2', H-3', and H5'b), 4.62 (1H, m, H-4'), 3.80 (1H, m, THP), 3.48 (1H, m, THP), 1.71 (2H, m, THP), 1.49 (2H, m, THP), 1.46 (3H, s, CH$_3$), 1.23 (3H, s, CH$_3$).

Example 82

9,5'-Cyclo-3-(2',3'-O-isopropylidine-β-D-ribofuranosyl)-6-methoxylamino-8-azaxanthine (74, R=OCH$_3$, R'=H)

Triethylamine (0.4 mL, 2.83 mmol) was added to a mixture of 9,5'-cyclo-3-(2',3'-O-isopropylidine-β-D-ribofuranosyl)-8-azaxanthine (177 mg, 0.58 mmol), DMAP (200 mg, 1.64 mmol), and triisopropylbenzenesulfonyl chloride (400 mg, 1.32 mmol) in CH$_3$CN (10 mL) at 0° C. The mixture was stirred at room temperature for 16 h, then treated with a solution of methoxylamine hydrochloride (1 g) in dry pyridine (10 mL), and the mixture was stirred for a further 12 h. The solvent was evaporated, and the residue purified by a flash silica gel column (eluant: 2% MeOH in CHCl$_3$) to give the title compound (168 mg, 86%) as a white solid. $^1$H-NMR (DMSO-d$_6$) δ 10.53 (1H, s, NH), 6.24 (1H, s, H-1'), 5.14 (1H, d, H5'a, J=14.4 Hz), 4.92-4.83 (3H, m, H-2', H-3', and H4'), 4.55 (1H, dd, H-5'b, J=4.0, J=14.4 Hz), 3.78 (3H, s, NOCH$_3$), 1.45 (3H, s, CH$_3$), 1.24 (3H, s, CH$_3$).

Example 83

9,5'-Cyclo-3-(β-D-ribofuranosyl)-6-methoxylamino-8-azaxanthine (75, R=OCH$_3$, R'=H)

A solution of 9,5'-cyclo-3-(2',3'-O-isopropylidine-β-D-ribofuranosyl)-6-methoxylamino-8-azaxanthine (74, R=OCH$_3$, 80 mg, 0.23 mmol) in TFA:H$_2$O (2:1, 6 mL) was stirred for 24 h at room temperature. The solvents were evaporated and co-evaporated with EtOH several times, and the residue partitioned between CHCl$_3$ and H$_2$O. The aqueous phase was evaporated in vacuo, and the residue purified by a silica gel column (eluant: 12% MeOH in CHCl$_3$) to give the title compound (44 mg, 60%) as a white solid. $^1$H-NMR (DMSO-d$_s$+D$_2$O) δ 5.95 (1H, s, H-1'), 4.92 (1H, d, H5'a, J=14.0 Hz), 4.74 (1H, dd, H-5'b, J=4.0, J=14.0 Hz), 4.61 (1H, dd like t, H-4', J=4.4 Hz), 4.13 (1H, t, H-3', J=4.8 Hz), 4.03 (1H, d, H-2', J=5.2 Hz), 3.78 (3H, s, N-OMe).

Example 84

9,5'-Cyclo-3-(2',3'-aisopropylidine-β-D-ribofuranosyl)-6-benzylamino-8-azaxanthine (74, R=CH$_2$Ph, R'=H)

Triethylamine (0.4 mL, 2.83 mmol) was added to a mixture of 9,5'-cyclo-3-(2',3'-O-isopropylidine-β-D-ribofuranosyl)-8-azaxanthine (14, Y=OH, Z=N, 200 mg, 0.65 mmol), DMAP (200 mg, 1.64 mmol), and triisopropylbenzenesulfonyl chloride (400 mg, 1.32 mmol) in CH$_3$CN (10 mL) at 0° C., and the mixture was stirred at room temperature for 16 h. BnNH$_2$ (2 mL) was added, and the mixture stirred for a further 12 h. The solvent was removed in vacuo, and the residue purified by a flash silica gel column (eluant: EtOAc: hexanes 3:1) to give the title compound (218 mg, 85%, white solid) as a mixture of (6-benzylamino: 6-benzylimino; 13.3: 1). The ratio was determined from the integration ratio of the anomeric proton. $^1$H-NMR (DMSO-d$_6$+D$_2$O) δ 7.366-7.26 (5H, m, Bn), 6.33 (1H, s, H-1'), 5.13 (1H, d, H-5'a, J=14.4 Hz), 4.87 (2H, m, H-3' and H-4'), 4.71 (1H, d, H-2', J=5.6 Hz), 4.65-4.59 (4H, m, H-5'b, and CH$_2$Ph), 1.47 (3H, s, CH$_3$), 1.25 (3H, s, CH$_3$).

Example 85

9,5'-Cyclo-3-(β-D-ribofuranosyl)-6-benzylamino-8-azaxanthine (75, R=CH$_2$Ph, R'=H)

A solution of 9,5'-cyclo-3-(2',3'-O-isopropylidine-β-D-ribofuranosyl)-6-benzylamino-8-azaxanthine (100 mg, 0.25 mmol) in THF:1 N HCl (1:1, 10 mL) was heated for 4 h at 90° C. The mixture was cooled to room temperature, and the solvent evaporated in vacuo. The residue was partitioned between CHCl$_3$ and H$_2$O. The aqueous phase was evaporated in vacuo, and the residue purified by a flash silica gel column (eluant: 10% MeOH in CHCl$_3$) to give the title compound (746 mg, 85%) as a white solid.

Example 86

3-Benzyloxymethyl-5-bromo-1-(2',3'-O-isopropylidene-5'-O-trityl-β-D-ribofuranosyl)uracil (133)

Benzyloxymethyl chloride (9.4 g, 60 mmol) was added dropwise to a mechanically stirred solution of 132 (30 g, 50 mmol) and DBU (10 g, 60 mmol) in dry DMF (400 mL) at 0° C. The mixture was stirred for 5 additional hours at 0° C. and then concentrated in vacuo. The residue was partitioned between methylene chloride (400 mL) and water (200 mL). The organic layer was separated, washed with water (2×200 mL), dried over sodium sulfate, and concentrated to dryness. The residue was dissolved in methylene chloride and chromatographed over a silica gel column using methylene chloride as the eluant, to give 35.5 g (92%) of 133 as a syrup, sufficiently pure to be used in the next step. Anal. Calc'd. for C$_{39}$H$_{37}$BrN$_2$O$_7$: C, 64.55; H, 5.14; Br, 11.01; N, 3.86. Found: C, 64.73; H, 5.33; Br, 10.89; N, 3.83. $^1$H-NMR (Me$_2$SO-d$_6$) δ 7.86 (s, 1H, H-6), 7.35 (m, 2H, 2OH, Ph), 5.84 (d, 1H, H-1', J$_{1',2'}$=2.4 Hz), 5.48 (ABq, 2H, NCH$_2$, J$_{gem}$=10.0 Hz), 4.81 (m, 2H, H-2' and 3'), 4.70 (s, 2H, PhCH$_2$), 4.38 (m, 1H, H-4'), 3.39 (d, 2H, H-5' and 5"), 1.58, 1.35 (2s, 3H each, iPr).

Example 87

3-Benzyloxymethyl-5-cyano-1-(2',3'-O-isopropylidene-5'-O-trityl-β-D-ribofuranosyl)uracil (134)

A mixture of 132 (36.0 g, 50 mmol) and sodium cyanide (6 g, 75 mmol) in DMF (400 mL) was heated at 80° C. for 5 hours and then concentrated in vacuo. The residue was partitioned between water (800 mL) and ethyl acetate (400 mL). The organic layer was washed with water (3×400 mL), dried over sodium sulfate, concentrated in vacuo, and the residue chromatographed using n-hexane-ethyl acetate (17:3 v/v) as the eluant to give 134 (26.5 g, 80%) as a syrup, sufficiently pure to be used in the next step. Anal. Calc'd. for C$_{40}$H$_{37}$N$_3$O$_7$: C, 71.52; H, 5.55; N, 6.24. Found: C, 71.31; H, 5.67; N, 6.24. $^1$H-NMR (Me$_2$SO-d$_6$) δ 8.05 (s, 1H, H-6), 7.31 (m, 2H, 2OH, Ph), 5.74 (d, 1H, H-1', J$_{1',2'}$=2.4 Hz), 5.47 (ABq, 2H, NCH$_2$, J$_{gem}$=10.0 Hz), 4.82 (m, 2H, H-2' and 3'), 4.71 (s, 2H, PhCH$_2$), 4.34 (m, 1H, H-4'), 3.38 (d, 2H, H-5' and 5"), 1.60, 1.39 (2s, 3H each, iPr).

Example 88

7-Amino-3-benzyloxymethyl-6-ethoxycarbonyl-1-(2',3'-O-isopropylidene-5'-O-trityl-β-D-ribofuranosyl)pyrido[2,3-d]pyrimidine-2,4(1H,3H)-dione (135)

A solution of 134 (10 g, 14.8 mmol) and ethyl cyanoacetate (2.5 g) in sodium ethoxide in ethanol (prepared by dissolving 700 mg of metallic sodium in 200 mL of ethanol) is heated at reflux for 30 minutes. The reaction mixture is diluted with water (200 mL), and the precipitates are collected by decantation of the supernatant. The residue is dissolved in chloroform, the solution is dried over sodium sulfate, and purified by chromatography on a silica gel column using hexane-ethyl acetate (7:3 v/v) as the eluant. Compound 135 (8.5 g, 75%) is obtained as an amorphous powder.

Anal. Calc'd. for $C_{45}H_{44}N_4O_9 \cdot H_2O$: C, 67.33; H, 5.74; N, 6.98. Found: C, 67.38; H, 5.63; N, 6.74. $^1$H-NMR (Me$_2$SO-d$_6$) δ 8.91 (s, 1H, H-5), 7.30 (m, 2OH, Ph), 5.77 (br s, 2H, NH$_2$), 5.28 (ABq, 2H, NCH$_2$, $J_{gem}$=10.0 Hz), 5.19 (d, 1H, H-1', $J_{1',2}$ 0.2 Hz), 4.90 (m, 1H, H-2'), 4.60 (s, 2H, PhCH$_2$), 4.39 (q, 2H, CH$_2$Me), 4.30-4.45 (m, 2H, H-3' and 4'), 3.35 (m, 2H, H-5' and 5"), 1.59 (s, 3H, iPr), 1.41 (t, 3H, CH$_2$Me), 1.34 (s, 3H, iPr).

Example 89

7-Amino-6-ethoxycarbonyl-1-(2',3'-O-isopropylidene-β-D-ribofuranosyl)pyrido[2,3-d]pyrimidine-2,4(1H,3H)-dione (136)

Compound 135 (7.7 g, 10 mmol), 10% Pd/C (3.6 g), ethanol (200 mL), and ethyl acetate (200 mL) are shaken at room temperature for 40 hours in a Parr hydrogenator in a hydrogen atmosphere with an initial pressure of 40 p.s.i. The catalyst is removed by filtration, and washed with ethanol (3×150 mL). The combined filtrate and washings are concentrated to dryness in vacuo to give 136 (4.0 g, 75%), a colorless powder, mp>300° C. $^1$H-NMR spectrum of the product is consistent with the structure. This product is used directly in the next step.

Example 90

6-Ethoxycarbonyl-1-(2',3'-O-isopropylidene-β-D-ribofuranosyl)pyrido[2,3-d]pyrimidine-2,4,7(1H,3H,8H)-trione (137)

An ice-cold mixture of 136 (2.1 g, 5 mmol) in 50 mL of 50% aqueous acetic acid is treated with sodium nitrite (1 g, 14.5 mmol) with stirring. The mixture is gradually warmed to room temperature and allowed to stand overnight. The solvent is evaporated in vacuo, and traces of acetic acid are azeotropically removed with toluene. The residue is triturated with water, and colorless precipitates are collected by filtration, washed with small amounts of ethanol, and dried to give 137 (1.9 g, 90%) as an amorphous powder. $^1$H NMR spectrum of the product is consistent with the structure. This product is used directly in the next step.

Example 91

8,5'-Cyclo-6-ethoxycarbonyl-1-(2',3'-O-isopropylidene-β-D-ribofuranosyl)pyrido[2,3-d]pyrimidine-2,4,7(1H,3H,8H)-trione (138)

To a refluxing mixture of 137 (1.7 g, 4 mmol) and triphenyl-phosphine (1.4 g, 5 mmol) in tetrahydrofuran and water (19:1 v/v, 75 mL) is added dropwise diethyl azodicarboxylate until the slightly yellow color of the reaction mixture persists (ca. 0.8-1 mL). The solvent is removed in vacuo, and the residue is purified on a silica gel column eluating first with toluene, followed by methylene chloride-ethyl acetate (7:3 v/v). Compound 138 (1.2 g, 74%) is obtained as a colorless powder, mp>300° C. $^1$H NMR is consistent with the structure.

Example 92

8,5'-Cyclo-6-ethoxycarbonyl-1-(β-D-ribofuranosyl)pyrido[2,3-d]pyrimidine-2,4,7(1H,3H,8H)-trione (139)

Compound 138 (200 mg, 0.5 mmol) is dissolved in 90% trifluoroacetic acid at room temperature, and the solution is kept overnight and then evaporated in vacuo. The solid residue is triturated several times with ethanol and air dried to give 139 (181 mg, 99%), mp>300° C. $^1$H NMR is consistent with the structure.

Example 93

8,5'-Cyclo-1-(β-D-ribofuranosyl)pyrido[2,3-d]pyrimidine-2,4,7(1H,3H,8H)-trione-6-carboxamide (140)

Compound 139 (100 mg, 0.27 mmol) is treated with liquid ammonia (ca. 5 mL) overnight at room temperature, and the ammonia is evaporated. The solid residue is recrystallized from ethanol to give 140 (87 mg, 95%), mp>300° C. $^1$H NMR is consistent with the structure.

Example 94

8,5% Cyclo-6-cyano-1-(β-D-ribofuranosyl)pyrido[2,3-d]pyrimidine-2,4,7(1H,3H,8H)-trione (141)

To an ice-cooled solution of 140 (34 mg, 0.1 mmol) in dioxane (5 mL) and pyridine (0.5 mmol) is added trifluoroacetic anhydride (0.5 mL) with stirring. The mixture is stirred an additional 3 hours at room temperature. The reaction is quenched by addition of water (2 mL), and the mixture is concentrated to dryness in vacuo. The residue is azeotropically dried with toluene and then recrystallized from ethanol-water to give 141 (24 mg, 78%), mp >300° C. IR (KBr) u 2220 cm$^{-1}$ (CN).

Biological Methods

Example 95

Antiviral Testing of Candidate Compounds for Flaviviridae

The HCV replicon system in Huh7 cells.

Huh7 cells harboring the HCV replicon were cultivated in DMEM medium (high glucose, no pyruvate), supplemented with 10% fetal bovine serum, 1× non-essential amino acids, Pen-Strep-Glu (100 units/liter, 100 microgram/liter, and 2.92 mg/liter, respectively), and G418 (500 to 1000 microgram/milliliter). Antiviral screening assays were also done in the same medium without G418 as follows. To keep the cells in the logarithmic growth phase, cells were seeded in 96-well plates at low density (for example, 1000 cells per well). The test compound was then added immediately after seeding the cells, and they were incubated for 3 to 7 days at 37° C. in an incubator. The medium was then removed, and the cells were prepared for total RNA extraction (replicon RNA+host RNA). Replicon RNA was then amplified in a real-time RT-PCR (Q-RT-PCR) protocol, and quantified.

The observed differences in quantification of replicon RNA are one way to express the antiviral potency of the test compound. In a typical experiment, in the negative control and with non-active compounds a comparable amount of replicon was produced. This can be concluded because the measured threshold-cycle for HCV RT-PCR in both settings was approximately the same. In such experiments, a way to express the antiviral effectiveness of a compound is to subtract the average threshold RT-PCR cycle of the negative control ($Ct_{negative}$) from the threshold RT-PCR cycle of the test compound ($Ct_{testcompound}$). This value is called ΔCt (ΔCt=$Ct_{testcompound}$−$Ct_{negative}$). A ΔCt value of 3.3 represents a 1-log reduction in replicon production.

As a positive control, recombinant interferon alfa-2a (Roferon-A, Hoffmann-Roche, NJ, USA) was taken alongside, showing a HCV ΔCt of 7. Furthermore, each of these compounds were tested in dilution series (typically at 100, 33, 10, 3 and 1 μM). The ΔCt values for each concentration allow the calculation of the 50% effective concentration ($EC_{50}$).

Cell Culture Systems for Determining Antiviral Activities

The assay described above can be adapted to the other members of the Flaviviridae by changing the cell system and the viral pathogen. Methodologies to determine the efficacy of these antiviral compounds include modifications of the standard techniques as described by Holbrook M R et al. *Virus Res.* 2000, 69, 31; Markland W et al. *Antimicrob. Agents. Chemother.* 2000, 44, 859; Diamond M S et al., *J. Virol.* 2000, 74, 7814; Jordan I et al. *J. Infect. Dis.* 2000, 182, 1214; Sreenivasan V et al. *J. Virol. Methods* 1993, 45 (1), 1; or Baginski S G et al. *Proc. Natl. Acad. Sci. U.S.A.* 2000, 97 (14), 7981 or the real-time RT-PCR technology. As an example, an HCV replicon system in HuH7 cells (Lohmann V et al. *Science,* 1999, 285 (5424), 110) or modifications thereof (Blight et al. 2000) can be used.

Biological Test Results.

Compounds were tested for inhibition of HCV RNA replication using the above assay. Examples of the results are shown in the following table.

| ID | Structure | ΔCt HCV at 100 μM | EC50 (μM) ΔCt HCV |
|---|---|---|---|
| 15 (Y = H, Z = CH) | 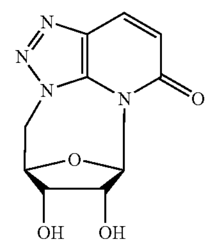 | 4.48 | 20 |
| 15 (Y = OH, Z = N) | 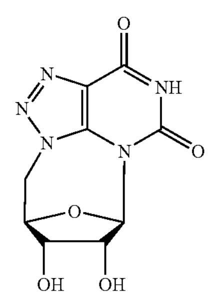 | 6.3 | <10 |
| 71 (X = Br) | 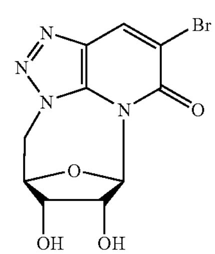 | 5.9 | <1 |
| 71 (X = Cl) | 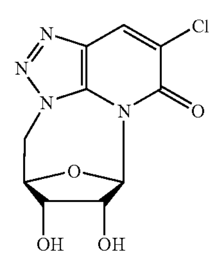 | 6.0 | <0.7 |

-continued
| ID | Structure | ΔCt HCV at 100 μM | EC50 (μM) ΔCt HCV |
|---|---|---|---|
| 70 | 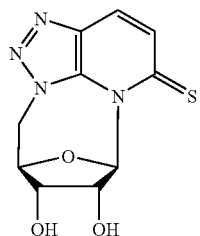 | 7.0 | 1 |
| 75 (R = R' = H) | 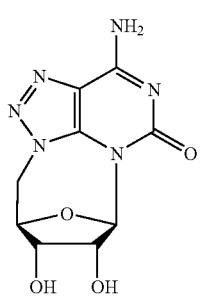 | 5.3 | 0.7 |
| 15 (Y = H, Z = N) | 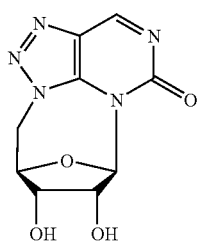 | 3.6 | <10 |
| 83 (Y = OH, Z = N) | 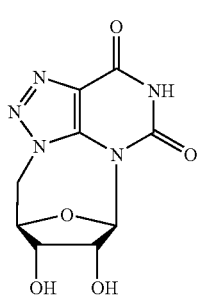 | 2.1 | 60 |
| 82 (Y = OH, Z = N) | 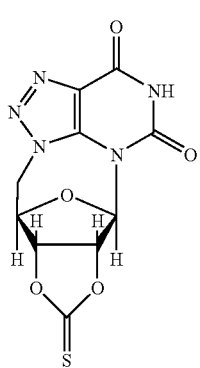 | 4.7 | 12 |

-continued
| ID | Structure | ΔCt HCV at 100 μM | EC50 (μM) ΔCt HCV |
|---|---|---|---|
| 15 (Y = SH, Z = N) | 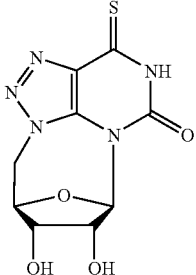 | 3.61 | <6 |
| 73 (Y = SH) | 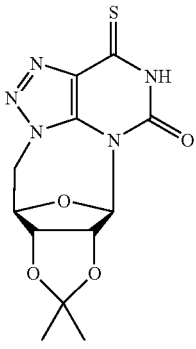 | 4.1 | 25 |
| 82 (Y = H, Z = CH) | 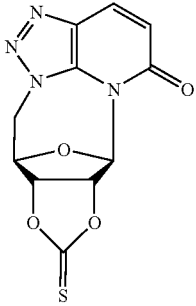 | 2.6 | |
| 77 (R = CH$_3$) | 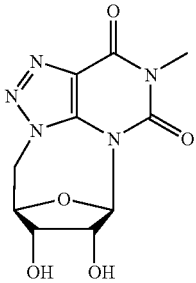 | 5.9 | 0.4 |
| 77 (R = CH$_2$CN) | 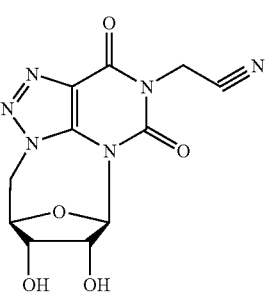 | 4.7 | <6 |

-continued

| ID | Structure | ΔCt HCV at 100 μM | EC50 (μM) ΔCt HCV |
|---|---|---|---|
| 83 (Y = H, Z = CH) | 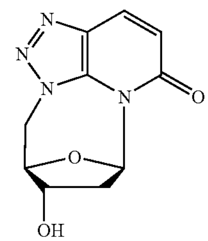 | 5.1 | <6 |
| 75 (R = R' = Me) | 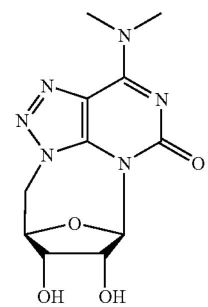 | 2.4 | |
| 75 (R = Me, R' = H) | 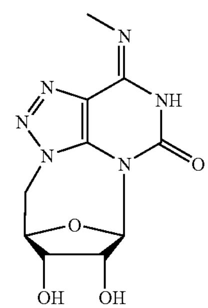 | 6.4 | <6 |
| 75 (R = OMe, R' = H) | 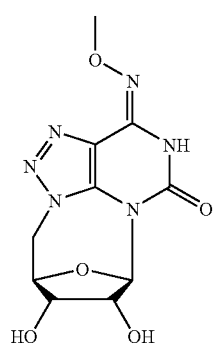 | 6.5 | <5 |
| 72 (R = H, R' = Me) | 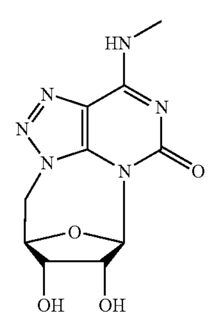 | 6.6 | <1 |

| ID | Structure | ΔCt HCV at 100 µM | EC50 (µM) ΔCt HCV |
|---|---|---|---|
| 35 | 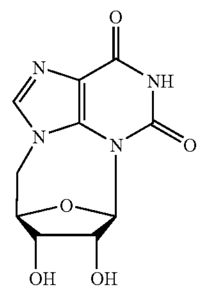 | 6.0 | 4 |
| 27 | 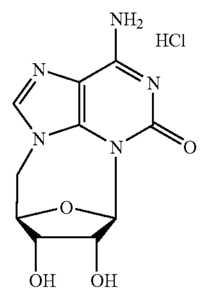 | 6.6 | <3 |
| 72 (R = R' = H) | 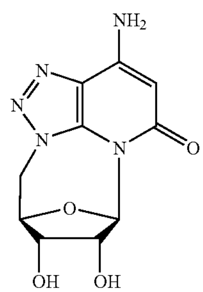 | 5.7 | 4.5 |
| 65 | 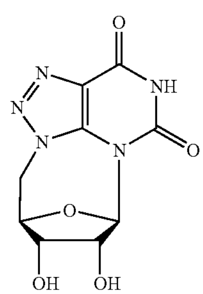 | 2.4 | |

Example 96

Compound 15 (Y=H, Z=CH) has demonstrated in vitro antiviral activity against HCV. The compound showed practically no toxicity in several human cell lines. In Swiss outbred mice, no toxicity was apparent when it was given IP for 6 consecutive days at up to 100 mg/kg. None of the mice died or lost significant weight (28 day monitoring). Neither oral administration nor IV administration to rhesus monkeys at 20 mg/kg caused any untoward effects.

Based on those toxicity data, a 14-day treatment (oral, QD at 5 mg/kg/day) of chronically HCV-infected chimpanzees was conducted. Viral RNA was extracted from the chronically infected chimpanzees serum samples in quadruplicate and the viral RNA pellets were dissolved in RNAse-free water. Subsequently, these RNA samples were amplified by real-time RT-PCR (Applied Biosystems, Foster City, Calif.) for the presence and quantity of the HCV nucleic acids. Primers and probes for HCV were designed using Primer Express (Applied Biosystems). Further details on the methodology will be published (Stuyver et al., 2002; manuscript submitted to *Antimicrob. Agents Chemother.*).

The results are expressed relative to the viral load in the pretreatment sample. Calculation of the viral load for each sample was based on 4 independent measurements of threshold RT-PCR cycles (Ct values). Mean±SD were calculated for each day's sample. The latter were used to express the observed viral load changes.

Two chimpanzees [Joseph (5.14 $\log_{10}$ IU/ml HCV) and Heppie (5.69 $\log_{10}$ IU/ml HCV)] were treated orally for 14 days with 5 mg/kg/day. The viral load changes that were observed are summarized below (FIG. 1):

1. Similar reductions in HCV viral load were observed in both chimpanzees;
2. No viral load changes were observed up to 24 hr after administration of the first dose;
3. At day 4, a maximal drop of 0.8 $\log_{10}$ IU/ml in HCV viral load was observed for Heppie and 0.5 $\log_{10}$ IU/ml for Joseph, with a mean of 0.67 $\log_{10}$ IU/ml for both animals;
4. The viral load remained suppressed with a mean of 0.43 $\log_{10}$ IU/ml up to day 14.

Hematology and blood chemistry report. The day 0 and day 14 samples were analyzed for hematological and blood chemistry parameters. Essentially, no changes in the baseline and after treatment samples were observed. All parameters assessed remained in the normal range throughout the study.

Compound 15 (Y=H, Z=CH) administered at 5 mg/kg/day QD to chronically infected chimpanzees resulted in a significant reduction in viral load at day 4. No change in hematological or blood chemistry parameters was observed.

We claim:
1. A compound of the formula:

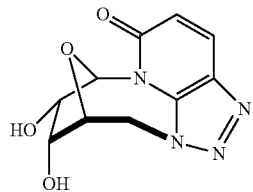

or a pharmaceutically acceptable salt thereof.

* * * * *